(12) United States Patent
Nefzi et al.

(10) Patent No.: US 6,809,202 B2
(45) Date of Patent: Oct. 26, 2004

(54) DIKETODIAZACYCLIC COMPOUNDS, DIAZACYCLIC COMPOUNDS AND COMBINATORIAL LIBRARIES THEREOF

(75) Inventors: Adel Nefzi, San Diego, CA (US); John M. Ostresh, Encinitas, CA (US); Richard A. Houghten, DelMar, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 54 days.

(21) Appl. No.: 10/164,688

(22) Filed: Jun. 6, 2002

(65) Prior Publication Data

US 2003/0120066 A1 Jun. 26, 2003

Related U.S. Application Data

(60) Division of application No. 09/310,662, filed on May 12, 1999, now Pat. No. 6,441,172, which is a continuation-in-part of application No. 08/745,793, filed on Nov. 7, 1996, now Pat. No. 5,786,448.

(51) Int. Cl.[7] ............................................. C07D 241/04
(52) U.S. Cl. ...................... 544/383; 544/384; 544/386; 544/387; 544/389; 544/404
(58) Field of Search ................................ 544/383, 384, 544/386–387, 389, 404

(56) References Cited

U.S. PATENT DOCUMENTS

| | | | | |
|---|---|---|---|---|
| 3,267,104 A | * | 8/1966 | Hermans et al. ............ | 260/268 |
| 4,346,087 A | | 8/1982 | Hamanaka et al. | |
| 5,143,854 A | | 9/1992 | Pirrung et al. .............. | 436/518 |
| 5,182,366 A | | 1/1993 | Huebner et al. ............ | 830/334 |
| 5,367,053 A | | 11/1994 | Dooley et al. .............. | 530/329 |
| 5,556,762 A | | 9/1996 | Pinilla et al. ............... | 435/7.21 |
| 5,786,448 A | | 7/1998 | Nefzi et al. ................. | 530/317 |
| 6,441,172 B1 | * | 8/2002 | Nefzi et al. ................. | 544/383 |

FOREIGN PATENT DOCUMENTS

| | | |
|---|---|---|
| EP | 0 138 855 | 9/1999 |
| JP | 54-95581 | 7/1979 |
| WO | WO 92/09300 | 6/1992 |
| WO | WO 96/40202 | 12/1996 |
| WO | WO 97/23467 | 7/1997 |

OTHER PUBLICATIONS

English translation (pp. 1–29) of JP54–95581 (1979).*
Gordon et al., "Reductive Alkylation on a Solid Phase: Synthesis of a Piperazinedione Combinatorial Library", Bioorg. & Med. Chem. Lett., 5(1), 47–50 (1995).
Gordon et al., "Applications of Combinatorial Technologies to Drug Discovery. 1. Background and Peptide Libraries", J. Med. Chem., 29: 37(9) 1233–1251 (Apr. 1994).
Gordon et al., Applications of Combinatorial Technologies to Drug Discovery. 2. Combinatorial Organic Synthesis, Library Screening Strategies, and Future Directions., J. Med. Chem., 13:37(10) 1385–1401 (May 1994).
Terrett et al., Combinatorial Synthesis—The Design of Compound Libraries and Their Application to Drug Discovery, Tetrahedron, 51(30) 8135–8173 especially 8158 (1995).
Gordon, D., et al., BioMed. Chem. Lett., 5:47–50 (1995).
Ostresh, et al., J. Org. Chem., 63:8622–23 (1998).
Nefzi, et al., Tetrahedron, 55:335–344 (1999).
Houghten, et al., Nature, 354:84–86 (1991).
Dooley, et al., Science, 266:2019–2022 (1994).
Houghten, R.A., Proc. Natl. Acad. Sci. USA, 82:5131–35 (1985).
Houghten, R.A., et al., Int. J. Pep. Pro. Res., 27, 6763 (1986).
Krchnak, V., et al., Molecular Diversity and Combinatorial Chemistry: Libraries and Drug Discovery, Chaiken, I.M., et al., Eds., American Chemical Society: Washington, D.C., 99–117 (1996).
Scott, B.O., et al., Mol. Diversity, 1:125–134 (1995).

* cited by examiner

Primary Examiner—Bennett Celsa
(74) Attorney, Agent, or Firm—Welsh & Katz, Ltd.

(57) ABSTRACT

The synthesis of individual di- and tri-substituted-1,4-diazacyclic compounds having 6- to 8-atoms in the cyclic ring, their corresponding 1,6-diketo-2,5-diazacyclic compounds and similar 1,4-diazacyclic ring compounds having one ring carbonyl gorup and 6–8 atoms in the ring is disclosed, as are libraries of such compounds. Methods of preparing and using the libraries of compounds as well as individual compounds of the libraries are also disclosed.

12 Claims, No Drawings

DIKETODIAZACYCLIC COMPOUNDS, DIAZACYCLIC COMPOUNDS AND COMBINATORIAL LIBRARIES THEREOF

CROSS-REFERENCE TO RELATED APPLICATION

This is a division of application Ser. No. 09/310,662, filed May 12, 1999 now U.S. Pat. No. 6,441,172, which is a continuation-in-part of application Ser. No. 08/745,793, filed Nov. 7, 1996 now U.S. Pat. No. 5,786,448, whose disclosures are incorporated herein by reference.

TECHNICAL FIELD

The invention relates to the synthesis of individual di- and tri-substituted-1,4-diazacyclic compounds having 6- to 8-atoms in the cyclic ring, their corresponding 1,6-diketo-2,5-diazacyclic compounds and similar 1,4-diazacyclic ring compounds having one ring carbonyl gorup and 6–8 atoms in the ring, and libraries of such compounds. The present invention further relates to methods of preparing and using the libraries of compounds as well as individual compounds of the libraries.

BACKGROUND ART

Heterocyclic compounds having a high degree of structural diversity have proven to be broadly and economically useful as therapeutic agents. [For reviews on solid phase organic synthesis, see: (a) Gallop, M. A. et al., *J. Med. Chem.*, 1994, 37, 1233. (b) Gordon, E. M. et al., *J. Med. Chem.*, 1994, 37, 1385. (c) Thompson, L. A. et al., *Angew. Chem. Int. Ed. Engl.*, 1996, 35, 17.(e) Hermkens, P. H. H. et al., *Tetrahedron*, 1996, 52, 4527. (f) Nefzi, A. et al., *Chem. Rev.* 1997, 97, 449.] A number of approaches have been reported for the solid phase synthesis of diketopiperazine derivatives: Gordon and Steele developed a strategy for the solid phase synthesis of diketopiperazines based on reductive amination on the solid support [Gordon, D. et al., *BioMed. Chem. Lett.*, 1995, 5, 47]. A similar approach has been published by Krchnàk and co-workers for the synthesis of persubstituted 2,5-diketopiperazines [Krchnàk, V. et al., *In Molecular Diversity and Combinatorial Chemistry: Libraries and Drug Discovery*; Chaiken, I. M., Janda, K. D. Eds., American Chemical Society: Washington, DC. 1996, pp 99–117], and Scott and co-workers developed an alternative strategy for the synthesis of a similar diketopiperazine library using bromocarboxylic acids and a range of amines [Scott, B. O. et al., *Mol. Diversity*, 1995, 1, 125].

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow the preparation of up to thousands of related compounds in a matter of days or a few weeks. This need is particularly evident when it comes to synthesizing more complex compounds, such as the 4,5-disubstituted-2,3-diketopiperazine and 1,4,5-trisubstituted-2,3-diketopiperazine compounds of the present invention.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described for example by Dooley in U.S. Pat. No. 5,367,053; Huebner in U.S. Pat. No. 5,182,366; Appel et al in WO PCT 92/09300; Geysen in published European Patent Application 0 138 855 and Pimmg in U.S. Pat. No. 5,143,854. Such SCLs provide the efficient synthesis of an extraordinary number of various peptides in such libraries and the rapid screening of the library which identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds which can maintain high affinity and specificity toward biological receptors but which have improved pharmacological properties relative to peptides.

Combinatorial approaches have recently been extended to "organic" or non-peptide libraries. The organic libraries to the present, however, are of limited diversity and generally relate to peptidomimetic compounds; in other words, organic molecules that retain peptide chain pharmacophore groups similar to those present in the corresponding peptide. Although the present invention is principally derived from the synthesis of dipeptides, the dipeptides are substantially modified. In short, they are chemically modified through alkylation, acylation, reduction, and cyclization into the subject diketopiperazines, thus providing mixtures and individual compounds of substantial diversity.

Significantly, many biologically active compounds contain diketopiperazines. Diketopiperazines are conformationally constrained scaffolds that are quite common in nature, and many natural products containing a diketopiperazine structure have been isolated that encompass a wide range of biological activities. Included in such compounds are inhibitors of the mammalian cell cycle reported by Cui et al., *J. Antibiot.*, 47:1202 (1996), inhibitors of plasminogen activator-1, and topoisomerase reported by Charlton et al., *P. Thromb. Haeomast.*, 75:808 (1996) and Funabashi et al., *J. Antibiot.*, 47:1202 (1994). Diketopiperazines have been reported by Terret et al., *Tetrahedron*, 51:8135 (1995) to be useful as ligands to the neurokinin-2 receptor. Barrow et al., *Bioorg. Med. Chem. Lett.*, 5:377 (1996) found diketopiperazines to be competitive antagonists to Substance P at the neurokinin-1 receptor. Because, diketopiperazine moieties are found in many biologically active compounds and are known to have useful therapeutic implications, there is a need to further study and develop large numbers of 2,3-diketopiperazine compounds and their analogues of larger ring size.

This invention satisfies these needs and provides related advantages as well. The present invention overcomes the known limitations to classical organic synthesis of cyclic 2,3-diketopiperazines. Existing reported approaches for the synthesis of diketopiperazines describe only the synthesis of 2,5-diketopiperazines, the present invention provides a large array of diverse 1,4,5-trisubstituted- and 4,5-disubstituted-2,3-diketopiperazine compounds that can be screened for biological activity, related piperazine and larger ringed compounds, as described below, that exhibit biological activity.

BRIEF SUMMARY OF THE INVENTION

The invention provides a rapid synthesis of (1-substituted or 1,2-disubstituted)-(4-aminoalkyl)-1,4-diazacyclic compounds having 6- to 8-atoms in the cyclic ring and the corresponding 1,6-diketo-(2-substituted or 2,3-disubstituted)-(5-aminoalkyl)-2,5-diazacyclic compounds and related cyclic amino amides and cyclic keto diamines of Formula I, hereinafter, and further provides combinatorial libraries that contain those compounds. The naming system used herein is understood to not be in conformance with naming systems usually used in organic chemistry, and relies upon the structural features common to all of the contemplated compounds as is discussed below.

It is first to be noted that the contemplated compounds can have one of two structure types that each contain a cyclic compound in which two nitrogen atoms are present in the ring at what can be considered positions 1 and 4. The first compound type contains one or two carbonyl groups that can be bonded to a ring amine, in which the first amine contains another amine at the 2- through 7-position of an alkyl group bonded to that first amine, and in which the second amine also can also contain a substituent group. The second compound type contains the same structural features as the first type, but lacks the one or two carbonyl groups and is a cyclic compound containing two nitrogen atoms at positions 1 and 4 of the ring.

The numbering system used for these ring compounds begins with one of the carbonyl groups (when present) and continues around the ring to the second carbonyl group (when present) via the two ring nitrogen atoms so the ring nitrogen atoms have the same relative position numbers for all of the compounds embraced by Formula I. Thus, for a ring containing eight atoms and two amido carbonyls, the carbonyl groups are generically numbered to be at the 1- and 6-positions of the ring. The carbonyl groups and their amido nitrogen atoms of those compounds have the same numbers when the ring contains six atoms as in a diketopiperazine compound, even though the carbonyl groups of such a compound are assigned the 2- and 3-positions in a more usual system of nomenclature. Usual organic naming rules are followed for specific compounds or libraries such as the 1,4,5-trisubstituted-2,3-diketopiperazines discussed in the examples.

A first of the ring nitrogen atoms of a compound of Formula I, below, is bonded to a $C_1$–$C_7$ alkyl group that contains an amine substituent at the 2-through 7-position from that first amine. For the two carbonyl group-containing compounds, that first ring nitrogen is at ring position 5. For the corresponding compounds lacking the two carbonyl groups, that same nitrogen is at the 4-position of the ring. The second ring nitrogen can also be bonded to a substituent group. Using the above numbering system for the two carbonyl group-containing compounds, the second amine is at the 2-position for the group of compounds having the carbonyl groups and is at the 1-position for those compounds without the carbonyl groups. Compounds also typically contain a ring substituent at the 3-position of a dicarbonyl compound and at the 2-position of a cyclic diamine.

Exemplary structural formulas of some particularly preferred contemplated compounds are provided below based on structural Formulas II or III, hereinafter. Those formulas show the numbering system that is generally used, and in which q is one, and $R^{a1}$ and $R^{a2}$ and $R^{b1}$ and $R^{b2}$ are all hydrido and x and y are both one so that the ring positions are more easily seen.

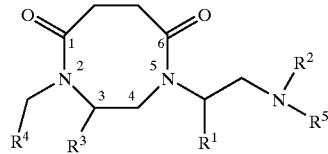

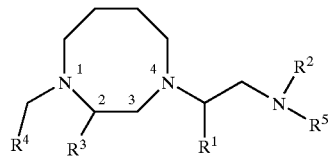

More specifically, the present invention contemplates individual compounds and synthetic combinatorial libraries of those compounds in which the compounds have a structure corresponding to that shown in Formula I, below, or a pharmaceutically acceptable salt thereof:

I wherein:

q is an integer having a value of 1–7;

W is a saturated or unsaturated chain of 2–4 carbon atoms that are bonded at each terminus of the chain to the depicted nitrogen atoms, wherein (1) zero, one or two of those carbon atoms of the chain is doubly bonded to an oxygen atom, (2)(a) each of the remaining carbon atoms of the chain is independently bonded to one or two substituents selected from the group consisting of a hydrogen atom (hydrido), $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group or (b) two of those remaining carbon atoms of the chain form a saturated or unsaturated mono- or bicyclic ring containing 5- to 8-members in each ring and zero to three heteroatoms in each ring that are independently oxygen, nitrogen or sulfur.

$R^1$ is selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group.

$R^2$ is selected from the group consisting of a $C_1$–$C_{10}$ alkyl, $C_2$–$C_{10}$ alkenyl, benzyl, substituted benzyl, naphthyl, or substituted naphthyl group and preferably is a methyl, ethyl, benzyl, allyl, or naphthylmethyl group, and more preferably is a 2-naphthylmethyl group. $R^2$ is most preferably a methyl or benzyl group.

$R^3$ is selected from the group consisting of a hydrogen atom (hydrido), $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group.

$R^4$ is selected from the group consisting of a hydrido, $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenyl-alkenyl group.

$R^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

Another aspect of the invention contemplates individual compounds and synthetic combinatorial libraries of those compounds in which the compounds have a structure corresponding to that shown in Formula II, below, or a pharmaceutically acceptable salt thereof:

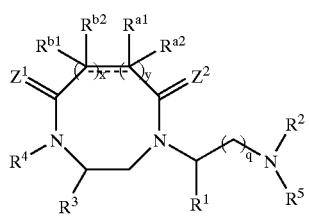

II wherein:
each of $=Z^1$ and $=Z^2$ is independently $=O$, or $=Z^1$ is —$R^{c1}$ and —$R^{c2}$ and $=Z^2$ is —$R^{c3}$ and —$R^{c4}$, wherein —$R^{c1}$, —$R^{c2}$, —$R^{c3}$ and —$R^{c4}$ are independently selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group.

x and y are independently zero or one, and the sum of x+y is zero, one or two.

q is an integer 1–7.

The dotted line between the carbon atom of $R^{a1}$ and $R^{a2}$, the carbon atom of $R^{b1}$ and $Rb^2$ indicates the presence or absence (i.e., the possibility) of one additional bond between those depicted carbon atoms.

(a) $R^{a1}$, $R^{a2}$, $R^{b1}$ and $R^{b2}$ are independently selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group or (b) each of $R^{a1}$ and $R^{b1}$ is also bonded to the same saturated or unsaturated mono- or bicyclic ring containing 5- to 8-members in each ring and zero to three heteroatoms in each ring that are independently oxygen, nitrogen or sulfur, or (c) one or both of $R^{a1}$ and $R^{a2}$ and $R^{b1}$ and $R^{b2}$ together are $=O$, and wherein both of $R^{a2}$ and $R^{b2}$ are absent when a double bond is present between the carbon atoms bonded to $R^{a1}$ and $R^{b1}$.

Substituents $R^1$, $R^2$, $R^3$, $R^4$ and $R^5$ in Formula II are as described above for Formula I.

Another aspect of the invention contemplates individual compounds and synthetic combinatorial libraries of those compounds in which the compounds have a structure corresponding to that shown in Formula III, below, or a pharmaceutically acceptable salt thereof:

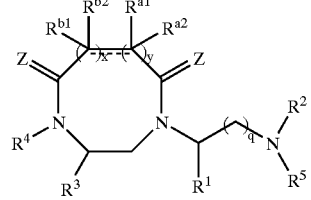

III wherein $=Z$ is $=O$ or $(—H)_2$, $R^{a2}$ and $R^{b2}$ are hydrido or are absent, q, the dotted line, x, y, $R^{a1}$, $R^{b1}$, $R^1$, $R^2$, $R^3$, $R^4$ and $R^5$ have the meanings provided above.

Compounds and libraries in which q is one, and x and y are both zero are particularly preferred. These compounds correspond in structure to Formulas E1 and E2, below, wherein $R^1$, $R^2$, $R^3$, $R^4$ and $R^5$ are as defined above.

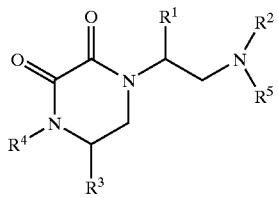

E1

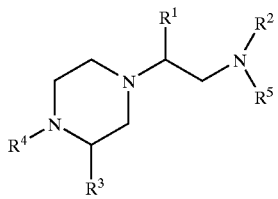

E2

$R^5$ is preferably hydrido in these compounds and libraries.

DETAILED DESCRIPTION OF THE INVENTION

The present invention relates to individual compounds and synthetic combinatorial libraries of those compounds, as well as the preparation and use of those compounds and libraries, in which the compounds have a structure corresponding to that shown in Formula I, below, or a pharmaceutically acceptable salt thereof:

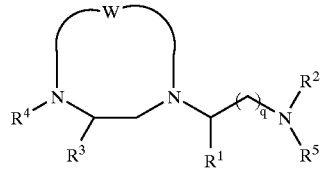

I wherein:
q is an integer that is 1 through 7. Thus, for example, there can be one through seven methylene groups between the carbon bonded to the $R^1$ group and the nitrogen bonded to $R^2$ and $R^5$.

W is a saturated or unsaturated chain of 2–4 carbon atoms that are bonded at each terminus of the chain to the depicted nitrogen atoms, wherein (1) zero, one or two of those carbon atoms of the chain is doubly bonded to an oxygen atom, (2) (a) the remaining carbon atoms of the chain are independently bonded to one or two substituents selected from the group consisting of a hydrogen atom (hydrido), $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group or (b) two of those remaining carbon atoms of the chain form a saturated or unsaturated mono- or bicyclic ring containing 5- to 8-members in each ring and zero to three heteroatoms in each ring that are independently oxygen, nitrogen or sulfur.

$R^1$ is selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group.

$R^2$ is selected from the group consisting of a $C_1$–$C_{10}$ alkyl, $C_2$–$C_{10}$ alkenyl, benzyl, substituted benzyl, naphthyl, or substituted naphthyl group and preferably is a methyl, ethyl, benzyl, allyl, or naphthylmethyl group. More preferably, $R^2$ is a 2-naphthylmethyl group, and $R^2$ is most preferably a methyl or benzyl group.

$R^3$ is selected from the group consisting of a hydrogen atom (hydrido), $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group.

$R^4$ is selected from the group consisting of a hydrido, $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenylalkenyl group.

$R^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

Looking more closely at W, it is seen that that group can contain a chain of two, three or four carbon atoms, each of which can be substituted as described hereinafter. The terminal carbons of the chain are each bonded to one of the nitrogen atoms shown in Formula I so that the compound or library of compounds contains at least one ring that can contain six, seven or eight atoms in the ring.

The carbon chain W can also contain no unsaturated bonds between the carbon atoms, or can contain one double bond, and therefore is saturated or unsaturated.

The carbon chain W can also contain zero, one or two carbonyl [C=O] groups. When present, it is preferred that the one or two carbonyl groups be arrayed symmetrically between the two depicted nitrogen atoms. Preferably, when two carbonyl groups are present, each is bonded to a nitrogen atom forming two amide groups. When only one carbonyl group is present, that carbonyl group can be part of an amide group or as a keto group.

A more specific aspect of the invention contemplates individual compounds and synthetic combinatorial libraries of those compounds and their pharmaceutically acceptable salts in which the compounds have a structure corresponding to that shown in Formula II, below, or a pharmaceutically acceptable salt thereof:

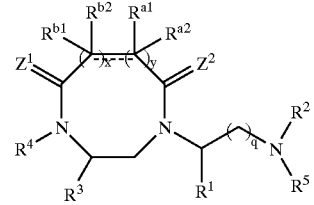

II wherein:
q is an integer that is one through seven;
each of $=Z^1$ and $=Z^2$ is independently $=O$ or $=Z^1$ is $—R^{c1}$ and $—R^{c2}$ and $=Z^2$ is $—R^{c3}$ and $—R^{c4}$, wherein $R^{c1}$, $—R^{c2}$, $—R^{c3}$ and $—R^{c4}$ are independently selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group;
x and y are independently zero or one, and the sum of x+y is zero, one or two;
the dotted line between the carbon atom of $R^{a1}$ and $R^{a2}$ and the carbon atom of $R^{b1}$ and $R^{b2}$ indicates the presence or absence of one additional bond between those depicted carbon atoms, so that when present, the additional bond is shown as a solid line, following usual conventions of organic chemistry, and $R^{a2}$ and $R^{b2}$ are absent;
(a) $R^{a1}$, $R^{a2}$, $R^{b1}$ and $R^{b2}$ are independently selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group or (b) each of $R^{a1}$ and $R^{b1}$ is also bonded to the same saturated or unsaturated mono- or bicyclic ring that contains 5- to 8-members in each ring and zero to three heteroatoms in each ring that are independently oxygen, nitrogen or sulfur, or (c) one or both of $R^{a1}$ and $R^{a2}$ and $R^{b1}$ and $R^{b2}$ together are $=O$, and wherein $R^{a2}$ and $R^{b2}$ are absent when a double bond is present between the depicted carbon atoms; and
substituents $R^1$, $R^2$, $R^3$, $R^4$ and $R^5$ in Formula II are as described above for Formula I.

In one embodiment of a compound or library of Formula II, either or both of $=Z^1$ and $=Z^2$ is $=O$, so that a carbonyl group is present. In other embodiments of a compound or library of Formula II, $=Z^1$ and $=Z^2$ are the enumerated substituents $—R^{c1}$ and $—R^{c2}$ for $=Z^1$ and $=Z^2$ is $—R^{c3}$ and $—R^{c4}$ for $=Z^2$.

In addition to the specific substituents $R^{a1}$, $R^{a2}$, $R^{b1}$ and $R^{b2}$ of some embodiments, in other embodiments, $R^{a2}$ and $R^{b2}$ are each hydrido and $R^{a1}$ and $R^{b1}$ are each also bonded to the same saturated or unsaturated mono or bicyclic ring. In this instance, at least two fused rings are present, one is the ring shown in the formula and the second is bonded to $R^{a1}$ and $R^{b1}$. That second ring can be monocyclic or bicyclic and can contain 5- to 8-members in each ring and zero to three heteroatoms in each ring that are independently oxygen, nitrogen or sulfur. Exemplary second rings include 1,2-cyclohexylidene, 1,2-cyclooctylidene, o-phenylene, 3,4-furanylidene, 2,3-pyrazinylidene, and 2,3-norbornenylidene. A double bond can also be present so that $R^{a2}$ and $R^{b2}$ are both absent.

Another aspect of the invention contemplates individual compounds and synthetic combinatorial libraries of those compounds and their pharmaceutically acceptable salts in which the compounds have a structure corresponding to that shown in Formula III, below, or a pharmaceutically acceptable salt thereof:

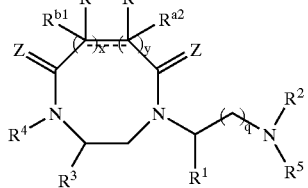

III wherein:
q is an integer having a value of 1 through 7;
x and y are independently zero or one, and the sum of x+y is zero, one or two;
Z is an oxygen atom (=Z is =O) or two hydrido groups [=Z is (—H)$_2$];
the dotted line between the carbon atoms bonded to R$^a$ and R$^b$ groups indicates the presence or absence of one additional bond between those depicted carbon atoms, as before;

(a) R$^{a1}$ and R$^{b1}$ are independently selected from the group consisting of a hydrogen atom (hydrido), $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group or (b) R$^{a1}$ and R$^{b1}$ together with the depicted carbon atoms form a 5- to 8-membered saturated or unsaturated ring that contains zero to three heteroatoms that are independently oxygen, nitrogen or sulfur, and wherein R$^{a2}$ and R$^{b2}$ are are hydrido or are absent when a double bond is present between the depicted carbon atoms;

R$^1$ is selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group;

R$^2$ is selected from the group consisting of a $C_1$–$C_{10}$ alkyl, $C_2$–$C_{10}$ alkenyl, benzyl, substituted benzyl, naphthyl, or substituted naphthyl group and preferably is a methyl, ethyl, benzyl, allyl, or naphthylmethyl group. More preferably, R$^2$ is a 2-naphthylmethyl group, and R$^2$ is most preferably a methyl or benzyl group;

R$^3$ is selected from the group consisting of a hydrido, $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

R$^4$ is selected from the group consisting of $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenyl-alkenyl group; and R$^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

The value of q is preferably one or two in each of the above Formulas, and is most preferably one. Exemplary compounds of each of those compound types of Formula I, and particularly for Formulas II and III, where q is one are shown below as Formulas IA, IIA and IIIA.

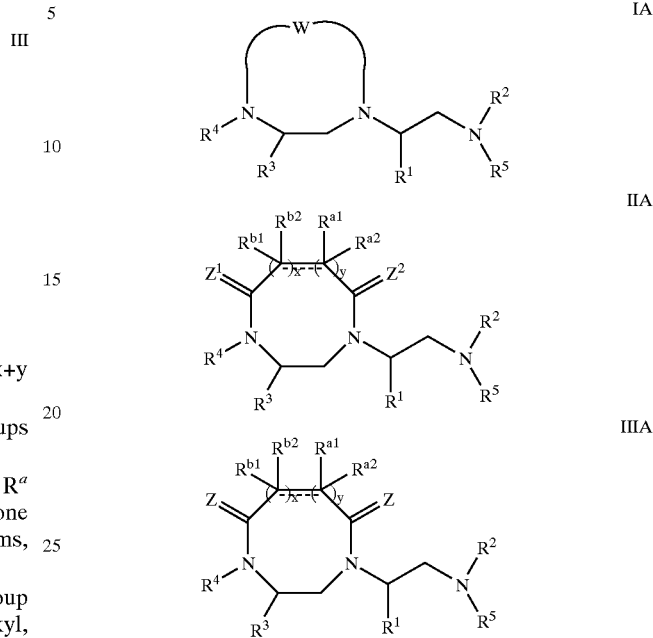

In some preferred embodiments of Formulas II and III, R$^{a2}$ and R$^{b2}$ substituents are both hydrido or are absent because a doubls bond is present. In those embodiments, a contemplated compound corresponds in structure to Formula IIB or IIIB, below.

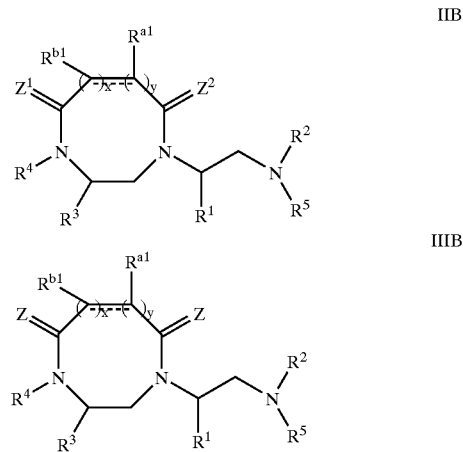

In some preferred embodiments of compounds and libraries of Formulas IIB and IIIB, x and y are both zero so that the resulting compound is a diketopiperazine derivative. In other preferred embodiments, x and y are both one and R$^{a2}$ and R$^{b2}$ together with the depicted carbon atoms form a bond (so that the compound is unsaturated); or x and y are both one, R$^{a2}$ and R$^{b2}$ are absent and a double bond is present or are both hydrido, and each of R$^{a1}$ and R$^{b1}$ is bonded to the same saturated or unsaturated mono- or bicyclic ring containing 5- to 8-members in each ring and zero to three heteroatoms in each ring that are independently oxygen, nitrogen.

It is preferred that R$^{a1}$ and R$^{b1}$, when present as individual substituents, both be identical to minimize the presence of isomers. It is similarly preferred when $R^{a1}$ and $R^{b1}$ are present as bonds to a saturated or unsaturated carbocyclic or heterocyclic ring substituent that that substituent ring be symmetrically placed between the two ring nitrogen atoms.

In addition, the carbon atoms to which the $R^{a1}$ and $R^{b1}$ groups are individually bonded can be bonded to each other via a single or double bond. Those two types of bonding are depicted in Formulas II and III by a single solid line, representing the single bond that must be minimally present, and one dotted line that represents another bond that can be present. Thus, with the remainder of the molecule represented by wavy lines, and $R^{a2}$ and $R^{b2}$ groups being hydrido and not shown or absent due to the presence of the double bond, the two contemplated bonds are

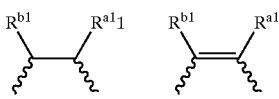

Exemplary compounds that are contemplated are illustrated below by the following structural Formulas B1 and B2 through U1 and U2, wherein $R^{a2}$ and $R^{b2}$ are both hydrido or are absent, $R^{a1}$ and $R^{b1}$ are a before-described substituent or together form a ring structure and the other R groups are as described before.

B1

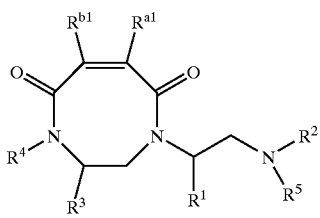

B2

C1

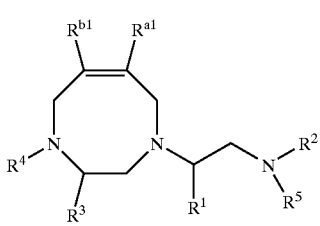

C2

D1

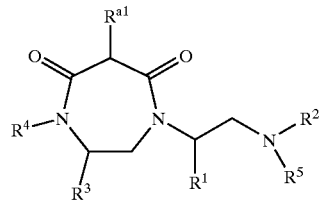

D2

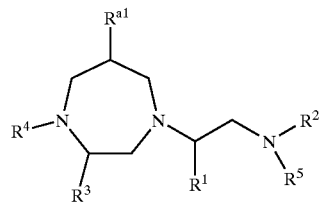

E1

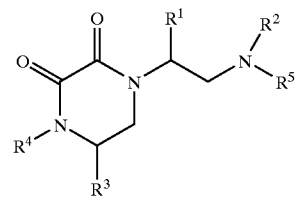

E2

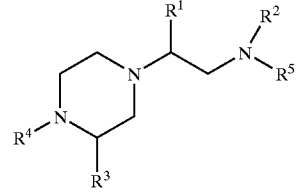

F1

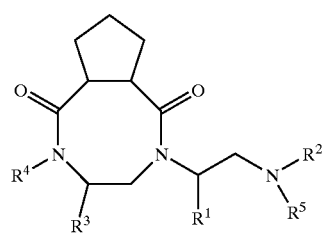

F2

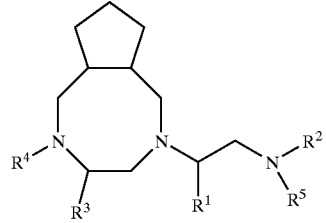

G1

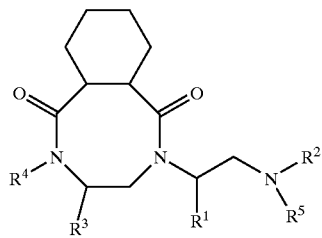

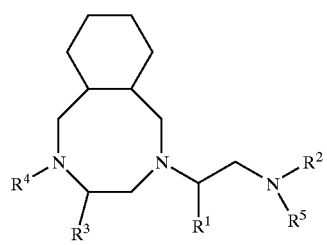
G2
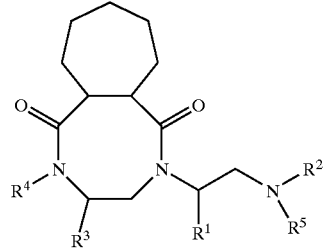
H1
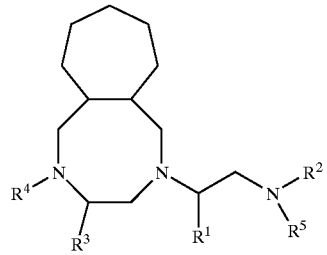
H2
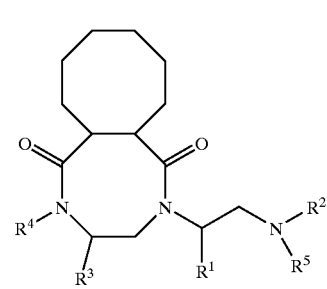
I1
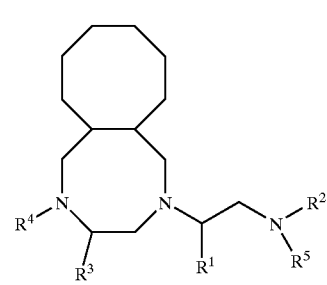
I2
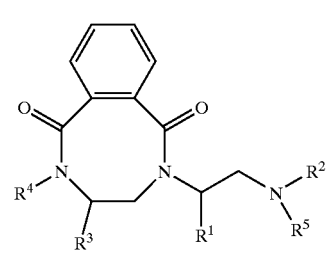
J1
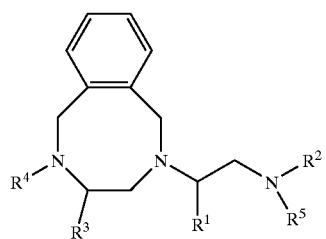
J2
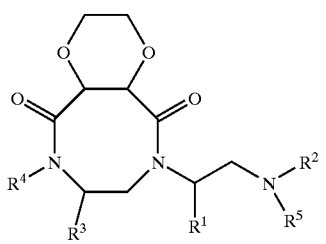
K1
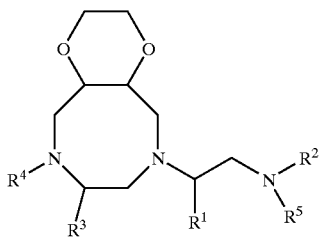
K2
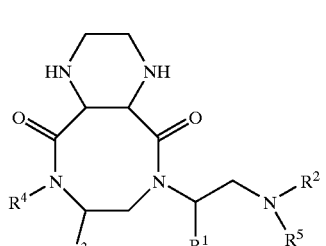
L1
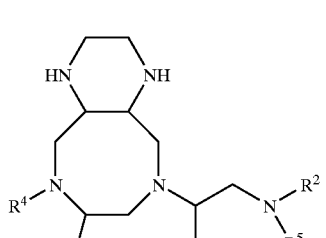
L2
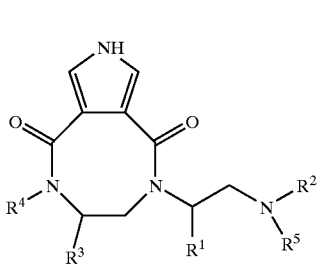
M1

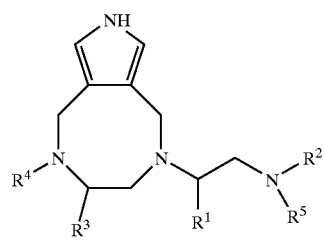
M2
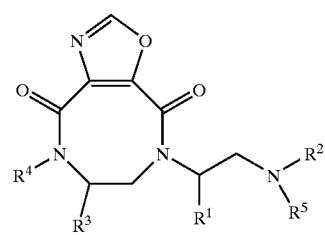
N1
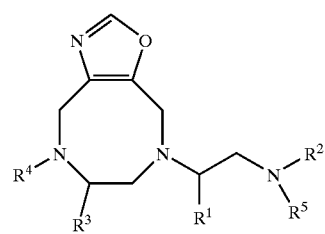
N2
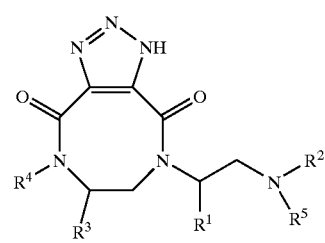
O1
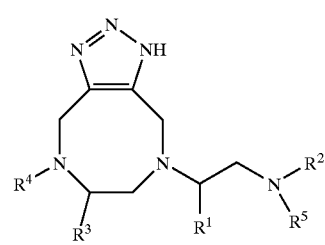
O2
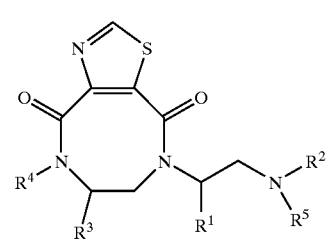
P1
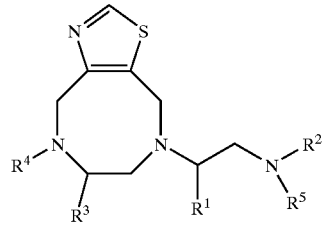
P2
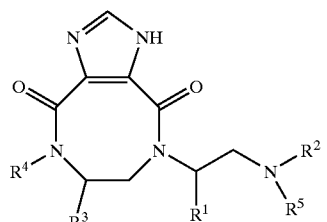
Q1
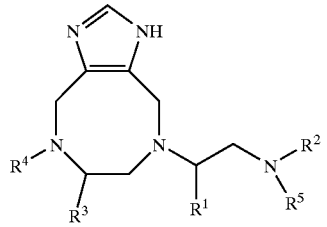
Q2
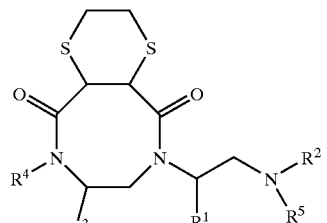
R1
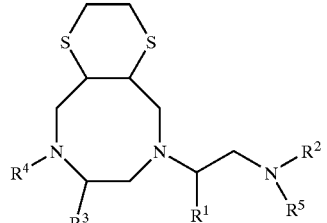
R2
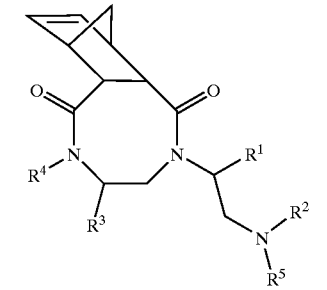
S1

-continued

S2
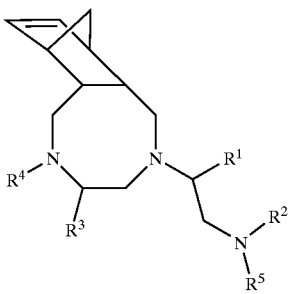

T1
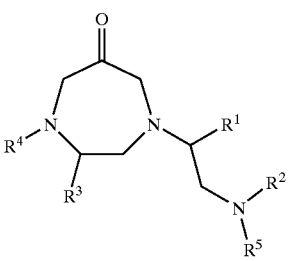

T2
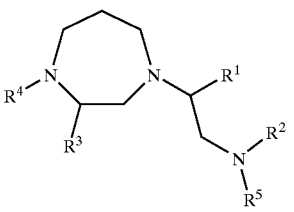

U1
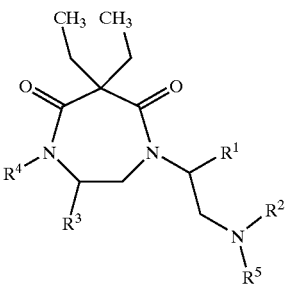

U2
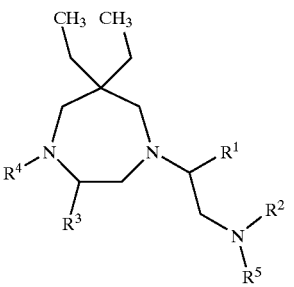

In one embodiment of the above compounds and libraries, R¹ is selected from the group consisting of a hydrido, methyl, benzyl, 2-butyl, N,N-dimethylaminobutyl, N-methylaminobutyl, N-methyl,N-benzyl aminobutyl, 2-methylpropyl, methylsulfinylethyl, methylthioethyl, N,N-dimethylaminoethyl, N,N-dimethylaminopropyl, N',N',N'-trimethylguanidinopropyl, N',N',N'-tribenzylguanidinopropyl, N,N -dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent;

R² is selected from the group consisting of a hydrido, methyl, ethyl, allyl, benzyl, or a 2-naphthylmethyl substituent;

R³ is selected from the grop consisting of a hydrido, methyl, benzyl, 3-hydroxypropyl, 2-butyl, N-methylaminobutyl, aminobutyl, 2-methylpropyl, methylsulfinylethyl, guanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent;

R⁴ is is selected from the group consisting of a 1-phenyl-1-cyclopropylmethyl, 2-phenylbutyl, 3-phenylbutyl, m-tolylethyl, 3-fluorophenethyl, 3-bromophenethyl, (α,α,α-trifluoro-m-tolyl)ethyl, p-tolylethyl, 4-fluorophenethyl, 3-methoxyphenethyl, 4-bromophenethyl, 4-methoxyphenethyl, 4-ethoxyphenethyl, 4-isobutyl-α-methylphenethyl, 3,4-dichlorophenethyl, 3,5-bis(trifluoromethyl)phenethyl, 3-(3,4-dimethoxyphenyl)propyl, 4-biphenethyl, 3-phenyl-2-methyl-2-propenyl, 3-(2-trifluoro-methylphenyl)-2-propenyl, 3,4-dimethoxyphenethyl, 3,4-(dihydroxy)phenylethyl, 3-(2-methoxyphenyl)-2-propenyl, benzyl, 3-(4-chlorophenyl)-2-propenyl, trans-phenyl-2-propenyl, m-xylyl, phenethyl, 3-phenylpropyl, 4-phenylbutyl, 3,5-bis-(trifluoromethyl)benzyl, butyl, heptyl, isobutyryl, (+/−)-2-methylbutyl, isovaleryl, 3-methylvaleryl, 4-methylvaleryl, 2-butenyl, 3-butenyl, p-xylyl, neopentyl, tert-butylethyl, cyclohexylmethyl, cyclohexylethyl, cyclohexylbutyl, cycloheptylmethyl, ethyl, 2-methyl-1-cyclopropyl-methyl, cyclobutyl-methyl, cyclopentylmethyl, 3-cyclopentylpropyl, cyclohexanepropyl, 4-methyl-1-cyclohexylmethyl, 4-tert-butyl-1-cyclohexylmethyl, 4-methyl-cyclohexylethyl, 2-methyl-2-butenyl, 1-adamantylethyl, 2-(α,α,α-trifluoro-m-toluidino)-3-pyridylmethyl, 4-nitrophenethyl, 4-(nitrophenyl)-butyl, 3-(4-nitrophenyl)-2-propenyl, 2-nitrobenzyl, 2,4-dinitrophenethyl, 4-biphenethyl, 2-chloro-5-nitrobenzyl, (4-pyridylthio)ethyl, 3,3-diphenylpropyl, 2-chloro-4-nitrobenzyl, 4-dimethylaminobenzyl, 4-nitrobenzyl, 3-dimethylamino-benzyl, abietyl, 2-methyl-4-nitro-1-imidizolylpropyl, trans-styrylethyl, cyclopentylethyl, 2,2-dicyclohexylethyl, (2-pyridylthio)ethyl, pentadienyl, 3-indolylethyl, 1-naphthylethyl, 3-(3,4,5-trimethoxyphenyl)propyl, 2-norbornylethyl, cyclopentylethyl, and a 2-ethylbutyl substituent; and R⁵ is a hydrido group, or an acyl group of a carboxylic acid selected from the group consisting of 1-phenyl-1-cyclopropane carboxylic acid, m-tolylacetic acid, 3-fluorophenylacetic acid, (α,α,α)trifluoro-m-tolylacetic acid, p-tolylacetic acid, 3-methoxyphenylacetic acid, 4-methoxyphenyl-acetic acid, 4-ethoxyphenylacetic acid, 4-isobutyl-α-methylphenylacetic acid, 3,4-dichloro-phenylacetic acid, 3,5-bis(trifluoromethyl)phenylacetic acid, phenylacetic acid, hydrocinnamic acid, 4-phenyl-butyric acid, formic acid, acetic acid, propionic acid, butyric acid, heptanoic acid, isobutyric acid, isovaleric acid, 4-methylvaleric acid, trimethylacetic acid, tert-butylacetic acid, cyclohexanecarboxylic acid, cyclohexylacetic acid, cyclohexanebutyric acid, cycloheptanecarboxylic acid, acetic acid, cyclobutanecarboxylic acid, cyclopentanecarboxylic acid, cyclohexanepropionic acid, 4-methyl-1-cyclohexanecarboxylic acid, 4-tert-butyl-cyclohexanecarboxylic acid, 1-adamantaneacetic acid, 3,3-diphenylpropionic acid, dicyclohexylacetic acid, indole-3-acetic acid, 1-naphthylacetic acid, 3-(3,4,5)-trimethoxyphenylpropionic acid, 2-norbornaneacetic acid, cyclopentylacetic acid, and 2-ethylbutyric acid.

In one of the preferred embodiments of the present invention of Formula III, where x and y are both zero, and q is one, R groups are those defined immediately below:

$R^1$ is selected from the group consisting of a hydrido, methyl, benzyl, 2-butyl, N,N-dimethylaminobutyl, N-methylaminobutyl, 2-methylpropyl, methylsulfinylethyl, methylthioethyl, hydroxymethyl, 1-hydroxyethyl, 2-propyl, 4-hydroxybenzyl, propyl, butyl, cyclohexylmethyl, phenyl, and a 2-naphthylmethyl substituent;

$R^2$ is methyl;

$R^3$ is selected from the group consisting of a hydrido, methyl, benzyl, 3-hydroxypropyl, 2-butyl, 2-methylpropyl, methylsulfinylethyl, methylthioethyl, hydroxymethyl, 1-hydroxyethyl, 2-propyl,4-hydroxybenzyl, propyl, butyl, cyclohexylmethyl, phenyl, and a 2-naphthylmethyl substituent;

$R^4$ is selected from the group consisting of a 1-phenyl-1-cyclopropylmethyl, m-tolylethyl, 3-fluorophenethyl, (α,α,α-trifluoro-m-tolyl)ethyl, p-tolylethyl, 3-methoxyphenethyl, 4-methoxyphenethyl, 4-ethoxyphenethyl, 4-isobutyl-α-methylphenethyl, 3,4-dichlorophenethyl, 3,5-bis(trifluoromethyl) phenethyl, phenethyl, 3-phenylpropyl, 4-phenylbutyl, butyl, heptyl, isobutyryl, isovaleryl, 4-methylvaleryl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, cyclohexanepropyl, 4-methyl-1-cyclohexylmethyl, 4-tert-butyl-1-cyclohexylmethyl, 4-methylcyclohexylethyl, 1-adamantylethyl, 3,3-diphenylpropyl, cyclopentylethyl, 2,2-dicyclohexylethyl, 2-indol-3-ylethyl, 1-naphthylethyl, 3-(3,4,5-trimethoxyphenyl)-propyl, 2-norbornylethyl, cyclopentylethyl, a 2-ethylbutyl substituent; and $R^5$ is hydrido.

In another of the preferred embodiment of the present invention of Formula III, where x and y are both zero, and q is one, R groups are those defined immediately below:

$R^1$ is selected from the group consisting of a hydrido, methyl, benzyl, 2-butyl, N-methyl,N-benzylaminobutyl, N-methylaminobutyl, 2-methylpropyl, methylsulfinylethyl, methylthioethyl, hydroxymethyl, 1-hydroxyethyl, 2-propyl, 4-hydroxybenzyl, propyl, butyl, cyclohexylmethyl, phenyl, and a 2-naphthylmethyl substituent;

$R^2$ is benzyl;

$R^3$ is selected from the group consisting of a hydrido, methyl, benzyl, 3-hydroxypropyl, 2-butyl, 2-methylpropyl, methylsulfinylethyl, methylthioethyl, hydroxymethyl, 1-hydroxyethyl, 2-propyl,4-hydroxybenzyl, propyl, butyl, cyclohexylmethyl, phenyl, and a 2-naphthylmethyl substituent;

$R^4$ is selected from the group consisting of a 1-phenyl-1-cyclopropylmethyl, m-tolylethyl, 3-fluorophenethyl, (α,α,α-trifluoro-m-tolyl)ethyl, p-tolylethyl, 3-methoxyphenethyl, 4-methoxyphenethyl, 4-ethoxyphenethyl, 4-isobutyl-α-methylphenethyl, 3,4-dichlorophenethyl, 3,5-bis(trifluoromethyl) phenethyl, phenethyl, 3-phenylpropyl, 4-phenylbutyl, butyl, heptyl, isobutyryl, isovaleryl, 4-methylvaleryl, cyclohexylmethyl, cyclohexylethyl, cyclohexylbutyl, cycloheptylmethyl, ethyl, 2-methyl-1-cyclopropylmethyl, cyclobutylmethyl, cyclopentylmethyl, cyclohexanepropyl, 4-methyl-1-cyclohexylmethyl, 4-tert-butyl-1-cyclohexylmethyl, 4-methylcyclohexylethyl, 1-adamantylethyl, 3,3-diphenylpropyl, cyclopentylethyl, 2,2-dicyclohexylethyl, 2-indol-3-ylethyl, 1-naphthylethyl, 3-(3,4,5-trimethoxy-phenyl)-propyl, 2-norbornylethyl, cyclopentylethyl, and a 2-ethylbutyl substituent; and $R^5$ is hydrido.

In any of the above Formulas or other formulas herein, the stereochemistry of the chiral $R^1$ and $R^3$ groups can independently be in the R or S configuration, or a mixture of the two. For instance, as will be described in further detail below the $R^1$ and $R^3$ groups can be the side chains of the α-carbon of various amino acid residues. The amino acid residues can be in the L-or D-configuration, resulting in the same substituent group, R, varying only in its stereochemistry. In addition, contemplated compounds can be present as diastereomers, as in the compounds of Formulas D1 and D2, in which case both isomers are contemplated.

In any of the Formulas herein, the term "$C_1$–$C_{10}$ alkyl" denotes a radical such as a methyl, ethyl, n-propyl, isopropyl, n-butyl, sec-butyl, tert-butyl, amyl, tert-amyl, hexyl, heptyl, decyl group and the like. The term "loweralkyl" denotes a $C_1$–$C_4$ alkyl group. A preferred "$C_1$–$C_{10}$ alkyl" group is a methyl group.

The term "$C_2$–$C_{10}$ alkenyl" denotes a radical such as a vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and decenyl group and the like, as well as dienes and trienes of straight and branched chains containing up to ten carbon atoms and at least one carbon-to-carbon (ethylenic) double bond.

The term "$C_2$–$C_{10}$ alkynyl" denotes a radical such as ethynyl, propynyl, butynyl, pentynyl, hexynyl, heptynyl, decynyl and the like, as well as di- and triynes of straight and branched chains containing up to ten carbon atoms and at least one carbon-to-carbon (acetylenic) triple bond.

The term "$C_1$–$C_{10}$ substituted alkyl", "$C_2$–$C_{10}$ substituted alkenyl" and "$C_2$–$C_{10}$ substituted alkeynyl", denote that the above $C_1$–$C_{10}$ alkyl group and $C_2$–$C_{10}$ alkenyl and alkynyl groups are substituted by one or more, and preferably one or two, halogen, hydroxy, protected hydroxy, $C_3$–$C_7$ cycloalkyl, $C_3$–$C_7$ substituted cycloalkyl, naphthyl, substituted naphthyl, adamantyl, abietyl, thiofuranyl, indolyl, substituted indolyl, amino, protected amino, (monosubstituted) amino, protected (monosubstituted) amino, (disubstituted) amino, guanidino, (monosubstituted)guanidino, (disubstituted)guanidino, (trisubstituted)guanidino, imidazolyl pyrolidinyl, $C_1$–$C_7$ acyloxy, nitro, heterocycle, substituted heterocycle, $C_1$–$C_4$ alkyl ester, carboxy, protected carboxy, carbamoyl, carbamoyloxy, carboxamide, protected carboxamide, cyano, methylsulfonylamino, methylsulfonyl, sulfhydryl, $C_1$–$C_4$ alkylthio, $C_1$–$C_4$ alkyl sulfonyl or $C_1$–$C_4$ alkoxy groups. The substituted alkyl groups can be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcarbonylaminomethyl, carbamoyloxymethyl, methoxymethyl, ethoxymethyl, t-butoxymethyl, acetoxymethyl, chloromethyl, bromomethyl, iodomethyl, 6-hydroxy-hexyl, 2,4-dichloro(n-butyl), 2-amino (isopropyl), 2-carbamoyloxyethyl chloroethyl, bromoethyl, fluoroethyl, iodoethyl, chloropropyl, bromopropyl, fluoropropyl, iodopropyl and the like.

In preferred embodiments of the subject invention, $C_1$–$C_{10}$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, are more preferably $C_1$–$C_7$ or $C_2$–$C_7$, respectively, and more preferably, $C_1$–$C_6$ or $C_2$–$C_6$ as is appropriate for unsaturated substituents. However, it should be appreciated by those of skill in the art that one or a few carbons usually can be added to an alkyl, alkenyl, alkynyl, substituted or unsubstituted, without substantially modifying the structure and function of the subject compounds and that, therefore, such additions would not depart from the spirit of the invention.

The term "$C_1$–$C_4$ alkoxy" as used herein denotes groups that are ether groups containing up to four carbon atoms such as methoxy, ethoxy, n-propoxy, isopropoxy, n-butoxy, t-butoxy and like groups. A preferred $C_1$–$C_4$ alkoxy group is methoxy.

The term "$C_1$–$C_7$ acyloxy" denotes a carboxy group-containing substituent containing up seven carbon atoms such as formyloxy, acetoxy, propanoyloxy, butanoyloxy, pentanoyloxy, hexanoyloxy, heptanoyloxy, and the like.

Similarly, the term "$C_1$–$C_7$ acyl" encompasses groups such as formyl, acetyl, propionoyl, butyroyl, pentanoyl, hexanoyl, heptanoyl, benzoyl and the like.

The substituent term "$C_3$–$C_7$ cycloalkyl" includes the cyclopropyl, cyclobutyl, cyclopentyl, cyclohexyl or cycloheptyl rings. The substituent term "$C_3$–$C_7$ substituted cycloalkyl" indicates an above cycloalkyl ring substituted by a halogen, hydroxy, protected hydroxy, phenyl, substituted phenyl, heterocycle, substituted heterocycle, $C_1$–$C_{10}$ alkyl, $C_1$–$C_4$ alkoxy, carboxy, protected carboxy, amino, or protected amino.

The substituent term "$C_5$–$C_7$ cycloalkenyl" indicates a substituent that is itself a 1-, 2-, or 3-substituted cyclopentenyl ring, a 1-, 2- , 3- or 4-substituted cyclohexenyl ring or a 1-, 2-, 3-,4- or 5-substituted cycloheptenyl ring, whereas the term "substituted $C_3$–$C_7$ cycloalkenyl" denotes the above $C_3$–$C_7$ cycloalkenyl rings substituted by a $C_1$–$C_{10}$ alkyl radical, halogen, hydroxy, protected hydroxy, $C_1$–$C_4$ alkoxy, carboxy, protected carboxy, amino, or protected amino, The term "heterocyclic ring" or "heterocycle" denotes an optionally substituted 5-membered or 6-membered ring that has 1 to 4 heteroatoms, such as oxygen, sulfur and/or nitrogen, in particular nitrogen either alone or in conjunction with sulfur or oxygen ring atoms. These five-membered or six-membered rings can be fully unsaturated or partially unsaturated, with fully unsaturated rings being preferred.

Preferred heterocyclic rings include pyridino, pyrimidino, and pyrazino, furano, and thiofurano rings. The heterocyles can be substituted or unsubstituted as for example, with such substituents as those described in relation to substituted phenyl or substituted naphthyl.

The term "$C_7$–$C_{16}$ phenylalkyl", or "$C_7$–$C_{16}$ aralkyl" denotes a $C_1$–$C_{10}$ alkyl group substituted at any position by a phenyl ring. Examples of such a group include benzyl, 2-phenylethyl, 3-phenyl(n-prop-1-yl), 4-phenyl(hex-1-yl), 3-phenyl(n-am-2-yl), 3-phenyl(sec-butyl), and the like. A preferred $C_7$–$C_{16}$ phenylalkyl group is the benzyl group. The term "$C_7$–$C_{16}$ substituted phenylalkyl" denotes an above $C_7$–$C_{16}$ phenylalkyl group substituted on $C_1$–$C_{10}$ alkyl portion with one or more, and preferably one or two, groups chosen from halogen, hydroxy, protected hydroxy, keto, $C_2$–$C_3$ cyclic ketal phenyl, amino, protected amino, $C_1$–$C_7$ acyloxy, nitro, carboxy, protected carboxy, carbamoyl, carbarnoyloxy, cyano, N-(methylsulfonylamino) or $C_1$–$C_4$ alkoxy, whose phenyl group can be substituted with 1 or 2 groups selecterd from the group consisting of halogen, hydroxy, protected hydroxy, nitro, $C_1$–$C_{10}$ alkyl, $C_1$–$C_6$ substituted alkyl, $C_1$–$C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, a N-(methylsulfonylamino) group, or a phenyl group that is itself substituted or unsubstituted. When either the $C_1$–$C_{10}$ alkyl portion or the phenyl portion or both are mono- or di-substituted, the substituents can be the same or different.

Examples of "$C_7$–$C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethyl-phenyl)-3-(aminomethyl)(n-pent-2-yl), 5-phenyl-3-keto-(n-pent-1-yl), 4-(4-aminophenyl)-4-(I.4-oxetanyl)(n-but-1-yl), and the like.

The term "$C_7$–$C_16$ phenylalkenyl". denotes a $C_1$–$C_{10}$ alkenyl group substituted at any position by a phenyl ring. The term "$C_7$–$C_{16}$ substituted phenylalkenyll" denotes a $C_7$–$C_{16}$ arylalkenyl group substituted on the $C_1$–$C_{10}$ alkenyl portion. Substituents can the same as those as defined above in relation to $C_7$–$C_16$ phenylalkyl and $C_7$–$C_{16}$ substituted phenylalkyl. A preferred $C_7$–$C_{16}$ substituted phenylalkenyl is 3-(4-nitrophenyl)-2-propenyl. The term "substituted phenyl" specifies a phenyl group substituted at one or more positions, preferably at one or two positions, with moieties selected from the group consisting of halogen, hydroxy, protected hydroxy, cyano, nitro, $C_1$–$C_{10}$ alkyl, $C_1$–$C_{10}$ substituted alkyl, $C_1$–$C_4$ alkoxy, carboxy, protected carboxy, carboxymethyl, protected carboxymethyl, hydroxymethyl, protected hydroxymethyl, amino, protected anlino, (moaosubstituted)amino, protected (monosubstituted) amino, (disubstituted)amino, trifluoromethyl, N-(methylsulfonylamino), or phenyl that is itself substituted or unsubstituted.

Illustrative substituents embraced by the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected hydroxy derivatives thereof and the like; a nitrophenyl group such as 3-or 4-nitrophenyl, a cyanophenyl group for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-prop-1-yl)phenyl and the like: a mono or di(alkoxyl)phenyl, group for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methyl-phenoxy)phenyl, and the like; 3-or 4-trifluoromethylphenyl; a mono- or dicarboxyphenyl or (protected carboxy)phenyl group such as 4-carboxyphenyl or 2,4-di (protected carboxy)phenyl; a mono-or di(hydroxymethyl) phenyl or (protected hydroxymethyl)phenyl such as 3-(protected hydroxymethyl)phenyl or 3,4-di (hydroxymethyl)phenyl; a mono- or di(aminomethyl) phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different. For example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like are contemplated.

The term "substituted naphthyl" specifies a naphthyl group substituted with one or more, and preferably one or two moieties selected from the group consisting of halogen, hydroxy, protected hydroxy, cyano, nitro, $C_1$–$C_{10}$ alkyl, $C_1$–$C_4$ alkoxy, carboxy, protected carboxy, carboxymethyl, protected carboxymethyl, hydroxymethyl, protected hydroxymethyl, amino, protected amino, (monosubstituted) amino, protected (monosubsticuted)amino, (disubstituted) amino trifluoromethyl, or N-(methylsulfonylamino). Examples of substituted naphthyl include 2-(methoxy) naphthyl and 4-(methoxy)naphthyl.

The term "substituted indolyl" specifies a indolyl group substituted, either at the nitrogen or carbon, or both, with one or more, and preferably one or two, moieties selected from the group consisting of halogen, hydroxy, protected hydroxy, cyano, nitro, $C_1$–$C_{10}$ alkyl, $C_1$–$C_{10}$ substituted alkyl, $C_1$–$C_{10}$ alkenyl, $C_7$–$C_{16}$ phenylalkyl, $C_7$–$C_{16}$ substituted phenylalkyl, $C_1$–$C_6$ alkoxy, carboxy, protected carboxy, carboxymethyl, protected carboxymethyl, hydroxymethyl, protected hydroxymethyl, amino, protected amino, monosubstituted amino, or disubstituted amino.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napthylmethyl, and the like. An example of a disubstituted indolyl is 1-methyl-5-methyl indolyl.

The terms "halo" and "halogen" refer to the fluoro, chloro, bromo, or iodo groups.

The term "(monosubstituted)amino refers to an amino group with one substituent selected from the group consisting of phenyl, substituted phenyl, $C_1$–$C_{10}$ alkyl, and $C_7$–$C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents selected from the group consisting of phenyl, substituted phenyl, $C_1$–$C_{10}$ alkyl, and $C_7$–$C_{16}$ arylalkyl wherein the latter three substituent terms are as described above. The two substituents can be the same or different.

The terms "(monosubstituted)guanidino, "(disubstituted) guanidino." and "(trisubstituted)-guanidino" are used to mean that a guanidino group is substituted with one, two, or three substituents, respectively. The substituents can be any of those as defined above in relation to (monosubstituted)-amino and (disubstituted)amino and, where more than one substituent is present, the substituents can be the same or different The term "amino-protecting group" as used herein refers to one or more selectively removable substituents on the amino group commonly employed to block or protect the amino functionality. The term "protected (monosubstituted) amino" means there is an amino-protecting group on the monosubstituted amino nitrogen atom. In addition, the term "protected carboxamide" means there is an amino-protecting group present replacing the proton of the amido nitrogen so that there is no N-aLkylation. Examples of such amino-protecting groups include the formyl ("For") group, the trityl group (Trt), the phthalimido group, the trichloroacetyl group, the chloroacetyl, bromoacetyl, and iodoacetyl groups. Urethane blocking groups, such as t-butoxycarbonyl ("BoC"), 2-(4-biphenylyl)propyl(2)oxycarbonyl ("Bpoc"), 2-phenylpropyl(2)oxycarbonyl ("Poc"), 2-(4-xenyl)isopropoxycarbonyl, 1,1-diphenylethyl(1) oxycarbonyl, 1.1-diphenylpropyl(1)oxycarbonyl, 2-(3,5-dimethoxyphenyl) propyl(2)oxycarbonyl ("Ddz"), 2-(p-5 toluyl)propyl(2)oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2) propoxycarbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like, the benzoylmethylsulfonyl group, dithiasuccinoyl ("Dts') group, the 2-(nitro)phenylsulfenyl group ("Nps'), the diphenylphosphine oxide group, and like amino-protecting groups. The species of amino-protecting group employed is usually not critical so long as the derivatized amino group is stable to the conditions of the subsequent reactions and can be removed at the appropriate point without disrupting the remainder of the compound Preferred amino-protecting groups are Boc and Fmoc.

Further examples of amino-protecting groups embraced to by the above term are well known in organic synthesis and the peptide art and are described by, for example. T. W. Greene and P. G. M. Wuts. *Protective Groups in Organic Synthesis,*" 2nd ed., John Wiley and Sons. New York. N.Y., Chapter 7, 1991. M. Bodanzsky. *Principles of Pertide Synthesis.* 1st and 2nd revised ed., Springer-Verlag, New York, N.Y., 1984 and 1993, and Stewart and Young. Solid Phase Peptide Synthesis, 2nd ed., Pierce Chemical Co, Rockford. Ill. 1984.

The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-methoxytrityl, 4,41,4"-trimethoxytrityl, 2-phenylprop-2-yl, trimethylsilyl, t-butyldimethylsilyl, 2,2,2-trichloroethyl, β-(trimethylsilyl)

ethyl, β-[di(n-butyl)-methylsilyl]ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is also usually not critical so long as the derivatized carboxylic acid is stable to the conditions of subsequent reactions and can be removed at the appropriate point without disrupting the remainder of the molecule.

Further examples of these groups, are found in E. Haslam, *Protective Groups in Organic Chemistry*, J. G. W. McOmie Ed., Plenum Press, New York, N.Y. Chapter 5, 1973, and T. W. Greene and P. G. M. Wuts, *Protective Groups in Organic Synthesis*, 2nd ed., John Wiley and Sons, New York, N.Y., Chapter 5, 1991. A related term is "protected carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups, and the like. The species of hydroxy-protecting groups is also usually not critical so long as the derivatized hydroxyl group is stable to the conditions of subsequent reaction(s) and can be removed at the appropriate point without disrupting the remainder of the compound.

Further examples of hydroxy-protecting groups are described by C. B. Reese and E Haslam, *Protective Groups in Organic Chemistry*, J. G. W. McOmie Ed., Plenum Press, New York, N.Y., Chapters 3 and 4, 1973, and T. W. Greene and P. G. M. Wuts, *Protective Groups in Organic Synthesis*, 2nd ed., John Wiley and Sons, New York, N.Y., Chapters 2 and 3, 1991.

The substituent term "$C_1$–$C_4$ alkylthio" refers to sulfide groups such as methylthio, ethylthio, n-propylthio, isopropylthio, -butylthio, t-butylthio and like groups.

The substituent term "$C_1$–$C_4$ alkylsulfoxide" indicates sulfoxide groups such as methylsulfoxide, ethylsulfoxide, α-propylsulfoxide, iso-propylsulfoxide, n-butylsulfoxide, sec-butylsulfoxide, and the like.

The term "$C_1$–$C_4$ alkylsulfonyl" encompasses groups such as methylsulfonyl, ethylsulfonyl, n-propylsulfonyl, isopropylsulfonyl, α-butylsulfonyl, t-butylsulfonyl, and the like.

Phenylthio, phenyl sulfoxide, and phenylsulfonyl compounds are known in the art and these have their art-recognized definitions. By "substituted phenylthio", "substituted phenyl sulfoxide", and "substituted phenylsulfonyl" is meant that the phenyl can be substituted as described above in relation to "substituted phenyl."

The substituent terms "cyclic $C_2$–$C_{10}$ alkylene", "substituted cyclic $C_2$–$C_{10}$ alkylene", "cyclic $C_2$–$C_{10}$ heteroalkylene." and "substituted cyclic $C_2$–$C_{10}$ heteroakylene" defines a cyclic group bonded ("fused") to the phenyl radical. The cyclic group can be saturated or contain one or two double bonds. Furthermore, the cyclic group can have one or two methylene groups replaced by one or two oxygen, nitrogen or sulfur atoms.

The cyclic alkylene or heteroalkylene group can be substituted once or twice by substituents selected from the group consisting of hydroxy, protected hydroxy, carboxy, protected carboxy, keto, ketal, $C_1$–$C_4$ alkoxycarbonyl, $C_1$–$C_4$ alkanoyl, $C_1$–$C_{10}$ alkyl, carbamoyl, $C_1$–$C_4$ alkoxy, $C_1$–$C_4$, alkylthio, $C_1$–$C_4$ alkylsulfoxide, $C_1$–$C_4$ alkylsulfonyl, halo, amino, protected amino, hydroxymethyl and a protected hydroxymethyl group.

A cyclic alkylene or heteroalkylene group fused onto the benzene radical can contain two to ten ring members, but it preferably contains four to six members. Examples of such saturated cyclic groups include a bicyclic ring system that is a 2,3-dihydroindanyl or a tetralin ring. When the cyclic groups are unsaturated, examples occur when the resultant bicyclic ring system is a naphthyl ring or indanyl. An example of a cyclic group which can be fused to a phenyl radical that has two oxygen atoms and that is fully saturated is dioxanyl. Examples of fused cyclic groups that each contain one oxygen atom and one or two double bonds occur when the phenyl ring is fused to a furo, pyrano, dihydrofurano or dihydropyrano ring. Cyclic groups that each have one nitrogen atom and contain one or two double more double bonds are illustrated where the phenyl is fused to a pyridino or pyrano ring. An example of a fused ring system having one nitrogen and two phenyl radicals is a carbozyl group. Examples of cyclic groups that each have one sulfur atom and contain one or two double bonds occur where the benzene ring is fused to a thieno, thiopyrano, dihydrothieno, or dihydrothiopyrano ring. Examples of cyclic groups that contain two heteroatoms selected from sulfur and nitrogen and one or two double bonds occur where the phenyl ring is fused to a thiazolo, isothiazolo, dihydrothiazolo or dihydroisothiazolo ring. Examples of cyclic groups that contain two heteroatoms selected from oxygen and nitrogen and one or two double bonds occur where the benzene ring is fused to an oxazole, isoxazole, dihydroxazole or dihydroisoxazole ring. Examples of cyclic groups that contain two nitrogen heteroatoms and one or two double bonds occur where the benzene ring is fused to a pyrazolo, imidazolo, dihydropyrazolo or dihydroimidazolo ring.

One or more of the contemplated compounds within a given library can be present as a pharmaceutically-acceptable salt. The term "pharmaceutically-acceptable salt" encompasses those salts that form with carboxylate, phosphate or sulfonate anions and ammonium ions and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate, phosphate or sulfonate anion of a salt. The counter-ions are selected from the alkali and alkaline earth metals, (such as lithium, sodium, potassium, barium, magnesium and calcium) ammonium, and the organic cations such as dibenzylammonium, benzylammonium, 2-hydroxymethylammonium, bis(2-hydroxyethyl)ammonium, phenylethylbenzylammonium, dibebenzylethylene-diammonium, and like cations. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for a carboxylate anion is the sodium cation.

The compounds of an above Formula can also exist as solvates and hydrates. Thus, these compounds can crystalize with, for example, waters of hydration, or one, a number of, or any fraction thereof of molecules of the mother liquor solvent. The solvates and hydrates of such compounds are included within the scope of this invention.

One or more of the contemplated compounds can be in the biologically active ester form, such as the non-toxic, metabolically-labile ester-form. Such ester forms induce increased blood levels and prolong the efficacy of the corresponding non-esterified forms of the compounds. Ester groups that can be used include the lower alkoxymethyl groups ($C_1$–$C_4$ alkoxymethyl) for example, methoxymethyl, ethoxymethyl, isopropoxymethyl and the like; the α-($C_1$–$C_4$) alkoxyethyl groups, for example methoxyethyl, ethoxyethyl, propxyethyl, iso-propoxyethyl, and the like, the 2-oxo-1,3-dioxolen-4-ylmethyl groups such as 5-methyl-2-oxo-1,3-dioxolen-4-ylmethyl, 5-phenyl-2-oxo-1,3-dioxolen-4-ylmethyl, and the like, the $C_1$–$C_3$ alkylthiomethyl groups, for example methylthiomethyl, ethylthiomethyl, isopropylthiomethyl, and the like, the acyloxymethyl groups, for example pivaloyloxymethyl, pivaloyloxyethyl, α-acetoxymethyl, and the like, the ethoxycarbonyl-1-methyl group, the α-acetoxyethyl, the 3-phthalidyl or 5,6-dimethylphtalidyl groups, the 1-($C_1$–$C_4$ alkyloxycarbonyloxy)ethyl groups such as the 1-(ethoxycarbonyloxy)ethyl group, and the 1-($C_1$–$C_4$ alkylaminocarbonyloxy)ethyl groups such as the 1-methylaminocarbonyloxyethyl group.

As used herein, a chemical or combinatorial "library" is an intentionally created collection of differing molecules that can be prepared by the synthetic means provided below or otherwise herein and screened for biological activity in a variety of formats (e.g. libraries of soluble molecules). Libraries of compounds attached to resin beads, silica chips or other solid supports). The libraries can be screened in any variety of assays, such as those detailed below as well as others useful for assessing the biological activity of diketopiperazines. The libraries typically contain at least one active compound and are generally prepared in such that the compounds are in equimolar quantities.

Compound and Library Synthesis

As will be described in further detail, illustrative libraries were prepared, two trisubstituted diketopiperazines (one having $R^2$ as methyl and the other having $R^2$ as benzyl). The diketopiperazine libraries and compounds of Formula I can be prepared according to the general Reaction Scheme shown in Scheme 1, below, and discussed in greater detail hereinafter.

The compounds and libraries were prepared using solid-phase techniques. The solid-phase resin, here is p-methylbenzhydryl-amine resin (p-MBHA), is indicated in Scheme 1, below, by the large circle and dash. Compound preparation is illustrated first.

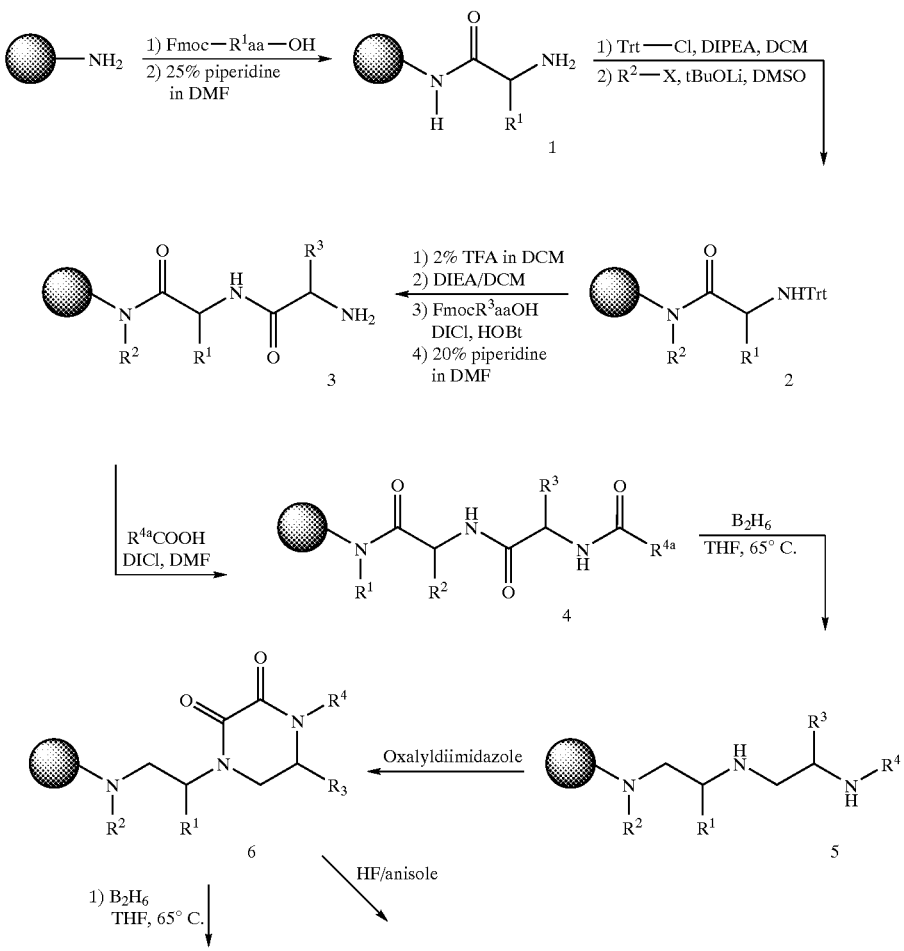

Scheme 1

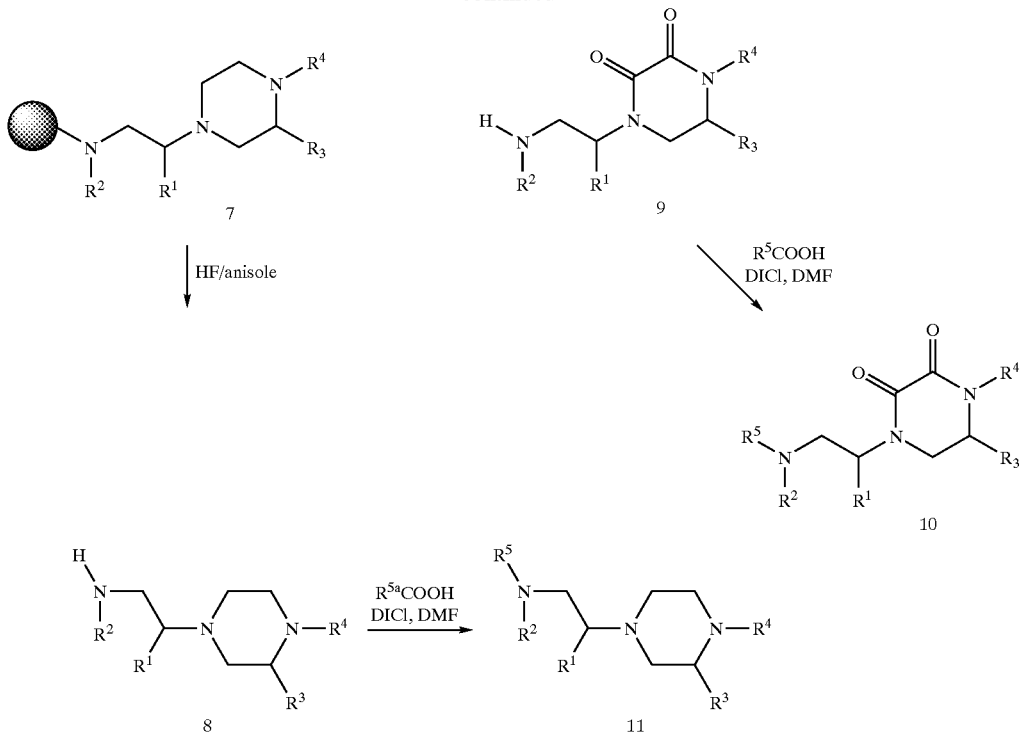

Starting from p-methylbenzhydrylamine (MBHA) resin-bound fluoroenylmethoxycarbonyl amino acid (Fmoc-$R^1$aa-OH), the Fmoc group was removed using a mixture of piperidine in dimethylformamide (DMF). The resulting amine, compound 1, was then protected with triphenylmethyl chloride (TrtCl). The secondary amide was then selectively alkylated in the presence of lithium t-butoxide and alkylating reagent, $R^2X$, in this instance methyl iodide or benzyl bromide to form the resin-bound N-alkylated compound 2. The Trt group was cleaved with a solution of 2% trifluoroacetic acid (TFA) and a second amino acid (Fmoc-$R^3$aa-OH) was coupled in presence of diisopropylcarbodiimide and hydroxybenzotriazole from which the Fmoc protecting group was removed to form the resin-bound dipeptide 3. The resin bound-dipeptide was N-acylated with a wide variety of carboxylic acids ($R^{4a}$COOH) to form the resin-bound N-acylated dipeptide 4. Exhaustive reduction of the amide bonds of the resin-bound N-acylated dipeptide 4 was achieved using borane in tetrahydrofuran as described, for instance, in Ostresh et al., *J. Org. Chem.*, 63:8622 (1998) and in Nefzi et al., Tetrahedron, 55:335 (1999). The resulting resin-bound polyamine 5 was then treated with oxalyldiimidazole in anhydrous DMF to form resin-bound diketopiperazine 6. Reaction of resin-bound compound 6 with anhydrous HF and anisole provided a desired diketopiperazine 9, which could be further N-acylated with a wide variety of carboxylic acids ($R^{5a}$COOH) to provide compound 10. Further reduction of resin-bound compound 6 with diborane in THF provided corresponding resin-bound piperazine compound 7. Reaction of compound 7 with anhydrous HF and anisole provided a desired free piperazine compound 8, which could be further N-acylated with a wide variety of carboxylic acids ($R^{5a}$COOH) as before to provide compound 11.

Following the strategy described in Scheme 1, with the parallel synthesis approach, commonly referred to as the "T-bag" method [Houghten et al., *Nature*, 354, 84–86 (1991)], with 29 different amino acids at $R^1$, 27 different amino acids at $R^3$ and 40 different carboxylic acids at $R^4$, 97 different N-benzyl-diketopiperazines, ($R^2$=Bzl) and 97 different N-methyl diketopiperazines, ($R^2$=Me) were synthesized in which the individual building blocks were varied while fixing the remaining two positions. Those compounds are illustrated as the diketopiperazines in the Table after Example 2.

Modifications occurring to the amino acid side chains during the N-alkylation and reduction steps have been carefully studied. During the N-alkylation with methyl iodide and benzyl bromide, the protected $N^\epsilon$-amine of lysine was alkylated, and the Boc protecting group, when present, was reduced during the reduction step yielding the corresponding $N^\epsilon,N^\epsilon$-dimethyl and $N^\epsilon$-benzyl, $N^\epsilon$-methyl-polyamines, respectively.

Using the information from these control studies and following the selection of the appropriate compounds for each of the three positions of diversity, N-benzyl ($R^2$=Bzl) diketopiperazine and N-methyl ($R^2$=Me) diketopiperazine libraries were prepared.

Any variety of amino acids can be used with the present invention as described above to generate a vast array of compounds with different $R^1$ and $R^3$ groups. As described in the ensuing Examples, twenty-nine first amino acids were coupled to the resin, which amino acids contain $R^1$. The twenty nine amino acids included Ala, Phe, Gly, Ile, Leu, Nva, Ser(tBu), Thr(tBu), Val, Tyr(tBu), Nle, Cha, Nal, Phg, Lys (Boc), Met(O), ala, phe, ile, leu, nva, ser(tBu), thr(tBu), val, tyr(tBu), nle, cha, nal, lys(Boc). After the above described N-alkylation, twenty-seven different amino acids were used for the coupling of the second amino acid, thereby providing twenty-seven various $R^3$ groups. Those twenty seven-amino acids included Ala, Phe, Gly, Ile, Leu, Nva, Ser(tBu), Thr(tBu), Val, Tyr(tBu), Nle, Cha, Nal, Phg, Met(O), ala, phe, ile, leu, nva, ser(tBu), thr(tBu), val, tyr(tBu), nle, cha and nal. Following usual notation, L-amino acids are referred to with an initial capital letter as in Val, whereas D-amino acids are referred to with an initial lower case letter as in ala.

As used herein, abbreviations for the various amino acid side-chain protecting groups are as follows: "Trt" for trityl, "tBu" for tert-butyl, "Boc" for tert-butoxycarbonyl and "BrZ" for 2-bromobenzyloxycarbonyl.

As can be seen from the amino acid side chains exemplified above, it should be appreciated from the above-described embodiments of $R^1$ and $R^3$, as well as from the described reaction scheme, that some of the amino acid side chains are modified during the synthesis. For instance some of the $R^1$ amino acid side chains are modified by the N-alkylation and/or the reduction steps. Similarly, certain $R^3$ groups are modified by the reduction procedures. Accordingly, the twenty-nine preferred embodiments of $R^1$ and the twenty-seven of $R^3$ are described above and below, except in Table 1, in their modified form. A specific example of a modified lysine side is provided above. Similarly, certain $R^4$ groups can be modified by the reduction procedure, as is well known.

TABLE 1

| Amino acid name | | Side chain R |
|---|---|---|
| Full | 3-letter code | (For $R^1$ and $R^3$) |
| Glycine | Gly | ⟿H |
| Alanine | Ala | ⟿CH₃ |
| Valine | Val | ⟿CH(CH₃)₂ |
| Leucine | Leu | ⟿CH₂—CH(CH₃)₂ |
| Isoleucine | Ile | ⟿CH(CH₃)CH₂CH₃ |
| Lysine | Lys | ⟿(CH₂)₄—NH₂ |
| Serine | Ser | ⟿CH₂—OH |
| Threonine | Thr | ⟿CH(CH₃)—OH |
| Phenylalanine | Phe | 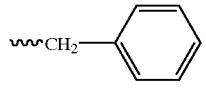 |
| Tyrosine | Tyr | 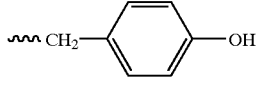 |
| Norvaline | Nva | ⟿(CH₂)₂—CH₃ |
| Norleucine | Nle | ⟿(CH₂)₃—CH₃ |
| Naphthylalanine | Nal | 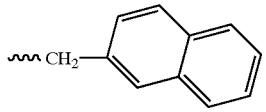 |

TABLE 1-continued

| Amino acid name | | Side chain R |
|---|---|---|
| Full | 3-letter code | (For $R^1$ and $R^3$) |
| Cyclohexylalanine | Cha | ⟿CH₂—⬡ |
| Methionine | Met | ⟿CH₂—CH₂—S—CH₃ |
| Phenylglycine | Phg | ⟿⬡ |

A variety of carboxylic acids ($R^{4a}$COOH and $R^{5a}$COOH) can be used in the acylation steps of reaction Scheme 1, thereby providing a wide array of substituents at the $R^4$ and $R^5$ positions and substituentds of an illustrative diketopiperazine. Forty carboxylic acids were used in preparing the diketopiperazine compounds and libraries. Those syntheses were carried out using the following carboxylic acids: 1-phenyl-1-cyclopropane carboxylic acid, m-tolylacetic acid, 3-fluorophenyl-acetic acid, (α,α,α)-trifluoro-m-tolylacetic acid, p-tolylacetic acid, 3-methoxyphenylacetic acid, 4-methoxyphenylacetic acid, 4-ethoxyphenylacetic acid, 4-isobutyl-α-methylphenylacetic acid, 3,4-dichlorophenylacetic acid, 3,5-bis(trifluoromethyl)phenylacetic acid, phenylacetic acid, hydrocinnamic acid, 4-phenylbutyric acid, butyric acid, heptanoic acid, isobutyric acid, isovaleric acid, 4-methylvaleric acid, trimethylacetic acid, tert-butylacetic acid, cyclohexanecarboxylic acid, cyclohexylacetic acid, cyclohexanebutyric acid, cycloheptanecarboxylic acid, acetic acid, cyclobutanecarboxylic acid, cyclopentanecarboxylic acid, cyclohexanepropionicn acid, 4-methyl-1-cyclohexanecarboxylic acid, 4-tert-butyl-cyclohexanecarboxylic acid, 1-adamantaneacetic acid, 3,3-diphenylpropionic acid, dicyclohexylacetic acid, indole-3-acetic acid, 1-naphthylacetic acid, 3-(3,4,5)-trimethoxyphenylpropionic acid, 2-norbornaneacetic acid, cyclopentylacetic acid, 2-ethylbutyric acid.

The synthesis of 1,6-diketo-(2-substituted or 2,3-disubstituted)-(5-aminoethyl)-2,5-diazacyclic compounds and the corresponding (1-substituted or 1,2-disubstituted)-(4-aminoethyl)-(1,4-diazacyclic compounds having 7- or 8-atoms in the cyclic ring or an unsaturated bond between the two carbonyl groups can be carried out in a similar manner to that shown in Scheme 1 by reacting a longer activated diacid such as a diacid halide like a diacid chloride or diimidazole compound with resin-bound compound 5. A tertiary amine such as diisopropylethylamine is typically also present when a diacid chloride or similar compound is used in these syntheses. Exemplary reactions are shown in Scheme 2, below, wherein only the ring-forming step is shown

Scheme 2
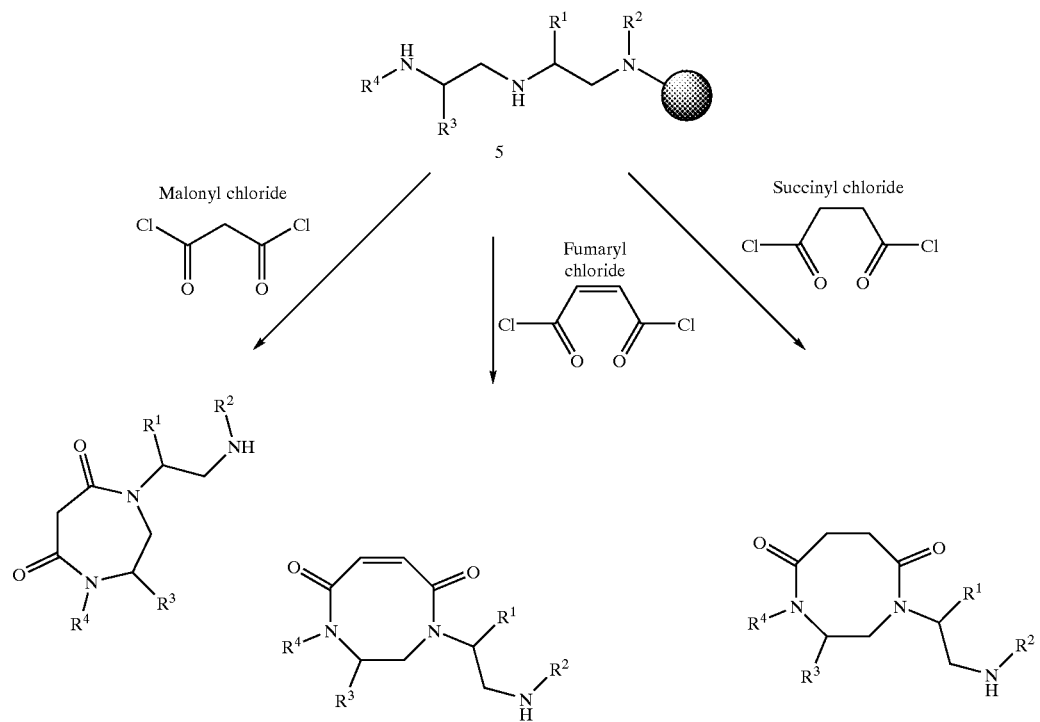
Bi- and tricyclic compounds can be prepared using the same general synthetic steps, but using a cyclic activated α,β-diacid as is illustrated in Scheme 3, below.
Scheme 3
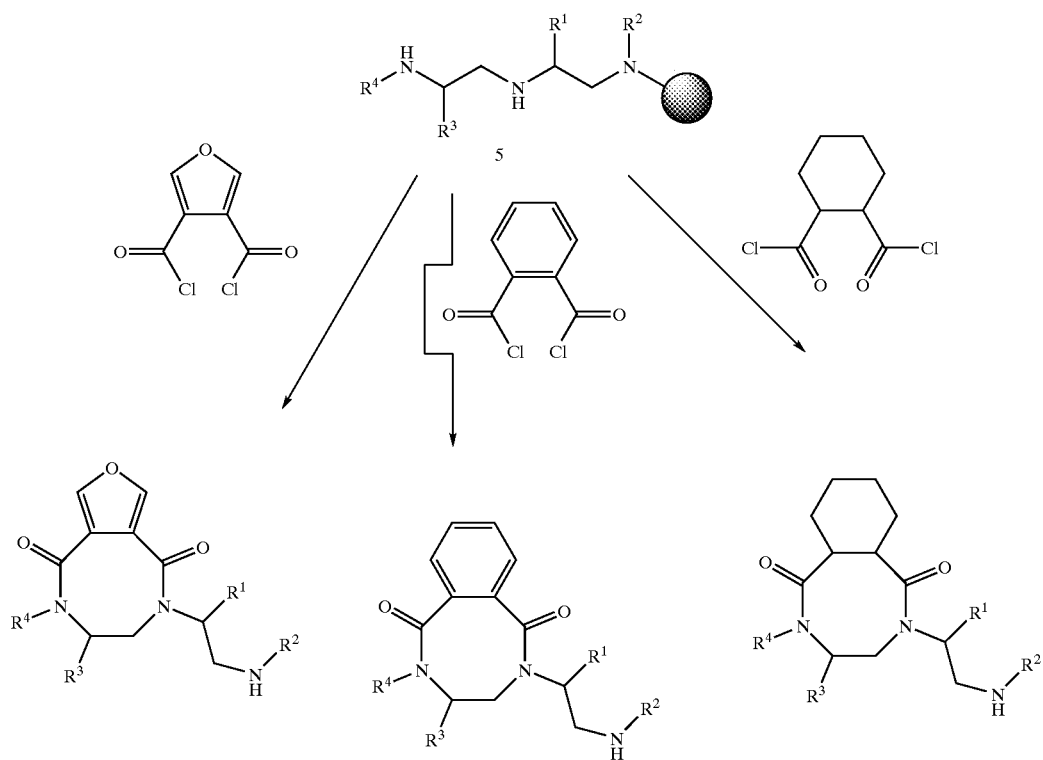

It is to be understood that the 1,4-diazacyclic compounds corresponding to those shown in Schemes 2 and 3 are prepared and further reacted in the same manner as are the 1,4-diazacyclic compounds of Scheme 1.

Compounds and libraries containing a single amido carbonyl group can be prepared by several well-known synthetic methods. For example, a substituted or unsubstituted acryloyl halide can be reacted using a Michael addition to one amine of compound 5 and the acid halide used to form the amide bond with the second amine.

The nonsupport-bound library mixtures were screened in solution in radio-receptor inhibition assays described in detail below. Deconvolution of highly active mixtures can then be carried out by iterative, or positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., Nature, 354, 84–86 (1991) and Dooley et al., Science. 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each assayed to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries. In the positional scanning approach sublibraries are made defining only one variable with each set of sublibraries- and all possible sublibraries with each single variable defined (and all other possibilities at all of the other variable positions) is made and tested. From the instant description one skilled in the art can synthesize libraries wherein 2 fixed positions are defined at a time. From the assaying of each single-variable defined library, the optimum substituent at that position is determined, pointing to the optimum or at least a series of compounds having a maximum of the desired biological activity. Thus, the number of sublibraries for compounds with a single position defined is the number of different substituents desired at that position, and the number of all the compounds in each sublibrary is the product of the number of substituents at each of the other variables.

As pharmaceutical compositions for treating infections, pain, or other indications known to be treatable by a contemplated diketopiperazine or other contemplated compound, a compound of the present invention is generally in a pharmaceutical composition so as to be administered to a subject in need of the medication at dosage levels of about 0.7 to about 7000 mg per day, and preferably about 1 to about 500 mg per day, for a normal human adult of approximately 70 kg of body weight, this translates into a dosage of about 0.01 to about 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

EXAMPLE 1

Typical Procedure for the Individual Synthesis of 4, 5-disubstituted-2,3-diketopiperazines The synthetic route followed in these preparations is illustrated in Scheme 4, below, whose reactants are discussed in the text that follows.

borane was disproportionated by treatment with piperidine at 65° C. overnight (about 18 hours). The resin was then washed with methanol (2 times) and DMF (6 times) and dried.

4) Disubstituted diketopiperazine formation: The cyclization occurred following treatment of the reduced acylated amino acid overnight (about 18 hours) with oxalyldiimidazole (15x) in DMF anhydrous. Following cleavage from the resin with anhydrous HF in the presence of anisole at 0° C. for 6 hours, the desired product was extracted with acetonitrile/water (50:50) and lyophilized.

Product Data:

3a: $^1$H NMR (500 MHZ, DMSO-$d_6$) δ. 8.43 (d, J=4.53 Hz, 1H), 7.32–6.66 (m, 9H), 3.88 (m, 1H), 3.76 (m, 1H), 3.23 (dd, J=13.07, J=2.43 Hz), 2.89 (m, 1H), 2.88 (m, 2H), 2.82 (m, 2H), 2.63 (dd, J=13.34, J=9.51 Hz, 1H). $^{13}$C NMR (125 MHZ, DMSO-$d_6$): 157.48, 157.05, 156.05, 138.89, 130.16, 128.76, 128.37, 127.32, 126.32, 115,28, 56.98, 54.93, 47.52. ES-MS calcd for $C_{19}H_{20}N_2O_3$: 324.37, found: 325.40 (MH$^+$)

3f: $^1$H NMR (500 MHZ, DMSO-$d_6$) δ. 8.45 (d, J=3.80 Hz, 1H), 7.34–7.23 (m, 5H), 3.72 (m, 1H), 3.64 (dd, J=13.34,

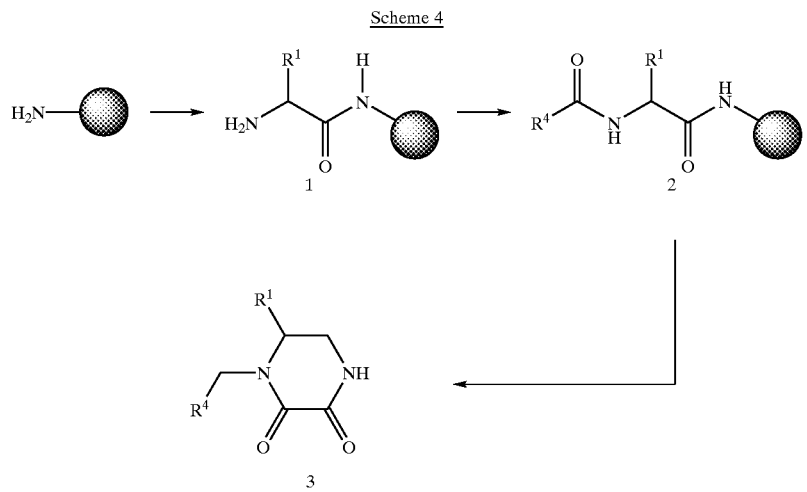

Scheme 4

1) Amino acid coupling and acylation: 100 mg p-methylbenzydrylamine (MBHA) resin (1.0 meq/g, 100–200 mesh) was contained within a sealed polypropylene mesh packet [Houghten, R. A., Proc. Natl. Acad. Sci. USA 1985, 82, 5131]. Reactions were carried out in 10 ml polyethylene bottles. Following neutralization with 5% diisopropylethylamine (DIEA) in dichloromethane (DCM), the resin was washed with DCM. The first amino acid (Fmoc-R$^1$aa-OH, 6 eq) was coupled using the conventional reagents hydroxybenzotriazole (HOBt, 6 eq) and diisopropylcarbodiimide (DIC, 6 eq) in anhydrius DMF for 60 minutes.

2) Following removal of the protecting group with 25% piperidine in DMF (2 times, 2×10 minutes) and wash with DMF (8 times), the amino acid was N-acylated with a carboxylic acid (10 eq) in the presence of DIC (10 eq) and HOBt (10 eq) overnight (about 18 hours) in anhydrous DMF.

3) Exhaustive reduction of the amide groups: The reduction was performed in 50 ml Kimax™ tubes under nitrogen. Boric acid (40x) and trimethyl borate (40x) were added, followed by 1M BH$_3$-THF (40x). The tubes were heated at 65° C. for 72 hours, followed by quenching with MeOH. The resin was then washed with methanol (2 times) and the J=6.91 Hz, 1H), 3.45 (dd, J=13.21, J=3.32 Hz), 2.99 (dd, J=13.35, J=5.10 Hz, 1H), 2.95 (dd, J=14.45, J=5.48 Hz, 1H), 2.88 (dd, J=13.56, J=6.92 Hz, 1H), 2.81 (dd, J=13.10, J=9.76 Hz, 1H), 1.08 (t, J=6.94 Hz, 3H). $^{13}$C NMR (125 MHZ, DMSO-$d_6$): 157.61, 156.82, 137.44, 129.29, 128.53, 126.68, 55.81, 40.57, 40.20, 36.78, 13.00. ES-MS calcd for $C_{13}H_{16}N_2O_2$: 232.28, found: 233.20 (MH$^+$).

3l: $^1$H NMR (500 MHZ, DMSO-$d_6$) δ. 8.47 (d, J=4.17 Hz, 1H), 3.62 (m, 1H), 3.61 (m, 1H), 3.53, dd, J=13.45, J=7.86 Hz, 1H), 3.06 (m, 1H), 2.70 (dd, J=13.00, J=7.26 Hz, 1H), 1.93 (m, 1H), 1.22 (d, J=7.09 Hz, 3H), 0.88 (d, J=6.73 Hz, 3H), 0.82 (d, J=6.73 Hz, 3H). $^{13}$C NMR (125 MHZ, DMSO-$d_6$): 157.50, 157.44, 51.68, 50.63, 43.17, 26.59, 19.95, 19.90, 16.75. ES-MS calcd for $C_9H_{16}N_2O_2$: 184.24, found: 185.10 (MH$^+$).

3r: $^1$H NMR (500 MHZ, DMSO-$d_6$) δ. 8.34 (d, J=3.98 Hz, 1H), 3.81 (m, 1H), 3.46 (m, 1H), 3.28 (m, 2H), 2.89 (m, 1H), 1.96 (m, 1H), 1.09 (t, J=6.91 Hz, 1H), 0.96 (d, J=6.73 Hz, 3H), 0.88 (d, J=6.73 Hz, 3H). $^{13}$C NMR (125 MHZ, DMSO-$d_6$): 157.50, 157.44, 51.68, 50.63, 43.17, 26.59, 19.95, 19.90, 16.75. ES-MS calcd for $C_9H_{16}N_2O_2$: 184.24, found: 185.20 (MH$^+$)

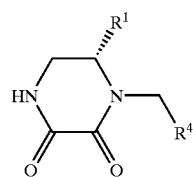

| Entry | R¹ | R⁴ | MW expected | MW found |
|---|---|---|---|---|
| 3a | $CH_2$—$C_6H_4$—$OH^*$ | $CH_2Ph$ | 324.37 | 325.4 ($MH^+$) |
| 3b | $CH_2$—$C_6H_4$—OH | $CH_3$ | 248.28 | 249.2 ($MH^+$) |
| 3c | $CH_2$—$C_6H_4$—OH | $CH_2$—$C_5H_{11}$ | 316.39 | 317.3 ($MH^+$) |
| 3d | $CH_2$—$C_6H_4$—OH | $CH(CH_3)_2$ | 276.33 | 277.2 ($MH^+$) |
| 3e | $CH_2Ph^*$ | $CH_2Ph$ | 308.37 | 309.3 ($MH^+$) |
| 3f | $CH_2Ph$ | $CH_3$ | 232.28 | 233.2 ($MH^+$) |
| 3g | $CH_2Ph$ | $CH_2$—$C_5H_{11}$ | 300.40 | 301.2 ($MH^+$) |
| 3h | $CH_2Ph$ | $CH(CH_3)_2$ | 260.33 | 261.2 ($MH^+$) |
| 3i | $CH_3$ | $CH_2Ph$ | 232.28 | 233.2 ($MH^+$) |
| 3j | $CH_3$ | $CH_3$ | 156.18 | 157.2 ($MH^+$) |
| 3k | $CH_3$ | $CH_2$—$C_5H_{11}$ | 224.30 | 225.2 ($MH^+$) |
| 3l | $CH_3$ | $CH(CH_3)_2$ | 184.24 | 185.1 ($MH^+$) |
| 3m | $CH_2OH$ | $CH_2Ph$ | 248.28 | 249.9 ($MH^+$) |
| 3n | $CH_2OH$ | $CH_3$ | 172.18 | 173.2 ($MH^+$) |
| 3o | $CH_2OH$ | $CH_2$—$C_5H_{11}$ | 240.30 | 241.2 ($MH^+$) |
| 3p | $CH_2OH$ | $CH(CH_3)_2$ | 200.24 | 201.9 ($MH^+$) |
| 3q | $CH(CH_3)_2$ | $CH_2Ph$ | 260.33 | 261.2 ($MH^+$) |
| 3r | $CH(CH_3)_2$ | $CH_3$ | 184.24 | 185.2 ($MH^+$) |
| 3s | $CH(CH_3)_2$ | $CH_2$—$C_5H_{11}$ | 252.35 | 253.2 ($MH^+$) |
| 3t | $CH(CH_3)_2$ | $CH(CH_3)_2$ | 212.29 | 213.2 ($MH^+$) |

*$C_6H_4$ is phenyl and Ph is phenyl.

EXAMPLE 2

Typical Procedure for the Individual Synthesis of 1, 4,5-trisubstituted-2,3-diketopiperazines The compounds of this example were prepared following the general reaction pathway shown in Scheme 5, below, wherein the reactants are discussed in the following text.

1) Amino acid coupling and selective amide N-alkylation: The first amino acid was coupled in the same conditions as described before. Following removal of the protecting group with 25% piperidine in DMF (2 times, 2×10 minutes) and washing with DMF (8 times), the mesh packet was shaken overnight (about 18 hours) in a solution of trityl chloride in DCM/DMF (9:1) in the presence of DIEA. Completeness of the trityl coupling was verified using the bromophenol blue color test [Krchák, V. et al., *Coll. Czech. Chem. Comm*, 1988, 53, 2542]. N-alkylation was performed by treatment of the resin packet with 1 M lithium t-butoxide in THF (20 eq) during 10 minutes at room temperature. Excess base was removed by cannulation, followed by addition of the individual alkylating agent (20 eq) in anhydrous DMSO. The solution was vigorously shaken for 2 hours at room temperature.

2) N-acylated dipeptide: Upon removal of the trityl from the α-amino group with 2% TFA in DCM (2×10 min), the resin packet was washed, neutralized with a solution of 5% DIEA in DCM, and the-second amino acid (Fmoc—$R^3$aa-OH) coupled in the same conditions as described before. Following removal of the Fmoc group, the dipeptide was N-acylated with a carboxylic acid (10 eq) in the presence of DIC (10 eq) and HOBt (10 eq) in anhydrous DMF.

3) Exhaustive reduction of the amide groups: The reduction was performed in the same conditions as described before.

4) Trisubstituted diketopiperazine formation: The cyclization occurred following treatment of the reduced acylated dipeptide overnight (about 18 hours) with oxalyldiimidazole (15×) in DMF anhydrous. Following cleavage from the resin with anhydrous HF in the presence of anisole at 0° C. for 6 hours [Houghten, R. A. et al., *Int. J. Pep. Pro. Res.*, 1986, 27, 6763], the desired product was extracted with acetonitrile/water (50:50) and lyophilized.

Product Data:

6i: ¹H NMR (500 MHZ, DMSO-$d_6$) δ 7.13–7.6 (m, 20H), 4.37 (m, 1H), 4.15–4.23 (m, 2H), 3.67–3.83 (m, 8H), 3.35 (m, 1H), 2.94–3.09 (m, 4H), 2.67–2.84 (m, 4H), 1.58 (m, 2H), 1.16 (m, 1H). ¹³C NMR (125 MHZ, DMSO-$d_6$): 157.58, 155.97, 138.69, 137.53, 131.41, 131.15, 130.21, 129.89, 129.62, 129.17, 129.04, 128.91, 128.73, 128.68, 128.39, 126.79, 126.36, 58.39, 55.32, 54.34, 50.62, 47.94, 47.65, 37.16, 33.00, 28.42, 22.92. ES-MS calcd for $C_{40}H_{48}N_4O_2$: 616.34, found: 617.60 ($MH^+$).

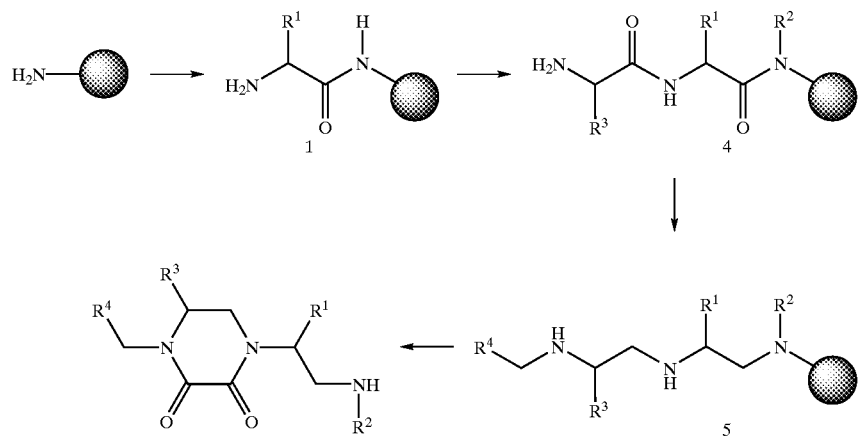

Scheme 5

6e: ¹H NMR (500 MHZ, DMSO-$d_6$) δ 7.24–7.36 (m, 15H), 5.13 (m, 1H), 4.57 (d, J=14.5 Hz, 1H), 4.46 (d, J=14.5 Hz, 1H), 4.12 (dd, J=8.7, 14.8 Hz, 1H), 3.92 (m, 1H), 3.51 (m, 2H), 3.18–3.26 (m, 5H), 3.08 (dd, J=3.8, 14.8 Hz, 1H), 2.88 (m, 3H). $^{13}$C NMR (125 MHZ, DMSO-$d_6$): 158.47, 156.14, 136.92, 136.13, 129.10, 128.72, 128.64, 128.55, 128.23, 127.56, 127.08, 126.88, 60.06, 56.18, 54.57, 49.92, 46.20, 44.96, 44.72, 42.50, 36.22, 34.57, 31.73. ES-MS calcd for $C_{29}H_{33}N_3O_3$: 471.25, found: 472.2 (MH$^{30}$).

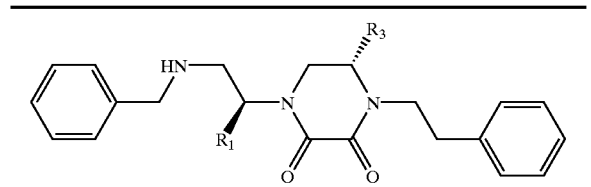

| Entry | R$_1$ | R$_3$ | MW expected | MW found |
|---|---|---|---|---|
| 6a | CH$_2$Ph* | CH$_2$Ph | 531.29 | 532.2 (MH$^+$) |
| 6b | CH$_2$Ph | CH(CH$_3$)$_2$ | 483.29 | 484.3 (MH$^+$) |
| 6c | CH(CH$_3$)CH$_2$CH$_3$ | CH$_2$Ph | 497.30 | 498.3 (MH$^+$) |
| 6d | CH(CH$_3$)CH$_2$CH$_3$ | CH(CH$_3$)$_2$ | 449.30 | 450.3 (MH$^+$) |
| 6e | CH$_2$OH | CH$_2$Ph | 471.25 | 472.2 (MH$^+$) |
| 6f | CH$_2$OH | CH(CH$_3$)$_2$ | 423.25 | 424.2 (MH$^+$) |
| 6g | CH$_3$ | CH$_2$Ph | 455.26 | 456.3 (MH$^+$) |
| 6h | CH$_3$ | CH(CH$_3$)$_2$ | 407.26 | 408.3 (MH$^+$) |
| 6i | (CH$_2$)$_4$N(CH$_3$)CH$_2$Ph | CH$_2$Ph | 616.38 | 617.6 (MH$^+$) |
| 6j | (CH$_2$)$_4$N(CH$_3$)CH$_2$Ph | CH(CH$_3$)$_2$ | 568.38 | 569.5 (MH$^+$) |

*Ph is monosubstituted phenyl.

Lists of individual N-benzyl and N-methyl compounds prepared as discussed in this example is provided below in Tables 2 and 3. The compounds are listed by preparation number (Prep) followed by the amino acid or carboxylic acid used to provide R$^1$, R$^3$ and R$^4$.

TABLE 2

N-Benzyl and N-Methyl-1,4,5-trisubstituted-2,3-diketopiperazines

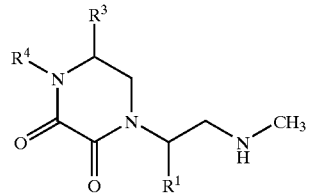

| Prep | R$^1$ | R$^3$ | R$^4$ |
|---|---|---|---|
| 1 | Fmoc-Ala | Fmoc-Phe | Phenylacetic Acid |
| 2 | Fmoc-Phe | Fmoc-Phe | Phenylacetic Acid |
| 3 | Fmoc-Gly | Fmoc-Phe | Phenylacetic Acid |
| 4 | Fmoc-Ile | Fmoc-Phe | Phenylacetic Acid |
| 5 | Fmoc-Lys(Boc) | Fmoc-Phe | Phenylacetic Acid |
| 6 | Fmoc-Leu | Fmoc-Phe | Phenylacetic Acid |
| 7 | Fmoc-Met(O) | Fmoc-Phe | Phenylacetic Acid |
| 8 | Fmoc-Ser(tBut) | Fmoc-Phe | Phenylacetic Acid |
| 9 | Fmoc-Thr(tBut) | Fmoc-Phe | Phenylacetic Acid |
| 10 | Fmoc-Val | Fmoc-Phe | Phenylacetic Acid |
| 11 | Fmoc-Tyr(tBut) | Fmoc-Phe | Phenylacetic Acid |
| 12 | Fmoc-ala | Fmoc-Phe | Phenylacetic Acid |
| 13 | Fmoc-phe | Fmoc-Phe | Phenylacetic Acid |
| 14 | Fmoc-ile | Fmoc-Phe | Phenylacetic Acid |
| 15 | Fmoc-lys(Boc) | Fmoc-Phe | Phenylacetic Acid |
| 16 | Fmoc-leu | Fmoc-Phe | Phenylacetic Acid |
| 17 | Fmoc-ser(tBut) | Fmoc-Phe | Phenylacetic Acid |
| 18 | Fmoc-thr(tBut) | Fmoc-Phe | Phenylacetic Acid |
| 19 | Fmoc-val | Fmoc-Phe | Phenylacetic Acid |
| 20 | Fmoc-tyr(tBut) | Fmoc-Phe | Phenylacetic Acid |
| 21 | Fmoc-Nle | Fmoc-Phe | Phenylacetic Acid |
| 22 | Fmoc-nle | Fmoc-Phe | Phenylacetic Acid |
| 23 | Fmoc-Nva | Fmoc-Phe | Phenylacetic Acid |
| 24 | Fmoc-nva | Fmoc-Phe | Phenylacetic Acid |
| 25 | Fmoc-NapAla | Fmoc-Phe | Phenylacetic Acid |
| 26 | Fmoc-napala | Fmoc-Phe | Phenylacetic Acid |
| 27 | Fmoc-Phg | Fmoc-Phe | Phenylacetic Acid |
| 28 | Fmoc-ChAla | Fmoc-Phe | Phenylacetic Acid |
| 29 | Fmoc-chala | Fmoc-Phe | Phenylacetic Acid |
| 30 | Fmoc-Phe | Fmoc-Ala | Phenylacetic Acid |
| 31 | Fmoc-Phe | Fmoc-Phe | Phenylacetic Acid |
| 32 | Fmoc-Phe | Fmoc-Gly | Phenylacetic Acid |
| 33 | Fmoc-Phe | Fmoc-Ile | Phenylacetic Acid |
| 34 | Fmoc-Phe | Fmoc-Leu | Phenylacetic Acid |
| 35 | Fmoc-Phe | Fmoc-Met(O) | Phenylacetic Acid |
| 36 | Fmoc-Phe | Fmoc-Ser(tBut) | Phenylacetic Acid |
| 37 | Fmoc-Phe | Fmoc-Thr(tBut) | Phenylacetic Acid |
| 38 | Fmoc-Phe | Fmoc-Val | Phenylacetic Acid |
| 39 | Fmoc-Phe | Fmoc-Tyr(tBut) | Phenylacetic Acid |
| 40 | Fmoc-Phe | Fmoc-ala | Phenylacetic Acid |
| 41 | Fmoc-Phe | Fmoc-phe | Phenylacetic Acid |
| 42 | Fmoc-Phe | Fmoc-ile | Phenylacetic Acid |
| 43 | Fmoc-Phe | Fmoc-leu | Phenylacetic Acid |
| 44 | Fmoc-Phe | Fmoc-ser(tBut) | Phenylacetic Acid |
| 45 | Fmoc-Phe | Fmoc-thr(tBut) | Phenylacetic Acid |
| 46 | Fmoc-Phe | Fmoc-val | Phenylacetic Acid |
| 47 | Fmoc-Phe | Fmoc-tyr(tBut) | Phenylacetic Acid |
| 48 | Fmoc-Phe | Fmoc-Nle | Phenylacetic Acid |
| 49 | Fmoc-Phe | Fmoc-nle | Phenylacetic Acid |
| 50 | Fmoc-Phe | Fmoc-Nva | Phenylacetic Acid |
| 51 | Fmoc-Phe | Fmoc-nva | Phenylacetic Acid |
| 52 | Fmoc-Phe | Fmoc-NapAla | Phenylacetic Acid |
| 53 | Fmoc-Phe | Fmoc-napAla | Phenylacetic Acid |
| 54 | Fmoc-Phe | Fmoc-Phg | Phenylacetic Acid |
| 55 | Fmoc-Phe | Fmoc-ChAla | Phenylacetic Acid |
| 56 | Fmoc-Phe | Fmoc-chala | Phenylacetic Acid |
| 57 | Fmoc-Phe | Fmoc-Phe | 1-Phenyl-1-cyclopropane-carboxylic Acid |
| 58 | Fmoc-Phe | Fmoc-Phe | m-Tolylacetic Acid |
| 59 | Fmoc-Phe | Fmoc-Phe | 3-Fluorophenyl-acetic Acid |
| 60 | Fmoc-Phe | Fmoc-Phe | (α,α,α-Trifluoro-m-tolyl)acetic acid |
| 61 | Fmoc-Phe | Fmoc-Phe | p-Tolylacetic Acid |
| 62 | Fmoc-Phe | Fmoc-Phe | 3-Methoxyphenyl-acetic Acid |
| 63 | Fmoc-Phe | Fmoc-Phe | 4-Methoxyphenyl-acetic Acid |
| 64 | Fmoc-Phe | Fmoc-Phe | 4-Ethoxyphenyl-acetic Acid |
| 65 | Fmoc-Phe | Fmoc-Phe | 4-Isobutyl-α-Methylphenyl-acetic Acid |
| 66 | Fmoc-Phe | Fmoc-Phe | 3,4-Dichlorophenyl-acetic Acid |
| 67 | Fmoc-Phe | Fmoc-Phe | 3,5-Bis(trifluoromethyl)-phenylacetic Acid |
| 68 | Fmoc-Phe | Fmoc-Phe | Phenylacetic Acid |
| 69 | Fmoc-Phe | Fmoc-Phe | Hydrocinnamic Acid |

TABLE 2-continued

N-Benzyl and N-Methyl-1,4,5-trisubstituted-2,3-diketopiperazines

| Prep | R¹ | R³ | R⁴ |
|------|------|------|------|
| 70 | Fmoc-Phe | Fmoc-Phe | 4-Phenylbutyric Acid |
| 71 | Fmoc-Phe | Fmoc-Phe | Butyric Acid |
| 72 | Fmoc-Phe | Fmoc-Phe | Heptanoic Acid |
| 73 | Fmoc-Phe | Fmoc-Phe | isobutyric Acid |
| 74 | Fmoc-Phe | Fmoc-Phe | Isovaleric Acid |
| 75 | Fmoc-Phe | Fmoc-Phe | 4-Methylvaleric Acid |
| 76 | Fmoc-Phe | Fmoc-Phe | Trimethylacetic Acid |
| 77 | Fmoc-Phe | Fmoc-Phe | tert-Butylacetic Acid |
| 78 | Fmoc-Phe | Fmoc-Phe | Cyclohexane-carboxylic Acid |
| 79 | Fmoc-Phe | Fmoc-Phe | Cyclohexyl-acetic Acid |
| 80 | Fmoc-Phe | Fmoc-Phe | Cyclohexane-butyric Acid |
| 81 | Fmoc-Phe | Fmoc-Phe | Cycloheptane-carboxylic Acid |
| 82 | Fmoc-Phe | Fmoc-Phe | Acetic Acid |
| 83 | Fmoc-Phe | Fmoc-Phe | Cyclobutane-carboxylic Acid |
| 84 | Fmoc-Phe | Fmoc-Phe | Cyclopentane-carboxylic Acid |
| 85 | Fmoc-Phe | Fmoc-Phe | Cyclohexane-propionic Acid |
| 86 | Fmoc-Phe | Fmoc-Phe | 4-Methyl-1-cyclohexane-carboxylic Acid |
| 87 | Fmoc-Phe | Fmoc-Phe | 4-tert-Butyl-cyclohexane-carboxylic Acid |
| 88 | Fmoc-Phe | Fmoc-Phe | 1-Adamantane-acetic Acid |
| 89 | Fmoc-Phe | Fmoc-Phe | 3,3-Diphenyl-propionic Acid |
| 90 | Fmoc-Phe | Fmoc-Phe | Dicyclohexy-lacetic Acid |
| 91 | Fmoc-Phe | Fmoc-Phe | Indole-3-acetic Acid |
| 92 | Fmoc-Phe | Fmoc-Phe | 1-Naphthylacetic Acid |
| 93 | Fmoc-Phe | Fmoc-Phe | 3-(3,4,5-Trimethoxy-phenyl)propionic Acid |
| 94 | Fmoc-Phe | Fmoc-Phe | 2-Norbornane acetic Acid |
| 95 | Fmoc-Phe | Fmoc-Phe | Cyclopentyl-acetic Acid |
| 96 | Fmoc-Phe | Fmoc-Phe | 2-Ethylbutyric acid |

TABLE 3

Individual N-Methyl- and N-Benzyl-1,4,5-trisubstituted piperazine Compounds Synthesized

| Prep | R¹ | R³ | R⁴ |
|------|------|------|------|
| 01 | Fmoc-Ala | Fmoc-Phe | Phenylacetic Acid |
| 02 | Fmoc-Phe | Fmoc-Phe | Phenylacetic Acid |
| 03 | Fmoc-Gly | Fmoc-Phe | Phenylacetic Acid |
| 04 | Fmoc-Ile | Fmoc-Phe | Phenylacetic Acid |
| 05 | Fmoc-Lys(Boc) | Fmoc-Phe | Phenylacetic Acid |
| 06 | Fmoc-Leu | Fmoc-Phe | Phenylacetic Acid |
| 07 | Fmoc-Met(O) | Fmoc-Phe | Phenylacetic Acid |
| 08 | Fmoc-Ser(tBut) | Fmoc-Phe | Phenylacetic Acid |
| 09 | Fmoc-Thr(tBut) | Fmoc-Phe | Phenylacetic Acid |
| 10 | Fmoc-Val | Fmoc-Phe | Phenylacetic Acid |
| 11 | Fmoc-Tyr(tBut) | Fmoc-Phe | Phenylacetic Acid |
| 12 | Fmoc-ala | Fmoc-Phe | Phenylacetic Acid |
| 13 | Fmoc-phe | Fmoc-Phe | Phenylacetic Acid |
| 14 | Fmoc-ile | Fmoc-Phe | Phenylacetic Acid |
| 15 | Fmoc-lys(Boc) | Fmoc-Phe | Phenylacetic Acid |
| 16 | Fmoc-leu | Fmoc-Phe | Phenylacetic Acid |
| 17 | Fmoc-ser(tBut) | Fmoc-Phe | Phenylacetic Acid |
| 18 | Fmoc-thr(tBut) | Fmoc-Phe | Phenylacetic Acid |
| 19 | Fmoc-val | Fmoc-Phe | Phenylacetic Acid |
| 20 | Fmoc-tyr(tBut) | Fmoc-Phe | Phenylacetic Acid |
| 21 | Fmoc-Nle | Fmoc-Phe | Phenylacetic Acid |
| 22 | Fmoc-nle | Fmoc-Phe | Phenylacetic Acid |
| 23 | Fmoc-Nva | Fmoc-Phe | Phenylacetic Acid |
| 24 | Fmoc-nva | Fmoc-Phe | Phenylacetic Acid |
| 25 | Fmoc-NapAla | Fmoc-Phe | Phenylacetic Acid |
| 26 | Fmoc-napala | Fmoc-Phe | Phenylacetic Acid |
| 27 | Fmoc-Phg | Fmoc-Phe | Phenylacetic Acid |
| 28 | Fmoc-ChAla | Fmoc-Phe | Phenylacetic Acid |
| 29 | Fmoc-chala | Fmoc-Phe | Phenylacetic Acid |
| 30 | Fmoc-Phe | Fmoc-Ala | Phenylacetic Acid |
| 31 | Fmoc-Phe | Fmoc-Phe | Phenylacetic Acid |
| 32 | Fmoc-Phe | Fmoc-Gly | Phenylacetic Acid |
| 33 | Fmoc-Phe | Fmoc-Ile | Phenylacetic Acid |
| 34 | Fmoc-Phe | Fmoc-Leu | Phenylacetic Acid |
| 35 | Fmoc-Phe | Fmoc-Met(O) | Phenylacetic Acid |
| 36 | Fmoc-Phe | Fmoc-Ser(tBut) | Phenytacetic Acid |
| 37 | Fmoc-Phe | Fmoc-Thr(tBut) | Phenylacetic Acid |
| 38 | Fmoc-Phe | Fmoc-Val | Phenylacetic Acid |
| 39 | Fmoc-Phe | Fmoc-Tyr(tBut) | Phenylacetic Acid |
| 40 | Fmoc-Phe | Fmoc-ala | Phenylacetic Acid |
| 41 | Fmoc-Phe | Fmoc-phe | Phenylacetic Acid |
| 42 | Fmoc-Phe | Fmoc-ile | Phenylacetic Acid |
| 43 | Fmoc-Phe | Fmoc-leu | Phenylacetic Acid |
| 44 | Fmoc-Phe | Fmoc-ser(tBut) | Phenylacetic Acid |
| 45 | Fmoc-Phe | Fmoc-thr(tBut) | Phenylacetic Acid |
| 46 | Fmoc-Phe | Fmoc-val | Phenylacetic Acid |
| 47 | Fmoc-Phe | Fmoc-tyr(tBut) | Phenylacetic Acid |
| 48 | Fmoc-Phe | Fmoc-Nle | Phenylacetic Acid |
| 49 | Fmoc-Phe | Fmoc-nle | Phenylacetic Acid |
| 50 | Fmoc-Phe | Fmoc-Nva | Phenylacetic Acid |
| 51 | Fmoc-Phe | Fmoc-nva | Phenylacetic Acid |

TABLE 3-continued

Individual N-Methyl- and N-Benzyl-1,4,5-trisubstituted piperazine Compounds Synthesized

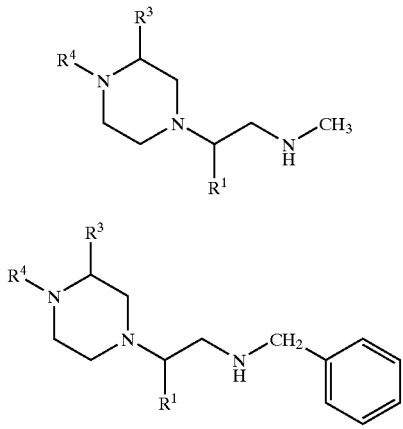

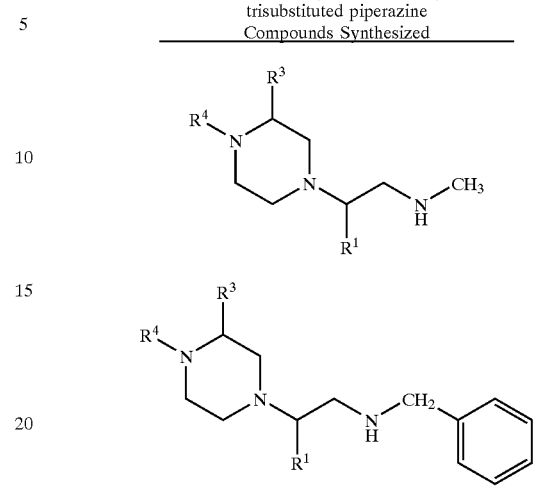

| Prep | R$^1$ | R$^3$ | R$^4$ |
|---|---|---|---|
| 52 | Fmoc-Phe | Fmoc-NapAla | Phenylacetic Acid |
| 53 | Fmoc-Phe | Fmoc-napala | Phenylacetic Acid |
| 54 | Fmoc-Phe | Fmoc-Phg | Phenylacetic Acid |
| 55 | Fmoc-Phe | Fmoc-ChAla | Phenylacetic Acid |
| 56 | Fmoc-Phe | Fmoc-chala | Phenylacetic Acid |
| 57 | Fmoc-Phe | Fmoc-Phe | 1-Phenyl-1-cyclopropane carboxylic Acid |
| 58 | Fmoc-Phe | Fmoc-Phe | m-Tolylacetic Acid |
| 59 | Fmoc-Phe | Fmoc-Phe | 3-Fluorophenylacetic Acid |
| 60 | Fmoc-Phe | Fmoc-Phe | (α,α,α-Trifluoro-m-tolyl)-acetic Acid |
| 61 | Fmoc-Phe | Fmoc-Phe | p-Tolylacetic Acid |
| 62 | Fmoc-Phe | Fmoc-Phe | 3-Methoxyphenylacetic Acid |
| 63 | Fmoc-Phe | Fmoc-Phe | 4-Methoxyphenylacetic Acid |
| 64 | Fmoc-Phe | Fmoc-Phe | 4-Ethoxyphenylacetic Acid |
| 65 | Fmoc-Phe | Fmoc-Phe | 4-Isobutyl-α-methylphenylacetic Acid |
| 66 | Fmoc-Phe | Fmoc-Phe | 3,4-Dichlorophenylacetic Acid |
| 67 | Fmoc-Phe | Fmoc-Phe | 3,5-Bis(trifluoromethyl)phenylacetic Acid |
| 68 | Fmoc-Phe | Fmoc-Phe | Phenylacetic Acid |
| 69 | Fmoc-Phe | Fmoc-Phe | Hydrocinnamic Acid |
| 70 | Fmoc-Phe | Fmoc-Phe | 4-Phenylbutyric Acid |
| 71 | Fmoc-Phe | Fmoc-Phe | Butyric Acid |
| 72 | Fmoc-Phe | Fmoc-Phe | Heptanoic Acid |
| 73 | Fmoc-Phe | Fmoc-Phe | Isobutyric Acid |
| 74 | Fmoc-Phe | Fmoc-Phe | Isovaleric Acid |
| 75 | Fmoc-Phe | Fmoc-Phe | 4-Methylvaleric Acid |
| 76 | Fmoc-Phe | Fmoc-Phe | Trimethylacetic Acid |
| 77 | Fmoc-Phe | Fmoc-Phe | tert-Butylacetic Acid |
| 78 | Fmoc-Phe | Fmoc-Phe | Cyclohexanecarboxylic Acid |
| 79 | Fmoc-Phe | Fmoc-Phe | Cyclohexylacetic Acid |
| 80 | Fmoc-Phe | Fmoc-Phe | Cyclohexanebutyric Acid |
| 81 | Fmoc-Phe | Fmoc-Phe | Cycloheptanecarboxylic Acid |
| 82 | Fmoc-Phe | Fmoc-Phe | Acetic Acid |
| 83 | Fmoc-Phe | Fmoc-Phe | Cyclobutanecarboxylic Acid |
| 84 | Fmoc-Phe | Fmoc-Phe | Cyclopentanecarboxylic Acid |
| 85 | Fmoc-Phe | Fmoc-Phe | Cyclohexanepropionic Acid |
| 86 | Fmoc-Phe | Fmoc-Phe | 4-Methyl-1-cyclohexanecarboxylic Acid |
| 87 | Fmoc-Phe | Fmoc-Phe | 4-tert-Butyl-cyclohexanecarboxylic Acid |
| 88 | Fmoc-Phe | Fmoc-Phe | 1-Adamantaneacetic Acid |
| 89 | Fmoc-Phe | Fmoc-Phe | 3-3-diphenyl propionic Acid |
| 90 | Fmoc-Phe | Fmoc-Phe | Dicyclohexylacetic Acid |
| 91 | Fmoc-Phe | Fmoc-Phe | Indole-3-acetic acid |
| 92 | Fmoc-Phe | Fmoc-Phe | 1-Naphthyl acetic acid |
| 93 | Fmoc-Phe | Fmoc-Phe | 3-(3,4,5)-Trimethoxyphenylpropionic Acid |
| 94 | Fmoc-Phe | Fmoc-Phe | 2-Norbomaneacetic Acid |
| 95 | Fmoc-Phe | Fmoc-Phe | Cyclopentylacetic Acid |
| 96 | Fmoc-Phe | Fmoc-Phe | 2-Ethyl butyric acid |

EXAMPLE 3

Preparation of Libraries of N-Methyl- and N-Benzyl-1,4,5-trisubstituted-2,3-diketopiperazines Libraries of N-methyl- and N-benzyl-1,4,5-trisubstituted-2,3-diketopiperazines were prepared. Here, whereas a single reagent was used to provide each of the R groups of the interemediates prepared in the syntheses of the individual compounds of Examples 1 and 2, both single reactants and mixtures of reactants were used to provide the R$^1$, R$^3$ and R$^4$ groups for the different library pools that were synthesiszed. As is discussed in greated detail below, 29 library pools were prepared in which R$^1$ was an individual amino acid side chain, and with R$^3$ and R$^4$ being separate mixtures of amino acid side chains (R$^3$) and carboxylic acid chains (R$^4$).

Where individual reactants were used to provide a particular R group, the procedures of Examples 1 and 2 were followed. Where mixtures were desired at a particular R group, the protected amino acids or carboxylic acids were provided in mixtures. The mixtures used to provide the various R groups are listed in Table 4, below, with the relative molar amount of each reactant being listed.

TABLE 4

Mixtures of Reactants Used to Prepare Resin-bound N-Methyl- and N-Benzyl-1,4,5-trisubstituted-2,3-diketopiperazine Library Intermediates 1, 3 and 4 of Scheme 1

| Fmoc-R¹aaOH | | Fmoc-R³aaOH | | R⁴COOH | |
|---|---|---|---|---|---|
| Relative Mole | Ratio | Relative Mole | Ratio | Relative Mole | Ratio |
| Fmoc-Ala | 0.833 | Fmoc-Ala | 0.833 | 1-Phenyl-1-cyclopropane-carboxylic Acid | 1.00 |
| Fmoc-Phe | 0.61 | Fmoc-Phe | 0.61 | m-Tolylacetic Acid | 1.80 |
| Fmoc-Gly | 1 | Fmoc-Gly | 1 | 3-Fluorophenyl-acetic Acid | 0.84 |
| Fmoc-Ile | 1.201 | Fmoc-Ile | 1.201 | (α,α,α-Trifluoro-m-tolyl)acetic Acid | 0.61 |
| Fmoc-Lys(Boc) | 1.016 | Fmoc-Leu | 0.932 | 3-Methoxy-phenylacetic Acid | 1.17 |
| Fmoc-Leu | 0.932 | Fmoc-Met(O) | 0.567 | 4-Methoxy-phenylacetic Acid | 1.80 |
| Fmoc-Met(O) | 0.567 | Fmoc-Ser(tBut) | 0.639 | 4-Ethoxyphenyl-acetic Acid | 1.40 |
| Fmoc-Ser(tBut) | 0.639 | Fmoc-Thr(tBut) | 0.865 | 4-Isobutyl-α-methylphenyl-acetic Acid | 1.70 |
| Fmoc-Thr(tBut) | 0.865 | Fmoc-Val | 1.136 | 3,4-Dichloro-phenylacetic Acid | 0.81 |
| Fmoc-Val | 1.136 | Fmoc-Tyr(tBut) | 0.672 | 3,5-Bis(trifluoromethyl)phenyl-acetic Acid | 0.50 |
| Fmoc-Tyr(tBut) | 0.672 | Fmoc-ala | 0.833 | Phenylacetic Acid | 1.00 |
| Fmoc-ala | 0.833 | Fmoc-phe | 0.61 | Hydrocinnamic Acid | 2.50 |
| Fmoc-phe | 0.61 | Fmoc-ile | 1.201 | 4-Phenylbutyric Acid | 3.00 |
| Fmoc-ile | 1.201 | Fmoc-leu | 0.932 | Butyric Acid | 3.39 |
| Fmoc-lys(Boc) | 1.016 | Fmoc-ser(tBut) | 0.639 | Heptanoic Acid | 3.51 |
| Fmoc-leu | 0.932 | Fmoc-thr(tBut) | 0.865 | Isobutyric Acid | 3.11 |
| Fmoc-ser(tBut) | 0.639 | Fmoc-val | 1.136 | Isovaleric Acid | 6.36 |
| Fmoc-thr(tBut) | 0.865 | Fmoc-tyr(tBut) | 0.672 | 4-Methylvaleric Acid | 3.32 |
| Fmoc-val | 1.136 | Fmoc-Nle | 0.938 | Trimethylacetic Acid | 4.24 |
| Fmoc-tyr(tBut) | 0.672 | Fmoc-nle | 0.938 | tert-Butylacetic Acid | 1.00 |
| Fmoc-Nle | 0.938 | Fmoc-Nva | 0.963 | Cyclohexane-carboxylic Acid | 3.51 |
| Fmoc-nle | 0.938 | Fmoc-nva | 0.963 | Cyclohexyl-acetic Acid | 3.95 |
| Fmoc-Nva | 0.963 | Fmoc-NapAla | 0.672 | Cyclohexane-butyric Acid | 3.33 |
| Fmoc-nva | 0.963 | Fmoc-napala | 0.672 | Cycloheptane-carboxylic Acid | 2.60 |
| Fmoc-NapAla | 0.672 | Fmoc-Phg | 0.483 | Acetic Acid | 2.65 |
| Fmoc-napala | 0.672 | Fmoc-ChAla | 0.943 | Cyclobutane-carboxylic Acid | 2.77 |
| Fmoc-Phg | 0.483 | Fmoc-chala | 0.943 | Cyclopentane-carboxylic Acid | 3.03 |
| Fmoc-ChAla | 0.943 | | | 3-Cyclopentyl-propionic Acid | 3.71 |
| Fmoc-chala | 0.943 | | | Cyclohexane-propionic Acid | 2.80 |
| | | | | 4-Methyl-1-cyclohexane-carboxylic Acid | 5.92 |
| | | | | 4-tert-Butyl-cyclohexane-carboxylic Acid | 6.64 |
| | | | | 1-Adamantane-acetic Acid | 11.16 |
| | | | | 3,3-Diphenyl-propionic Acid | 2.80 |
| | | | | Dicyclohexyl-acetic Acid | 1.00 |
| | | | | Indole-3-acetic Acid | 1.16 |
| | | | | 1-Napthyl-acetic Acid | 3.00 |
| | | | | 3-(3,4,5)-Tri-methoxyphenyl-propionic Acid | 2.00 |
| | | | | 2-Norbornane-acetic Acid | 3.00 |
| | | | | Cyclopentyl-acetic Acid | 1.00 |
| | | | | 2-Ethylbutyric Acid | 1.50 |

A. Typical procedure for the first Fmoc-amino acid mixture coupling.

p-Methylbenzydrylamine (MBHA; 100 mg) resin (1.0 meq/g, 100–200 mesh) was contained within a sealed polypropylene mesh packet. Following neutralization with 5% diisopropylethylamine (DIEA) in dichloromethane (DCM; 3×5 mL), the resin was washed with DCM (3×5 mL). A 0.5M solution of mixed Fmoc amino acids in DMF (1.2 mL) at a predetermined molar ratio (6×, 0.6 meq total), 1.2 mL 0.5M 1-hydroxybenzotriazole (HOBt, 6×, 0.6 meq) in DMF, and 1.2 mL 0.5M diisopropylcarbodiimide (DIPCDI, 6×, 0.6 meq) in DMF were prereacted for 15 minutes for a final concentration of each of 0.167M. The resin packet was then added to the solution and permitted to react for 120 minutes. Following the reaction, the solution was decanted and the resin washed with DMF (3×5 mL).

B. Typical procedure for the second Fmoc-amino acid mixture coupling.

Following deprotection as discussed before, the resin packet was neutralized with 5% diisopropylethylamine (DIEA) in dichloromethane (DCM) (3×5 mL) and then washed with DCM (3×5 mL). A 0.5M solution of mixed Fmoc amino acids in DMF (1.2 mL) at a predetermined molar ratio (6×, 0.6 meq total), 1.2 mL 0.5M 1-hydroxybenzotriazole (HOBt, 6×, 0.6 meq) in DMF, and 1.2 mL 0.5M diisopropylcarbodiimide (DIPCDI, 6×, 0.6 meq) in DMF were prereacted for 15 minutes for a final concentration of each of 0.167M. The resin packet was then added to the solution and permitted to react for 120 minutes. Following the reaction, the solution was decanted and the resin washed with DMF (3×5 mL).

C. Typical procedure for a carboxylic acid mixture coupling.

Following deprotection, the resin packet was neutralized with 5% diisopropylethylamine (DIEA) in dichloromethane (DCM)(3×5 mL) and then washed with DCM (3×5 mL). A 0.5M solution of carboxylic acids in DMF (2.0 mL) at a predetermined molar ratio (10×, 1.0 meq total), 2.0 mL 0.5M 1-hydroxybenzotriazole (HOBt, 10×, 1.0 meq) in DMF, and 2.0 mL 0.5M diisopropylcarbodiimide (DIPCDI, 10×, 1.0 meq) in DMF was prereacted for 15 minutes for a final concentration of each of 0.167M. The resin packet was then added to the solution and permitted to react for 120 minutes. Following the reaction, the solution was decanted and the resin washed with DMF (3×5 mL).

N-Alkylations on the resin-bound peptides and peptide mixtures were carried out as described in Examples 1 and 2 for the individual compounds. Reductions of the resin-bound N-acylated and N-alkylated peptide mixtures were carried out as discussed in Examples 1 and 2 for the individual compounds. Cyclization reactions and cleavage of the compound libraries on and from the resin were also carried out as described in Examples 1 and 2 for the individual peptides.

These libraries were positional scanning libraries in that each position of $R^1$, $R^3$ and $R^4$ was separately occupied by a single substituent group (O), whereas each of the remaining two positions was occupied by approximately equimolar mixtures of all of the substituent groups used at each position (X and X). In these libraries, 27 amino acids were used at the $R^1$ position, 29 amino acids were used at the $R^3$ position and 40 carboxylic acids were used at the $R^4$ position. Thus, for each of the $R^1$ positions scanned (OXX), there were a mixture of 1080 compounds present (1×27×40). There were 1160 compounds present (29×1×40) for each of the scanned $R^3$ positions (XOX), with 783 compounds being present (29×27×1) in each mixture when the $R^4$ position (XXO) was scanned. The three mixtures provided a total diversity of 31,320 compounds (29×27×40). The various amino acids and carboxylic acids used to prepare these libraries are listed in Tables 5 and 6 hereinafter.

TABLE 5

N-Benzyl-1,4,5-trisubstituted-2,3-diketopiperazine Library

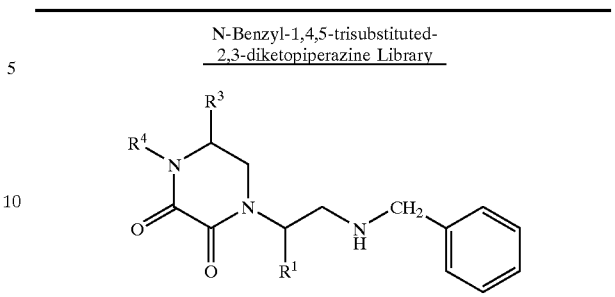

| Pool No. | $R^1$ | $R^3$ | $R^4$ |
|---|---|---|---|
| 1 | Fmoc-Ala | X | X |
| 2 | Fmoc-Phe | X | X |
| 3 | Fmoc-Gly | X | X |
| 4 | Fmoc-Ile | X | X |
| 5 | Fmoc-Lys(Boc) | X | X |
| 6 | Fmoc-Leu | X | X |
| 7 | Fmoc-Met(O) | X | X |
| 8 | Fmoc-Ser(tBut) | X | X |
| 9 | Fmoc-Thr(tBut) | X | X |
| 10 | Fmoc-Val | X | X |
| 11 | Fmoc-Tyr(tBut) | X | X |
| 12 | Fmoc-ala | X | X |
| 13 | Fmoc-phe | X | X |
| 14 | Fmoc-ile | X | X |
| 15 | Fmoc-lys(Boc) | X | X |
| 16 | Fmoc-leu | X | X |
| 17 | Fmoc-ser(tBut) | X | X |
| 18 | Fmoc-thr(tBut) | X | X |
| 19 | Fmoc-val | X | X |
| 20 | Fmoc-tyr(tBut) | X | X |
| 21 | Fmoc-Nle | X | X |
| 22 | Fmoc-nle | X | X |

TABLE 5-continued

N-Benzyl-1,4,5-trisubstituted-2,3-diketopiperazine Library

| Pool No. | $R^1$ | $R^3$ | $R^4$ |
|---|---|---|---|
| 23 | Fmoc-Nva | X | X |
| 24 | Fmoc-nva | X | X |
| 25 | Fmoc-NapAla | X | X |
| 26 | Fmoc-napala | X | X |
| 27 | Fmoc-Phg | X | X |
| 28 | Fmoc-ChAla | X | X |
| 29 | Fmoc-chala | X | X |
| 30 | X | Fmoc-Ala | X |
| 31 | X | Fmoc-Phe | X |
| 32 | X | Fmoc-Gly | X |
| 33 | X | Fmoc-Ile | X |
| 34 | X | Fmoc-Leu | X |
| 35 | X | Fmoc-Met(O) | X |
| 36 | X | Fmoc-Ser(tBut) | X |
| 37 | X | Fmoc-Thr(tBut) | X |
| 38 | X | Fmoc-Val | X |
| 39 | X | Fmoc-Tyr(tBut) | X |
| 40 | X | Fmoc-ala | X |
| 41 | X | Fmoc-phe | X |
| 42 | X | Fmoc-ile | X |
| 43 | X | Fmoc-leu | X |
| 44 | X | Fmoc-ser(tBut) | X |
| 45 | X | Fmoc-thr(tBut) | X |
| 46 | X | Fmoc-val | X |
| 47 | X | Fmoc-tyr(tBut) | X |
| 48 | X | Fmoc-Nle | X |
| 49 | X | Fmoc-nle | X |
| 50 | X | Fmoc-Nva | X |
| 51 | X | Fmoc-nva | X |
| 52 | X | Fmoc-NapAla | X |
| 53 | X | Fmoc-napala | X |
| 54 | X | Fmoc-Phg | X |
| 55 | X | Fmoc-ChAla | X |
| 56 | X | Fmoc-chala | X |
| 57 | X | X | 1-Phenyl-1-cyclopropanecarboxylic Acid |
| 58 | X | X | m-Tolylacetic Acid |
| 59 | X | X | 3-Fluorophenyl acetic Acid |
| 60 | X | X | (α,α,α-Trifluoro-m-tolyl)acetic Acid |
| 61 | X | X | p-Tolylacetic Acid |
| 62 | X | X | 3-Methoxyphenyl-acetic Acid |
| 63 | X | X | 4-Methoxyphenyl-acetic Acid |
| 64 | X | X | 4-Ethoxyphenyl-acetic Acid |
| 65 | X | X | 4-Isobutyl-α-methyl-phenylacetic Acid |
| 66 | X | X | 3,4-Dichloro-phenylacetic Acid |
| 67 | X | X | 3,5-Bis-(trifluoromethyl)phenylacetic Acid |
| 68 | X | X | Phenylacetic Acid |
| 69 | X | X | Hydrocinnamic Acid |

TABLE 5-continued

N-Benzyl-1,4,5-trisubstituted-2,3-diketopiperazine Library

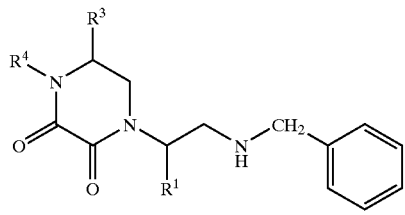

| Pool No. | R¹ | R³ | R⁴ |
|---|---|---|---|
| 70 | X | X | 4-Phenylbutyric Acid |
| 71 | X | X | Butyric Acid |
| 72 | X | X | Heptanoic Acid |
| 73 | X | X | Isobutyric Acid |
| 74 | X | X | Isovaleric Acid |
| 75 | X | X | 4-Methylvaleric Acid |
| 76 | X | X | Trimethylacetic Acid |
| 77 | X | X | tert-Butylacetic Acid |
| 78 | X | X | Cyclohexane-carboxylic Acid |
| 79 | X | X | Cyclohexyl-acetic Acid |
| 80 | X | X | Cyclohexane-butyric Acid |
| 81 | X | X | Cycloheptane-carboxylic Acid |
| 82 | X | X | Acetic Acid |
| 83 | X | X | Cyclobutane-carboxylic Acid |
| 84 | X | X | Cyclopentane-carboxylic Acid |
| 85 | X | X | Cyclohexane-propionic Acid |
| 86 | X | X | 4-Methyl-1-cyclohexanecarboxylic Acid |
| 87 | X | X | 4-tert-Butyl-cyclohexanecarboxylic Acid |
| 88 | X | X | 1-Adamantane-acetic Acid |
| 89 | X | X | 3-3-Diphenyl-propionic Acid |
| 90 | X | X | Dicyclohexyl-acetic Acid |
| 91 | X | X | Indole-3-acetic Acid |
| 92 | X | X | 1-Naphthylacetic Acid |
| 93 | X | X | 3-(3,4,5)-Trimethoxyphenyl propionic Acid |
| 94 | X | X | 2-Norbornane-acetic Acid |
| 95 | X | X | Cyclopentyl acetic Acid |
| 96 | X | X | 2-Ethylbutyric Acid |

TABLE 6

N-Methyl-1,4,5-trisubstituted-2,3-diketopiperazine Library

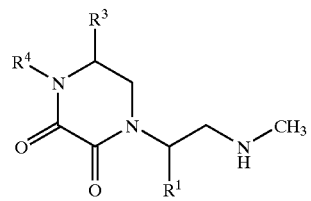

| Pool No. | R¹ | R³ | R⁴ |
|---|---|---|---|
| 1 | Fmoc-Ala | X | X |
| 2 | Fmoc-Phe | X | X |
| 3 | Fmoc-Gly | X | X |
| 4 | Fmoc-Ile | X | X |
| 5 | Fmoc-Lys(Boc) | X | X |
| 6 | Fmoc-Leu | X | X |
| 7 | Fmoc-Met(O) | X | X |
| 8 | Fmoc-Ser(tBut) | X | X |
| 9 | Fmoc-Thr(tBut) | X | X |
| 10 | Fmoc-Val | X | X |
| 11 | Fmoc-Tyr(tBut) | X | X |
| 12 | Fmoc-ala | X | X |
| 13 | Fmoc-phe | X | X |
| 14 | Fmoc-ile | X | X |
| 15 | Fmoc-lys(Boc) | X | X |
| 16 | Fmoc-leu | X | X |
| 17 | Fmoc-ser(tBut) | X | X |
| 18 | Fmoc-thr(tBut) | X | X |
| 19 | Fmoc-val | X | X |
| 20 | Fmoc-tyr(tBut) | X | X |
| 21 | Fmoc-Nle | X | X |
| 22 | Fmoc-nle | X | X |
| 23 | Fmoc-Nva | X | X |
| 24 | Fmoc-nva | X | X |
| 25 | Fmoc-NapAla | X | X |
| 26 | Fmoc-napala | X | X |
| 27 | Fmoc-Phg | X | X |
| 28 | Fmoc-ChAla | X | X |
| 29 | Fmoc-chala | X | X |
| 30 | X | Fmoc-Ala | X |
| 31 | X | Fmoc-Phe | X |
| 32 | X | Fmoc-Gly | X |
| 33 | X | Fmoc-Ile | X |
| 34 | X | Fmoc-Leu | X |
| 35 | X | Fmoc-Met(O) | X |
| 36 | X | Fmoc-Ser(tBut) | X |
| 37 | X | Fmoc-Thr(tBut) | X |
| 38 | X | Fmoc-Val | X |
| 39 | X | Fmoc-Tyr(tBut) | X |
| 40 | X | Fmoc-ala | X |
| 41 | X | Fmoc-phe | X |
| 42 | X | Fmoc-ile | X |
| 43 | X | Fmoc-leu | X |
| 44 | X | Fmoc-ser(tBut) | X |
| 45 | X | Fmoc-thr(tBut) | X |
| 46 | X | Fmoc-val | X |
| 47 | X | Fmoc-tyr(tBut) | X |
| 48 | X | Fmoc-Nle | X |
| 49 | X | Fmoc-nle | X |
| 50 | X | Fmoc-Nva | X |
| 51 | X | Fmoc-nva | X |
| 52 | X | Fmoc-NapAla | X |
| 53 | X | Fmoc-napala | X |
| 54 | X | Fmoc-Phg | X |
| 55 | X | Fmoc-ChAla | X |
| 56 | X | Fmoc-chala | X |

TABLE 6-continued

N-Methyl-1,4,5-trisubstituted-2,3-diketopiperazine Library

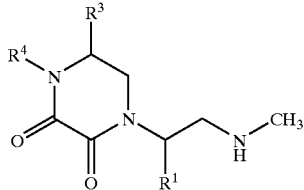

| Pool No. | $R^1$ | $R^3$ | $R^4$ |
|---|---|---|---|
| 57 | X | X | 1-Phenyl-1-cyclopropanecarboxylic Acid |
| 58 | X | X | m-Tolylacetic Acid |
| 59 | X | X | 3-Fluorophenylacetic Acid |
| 60 | X | X | (α,α,α-Trifluoro-m-tolyl)acetic Acid |
| 61 | X | X | p-Tolylacetic Acid |
| 62 | X | X | 3-Methoxyphenylacetic Acid |
| 63 | X | X | 4-Methoxyphenylacetic Acid |
| 64 | X | X | 4-Ethoxyphenylacetic Acid |
| 65 | X | X | 4-Isobutyl-α-methylphenylacetic Acid |
| 66 | X | X | 3,4-Dichlorophenylacetic Acid |
| 67 | X | X | 3,5-Bis-(trifluoromethyl)phenylacetic Acid |
| 68 | X | X | Phenylacetic Acid |
| 69 | X | X | Hydrocinnamic Acid |
| 70 | X | X | 4-Phenylbutyric Acid |
| 71 | X | X | Butyric Acid |
| 72 | X | X | Heptanoic Acid |
| 73 | X | X | Isobutyric Acid |
| 74 | X | X | Isovaleric Acid |
| 75 | X | X | 4-Methylvaleric Acid |
| 76 | X | X | Trimethylacetic Acid |
| 77 | X | X | tert-Butylacetic Acid |
| 78 | X | X | Cyclohexanecarboxylic Acid |
| 79 | X | X | Cyclohexylacetic Acid |
| 80 | X | X | Cyclohexanebutyric Acid |
| 81 | X | X | Cycloheptanecarboxylic Acid |
| 82 | X | X | Acetic Acid |
| 83 | X | X | Cyclobutanecarboxylic Acid |
| 84 | X | X | Cyclopentanecarboxylic Acid |
| 85 | X | X | Cyclohexanepropionic Acid |
| 86 | X | X | 4-Methyl-1-cyclohexanecarboxylic Acid |
| 87 | X | X | 4-tert-Butyl-cyclohexanecarboxylic Acid |
| 88 | X | X | 1-Adamantaneacetic Acid |
| 89 | X | X | 3-3-Diphenylpropionic Acid |
| 90 | X | X | Dicyclohexylacetic Acid |
| 91 | X | X | Indole-3-acetic Acid |
| 92 | X | X | 1-Naphthylacetic Acid |

TABLE 6-continued

N-Methyl-1,4,5-trisubstituted-2,3-diketopiperazine Library

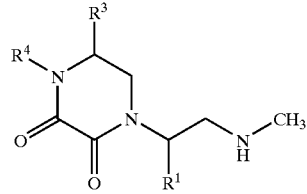

| Pool No. | $R^1$ | $R^3$ | $R^4$ |
|---|---|---|---|
| 93 | X | X | 3-(3,4,5)-Trimethoxyphenyl propionic Acid |
| 94 | X | X | 2-Norbornaneacetic Acid |
| 95 | X | X | Cyclopentyl acetic Acid |
| 96 | X | X | 2-Ethylbutyric Acid |

EXAMPLE 4

Preparation of Individual N-methyl-trisubstituted-5,7-diketo-1,4-diazacycloheptane Compounds and Library A series of individual N-methyl-trisubstituted-5,7-diketo-1,4-diazacycloheptane compounds was prepared as discussed in Examples 1 and 2. The amino acids and carboxylic acids used to prepare these individual compounds are enumerated in Table 7, below.

TABLE 7

Individual N-Methyl-trisubstituted 5,7-diketo-1,4-diazacycloheptane Compounds Synthesized

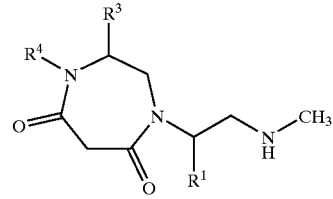

| Prep | $R^1$ | $R^3$ | $R^4$ |
|---|---|---|---|
| 01 | Fmoc-Ala | Fmoc-Phe | Phenylacetic Acid |
| 02 | Fmoc-Phe | Fmoc-Phe | Phenylacetic Acid |
| 03 | Fmoc-Gly | Fmoc-Phe | Phenylacetic Acid |
| 04 | Fmoc-Ile | Fmoc-Phe | Phenylacetic Acid |
| 05 | Fmoc-Lys(Boc) | Fmoc-Phe | Phenylacetic Acid |
| 06 | Fmoc-Leu | Fmoc-Phe | Phenylacetic Acid |
| 07 | Fmoc-Met(O) | Fmoc-Phe | Phenylacetic Acid |
| 08 | Fmoc-Ser(tBut) | Fmoc-Phe | Phenylacetic Acid |
| 09 | Fmoc-Thr(tBut) | Fmoc-Phe | Phenylacetic Acid |
| 10 | Fmoc-Val | Fmoc-Phe | Phenylacetic Acid |
| 11 | Fmoc-Tyr(tBut) | Fmoc-Phe | Phenylacetic Acid |
| 12 | Fmoc-ala | Fmoc-Phe | Phenylacetic Acid |
| 13 | Fmoc-phe | Fmoc-Phe | Phenylacetic Acid |
| 14 | Fmoc-ile | Fmoc-Phe | Phenylacetic Acid |
| 15 | Fmoc-Iys(Boc) | Fmoc-Phe | Phenylacetic Acid |
| 16 | Fmoc-leu | Fmoc-Phe | Phenylacetic Acid |
| 17 | Fmoc-ser(tBut) | Fmoc-Phe | Phenylacetic Acid |
| 18 | Fmoc-thr(tBut) | Fmoc-Phe | Phenylacetic Acid |

TABLE 7-continued

Individual N-Methyl-trisubstituted 5,7-diketo-1,4-diazacycloheptane Compounds Synthesized

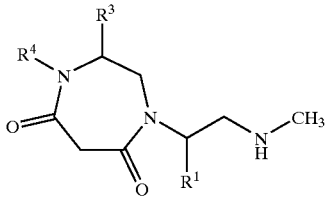

| Prep | R¹ | R³ | R⁴ |
|---|---|---|---|
| 19 | Fmoc-val | Fmoc-Phe | Phenylacetic Acid |
| 20 | Fmoc-tyr(tBut) | Fmoc-Phe | Phenylacetic Acid |
| 21 | Fmoc-Nle | Fmoc-Phe | Phenylacetic Acid |
| 22 | Fmoc-nle | Fmoc-Phe | Phenylacetic Acid |
| 23 | Fmoc-Nva | Fmoc-Phe | Phenylacetic Acid |
| 24 | Fmoc-nva | Fmoc-Phe | Phenylacetic Acid |
| 25 | Fmoc-NapAla | Fmoc-Phe | Phenylacetic Acid |
| 26 | Fmoc-napala | Fmoc-Phe | Phenylacetic Acid |
| 27 | Fmoc-Phg | Fmoc-Phe | Phenylacetic Acid |
| 28 | Fmoc-ChAla | Fmoc-Phe | Phenylacetic Acid |
| 29 | Fmoc-chala | Fmoc-Phe | Phenylacetic Acid |
| 30 | Fmoc-Phe | Fmoc-Ala | Phenylacetic Acid |
| 31 | Fmoc-Phe | Fmoc-Phe | Phenylacetic Acid |
| 32 | Fmoc-Phe | Fmoc-Gly | Phenylacetic Acid |
| 33 | Fmoc-Phe | Fmoc-ile | Phenylacetic Acid |
| 34 | Fmoc-Phe | Fmoc-Leu | Phenylacetic Acid |
| 35 | Fmoc-Phe | Fmoc-Met(O) | Phenylacetic Acid |
| 36 | Fmoc-Phe | Fmoc-Ser(tBut) | Phenylacetic Acid |
| 37 | Fmoc-Phe | Fmoc-Thr(tBut) | Phenylacetic Acid |
| 38 | Fmoc-Phe | Fmoc-Val | Phenylacetic Acid |
| 39 | Fmoc-Phe | Fmoc-Tyr(tBut) | Phenylacetic Acid |
| 40 | Fmoc-Phe | Fmoc-ala | Phenylacetic Acid |
| 41 | Fmoc-Phe | Fmoc-phe | Phenylacetic Acid |
| 42 | Fmoc-Phe | Fmoc-ile | Phenylacetic Acid |
| 43 | Fmoc-Phe | Fmoc-leu | Phenylacetic Acid |
| 44 | Fmoc-Phe | Fmoc-ser(tBut) | Phenylacetic Acid |
| 45 | Fmoc-Phe | Fmoc-thr(tBut) | Phenylacetic Acid |
| 46 | Fmoc-Phe | Fmoc-val | Phenylacetic Acid |
| 47 | Fmoc-Phe | Fmoc-tyr(tBut) | Phenylacetic Acid |
| 48 | Fmoc-Phe | Fmoc-Nle | Phenylacetic Acid |
| 49 | Fmoc-Phe | Fmoc-nle | Phenylacetic Acid |
| 50 | Fmoc-Phe | Fmoc-Nva | Phenylacetic Acid |
| 51 | Fmoc-Phe | Fmoc-nva | Phenylacetic Acid |
| 52 | Fmoc-Phe | Fmoc-NapAla | Phenylacetic Acid |
| 53 | Fmoc-Phe | Fmoc-napala | Phenylacetic Acid |
| 54 | Fmoc-Phe | Fmoc-Phg | Phenylacetic Acid |
| 55 | Fmoc-Phe | Fmoc-ChAla | Phenylacetic Acid |
| 56 | Fmoc-Phe | Fmoc-chala | Phenylacetic Acid |
| 57 | Fmoc-Phe | Fmoc-Phe | 1-Phenyl-1-cyclopropanecarboxylic Acid |
| 58 | Fmoc-Phe | Fmoc-Phe | m-Tolylacetic Acid |
| 59 | Fmoc-Phe | Fmoc-Phe | 3-Fluorophenylacetic Acid |
| 60 | Fmoc-Phe | Fmoc-Phe | (α,α,α-Trifluoro-m-tolyl)acetic Acid |
| 61 | Fmoc-Phe | Fmoc-Phe | p-Tolylacetic Acid |
| 62 | Fmoc-Phe | Fmoc-Phe | 3-Methoxyphenylacetic Acid |
| 63 | Fmoc-Phe | Fmoc-Phe | 4-Methoxyphenylacetic Acid |
| 64 | Fmoc-Phe | Fmoc-Phe | 4-Ethoxyphenylacetic Acid |
| 65 | Fmoc-Phe | Fmoc-Phe | 4-Isobutyl-α-methylphenylacetic Acid |
| 66 | Fmoc-Phe | Fmoc-Phe | 3,4-Dichlorophenylacetic Acid |

TABLE 7-continued

Individual N-Methyl-trisubstituted 5,7-diketo-1,4-diazacycloheptane Compounds Synthesized

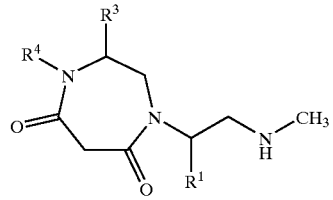

| Prep | R¹ | R³ | R⁴ |
|---|---|---|---|
| 67 | Fmoc-Phe | Fmoc-Phe | 3,5-Bis(trifluoromethyl)phenylacetic Acid |
| 68 | Fmoc-Phe | Fmoc-Phe | Phenylacetic Acid |
| 69 | Fmoc-Phe | Fmoc-Phe | Hydrocinnamic Acid |
| 70 | Fmoc-Phe | Fmoc-Phe | 4-Phenylbutyric Acid |
| 71 | Fmoc-Phe | Fmoc-Phe | Butyric Acid |
| 72 | Fmoc-Phe | Fmoc-Phe | Heptanoic Acid |
| 73 | Fmoc-Phe | Fmoc-Phe | Isobutyric Acid |
| 74 | Fmoc-Phe | Fmoc-Phe | Isovaleric Acid |
| 75 | Fmoc-Phe | Fmoc-Phe | 4-Methylvaleric Acid |
| 76 | Fmoc-Phe | Fmoc-Phe | Trimethylacetic Acid |
| 77 | Fmoc-Phe | Fmoc-Phe | tert-Butylacetic Acid |
| 78 | Fmoc-Phe | Fmoc-Phe | Cyclohexanecarboxylic Acid |
| 79 | Fmoc-Phe | Fmoc-Phe | Cyclohexylacetic Acid |
| 80 | Fmoc-Phe | Fmoc-Phe | Cyclohexanebutyric Acid |
| 81 | Fmoc-Phe | Fmoc-Phe | Cycloheptanecarboxylic Acid |
| 82 | Fmoc-Phe | Fmoc-Phe | Acetic Acid |
| 83 | Fmoc-Phe | Fmoc-Phe | Cyclobutanecarboxylic Acid |
| 84 | Fmoc-Phe | Fmoc-Phe | Cyclopentanecarboxylic Acid |
| 85 | Fmoc-Phe | Fmoc-Phe | Cyclohexanepropionic Acid |
| 86 | Fmoc-Phe | Fmoc-Phe | 4-Methyl-1-cyclohexanecarboxylic Acid |
| 87 | Fmoc-Phe | Fmoc-Phe | 4-tert-Butyl-cyclohexanecarboxylic Acid |
| 88 | Fmoc-Phe | Fmoc-Phe | 1-Adamantaneacetic Acid |
| 89 | Fmoc-Phe | Fmoc-Phe | 3-3-diphenyl propionic Acid |
| 90 | Fmoc-Phe | Fmoc-Phe | Dicyclohexylacetic Acid |
| 91 | Fmoc-Phe | Fmoc-Phe | Indole-3-acetic Acid |
| 92 | Fmoc-Phe | Fmoc-Phe | 1-Naphthyl acetic Acid |
| 93 | Fmoc-Phe | Fmoc-Phe | 3-(3,4,5)-Trimethoxyphenylpropionic Acid |
| 94 | Fmoc-Phe | Fmoc-Phe | 2-Norbornaneacetic Acid |
| 95 | Fmoc-Phe | Fmoc-Phe | Cyclopentylacetic Acid |
| 96 | Fmoc-Phe | Fmoc-Phe | 2-Ethyl butyric Acid |

A library of N-methyl-trisubstituted-5,7-diketo-1,4-diazacycloheptane compounds was also prepared in a manner similar to that discussed for Example 3, except that malonyl dichloride as the ring-forming a reagent. The amino acids and carboxylic acids used to prepare the compound pools of this library are shown in Table 8, below.

TABLE 8

N-Methyl-trisubstituted-5,7-diketo-1,4-diazacycloheptane Compound Library

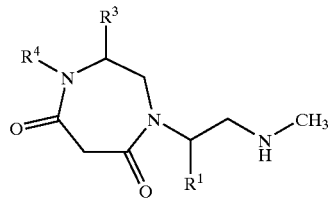

| Pool No. | R¹ | R³ | R⁴ |
|---|---|---|---|
| 1 | Fmoc-Ala | X | X |
| 2 | Fmoc-Phe | X | X |
| 3 | Fmoc-Gly | X | X |
| 4 | Fmoc-Ile | X | X |
| 5 | Fmoc-Lys(Boc) | X | X |
| 6 | Fmoc-Leu | X | X |
| 7 | Fmoc-Met(O) | X | X |
| 8 | Fmoc-Ser(tBut) | X | X |
| 9 | Fmoc-Thr(tBut) | X | X |
| 10 | Fmoc-Val | X | X |
| 11 | Fmoc-Tyr(tBut) | X | X |
| 12 | Fmoc-ala | X | X |
| 13 | Fmoc-phe | X | X |
| 14 | Fmoc-ile | X | X |
| 15 | Fmoc-lys(Boc) | X | X |
| 16 | Fmoc-leu | X | X |
| 17 | Fmoc-ser(tBut) | X | X |
| 18 | Fmoc-thr(tBut) | X | X |
| 19 | Fmoc-val | X | X |
| 20 | Fmoc-tyr(tBut) | X | X |
| 21 | Fmoc-Nle | X | X |
| 22 | Fmoc-nle | X | X |
| 23 | Fmoc-Nva | X | X |
| 24 | Fmoc-nva | X | X |
| 25 | Fmoc-NapAla | X | X |
| 26 | Fmoc-napala | X | X |
| 27 | Fmoc-Phg | X | X |
| 28 | Fmoc-ChAla | X | X |
| 29 | Fmoc-chala | X | X |
| 30 | X | Fmoc-Ala | X |
| 31 | X | Fmoc-Phe | X |
| 32 | X | Fmoc-Gly | X |
| 33 | X | Fmoc-Ile | X |
| 34 | X | Fmoc-Leu | X |
| 35 | X | Fmoc-Met(O) | X |
| 36 | X | Fmoc-Ser(tBut) | X |
| 37 | X | Fmoc-Thr(tBut) | X |
| 38 | X | Fmoc-Val | X |
| 39 | X | Fmoc-Tyr(tBut) | X |
| 40 | X | Fmoc-ala | X |
| 41 | X | Fmoc-phe | X |
| 42 | X | Fmoc-ile | X |
| 43 | X | Fmoc-leu | X |
| 44 | X | Fmoc-ser(tBut) | X |
| 45 | X | Fmoc-thr(tBut) | X |
| 46 | X | Fmoc-val | X |
| 47 | X | Fmoc-tyr(tBut) | X |
| 48 | X | Fmoc-Nle | X |
| 49 | X | Fmoc-nle | X |
| 50 | X | Fmoc-Nva | X |
| 51 | X | Fmoc-nva | X |
| 52 | X | Fmoc-NapAla | X |
| 53 | X | Fmoc-napala | X |
| 54 | X | Fmoc-Phg | X |
| 55 | X | Fmoc-ChAla | X |
| 56 | X | Fmoc-chala | X |
| 57 | X | X | 1-Phenyl-1-cyclopropanecarboxylic Acid |
| 58 | X | X | m-Tolylacetic Acid |
| 59 | X | X | 3-Fluorophenylacetic Acid |
| 60 | X | X | (α,α,α-Trifluoro-m-tolyl)acetic Acid |
| 61 | X | X | p-Tolylacetic Acid |
| 62 | X | X | 3-Methoxyphenylacetic Acid |
| 63 | X | X | 4-Methoxyphenylacetic Acid |
| 64 | X | X | 4-Ethoxyphenylacetic Acid |
| 65 | X | X | 4-Isobutyl-α-methylphenylacetic Acid |
| 66 | X | X | 3,4-Dichlorophenylacetic Acid |
| 67 | X | X | 3,5-Bis-(trifluoromethyl)phenylacetic Acid |
| 68 | X | X | Phenylacetic Acid |
| 69 | X | X | Hydrocinnamic Acid |
| 70 | X | X | 4-Phenylbutyric Acid |
| 71 | X | X | Butyric Acid |
| 72 | X | X | Heptanoic Acid |
| 73 | X | X | Isobutyric Acid |
| 74 | X | X | Isovaleric Acid |
| 75 | X | X | 4-Methylvaleric Acid |
| 76 | X | X | Trimethylacetic Acid |
| 77 | X | X | tert-Butylacetic Acid |
| 78 | X | X | Cyclohexanecarboxylic Acid |
| 79 | X | X | Cyclohexylacetic Acid |
| 80 | X | X | Cyclohexanebutyric Acid |
| 81 | X | X | Cycloheptanecarboxylic Acid |
| 82 | X | X | Acetic Acid |
| 83 | X | X | Cyclobutanecarboxylic Acid |
| 84 | X | X | Cyclopentanecarboxylic Acid |
| 85 | X | X | Cyclohexanepropionic Acid |
| 86 | X | X | 4-Methyl-1-cyclohexanecarboxylic Acid |
| 87 | X | X | 4-tert-Butyl-cyclohexanecarboxylic Acid |
| 88 | X | X | 1-Adamantaneacetic Acid |
| 89 | X | X | 3-3-Diphenylpropionic Acid |
| 90 | X | X | Dicyclohexylacetic Acid |

TABLE 8-continued

N-Methyl-trisubstituted-5,7-diketo-1,4-diazacycloheptane Compound Library

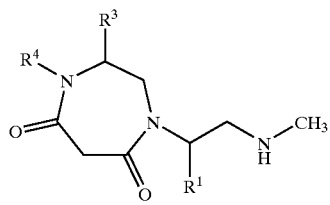

| Pool No. | $R^1$ | $R^3$ | $R^4$ |
|---|---|---|---|
| 91 | X | X | Indole-3-acetic Acid |
| 92 | X | X | 1-Naphthylacetic Acid |
| 93 | X | X | 3-(3,4,5)-Trimethoxy-phenylpropionic Acid |
| 94 | X | X | 2-Norbornane-acetic Acid |
| 95 | X | X | Cyclopentyl acetic Acid |
| 96 | X | X | 2-Ethylbutyric Acid |

EXAMPLE 5

Preparation of Compounds with Additional Cyclizing Reagents

A series of ninety-nine individual compounds was prepared using eleven reagents for forming N-methylamino-substituted cyclic bis-amide and bis-amine compounds. The cyclization reactions from common N-methylated indermediate compound 5 of Scheme 1 are illustrated in Schemes 6 and 7, below. The amino acids and carboxylic acids used to form the $R^1$, $R^3$ and $R^4$ substituents are shown in Table 9 below.

TABLE 9

Components of Intermediates 5 for Synthesis of Ninty-nine Individual Compounds

| $R^1$ | $R^3$ | $R^4$ |
|---|---|---|
| Phe | Phe | Phenylacetic Acid |
| Val | Phe | Phenylacetic Acid |
| Leu | Phe | Phenylacetic Acid |
| Phe | Gly | Phenylacetic Acid |
| Val | Gly | Phenylacetic Acid |
| Leu | Gly | Phenylacetic Acid |
| Phe | Leu | Phenylacetic Acid |
| Val | Leu | Phenylacetic Acid |
| Leu | Leu | Phenylacetic Acid |

Scheme 6

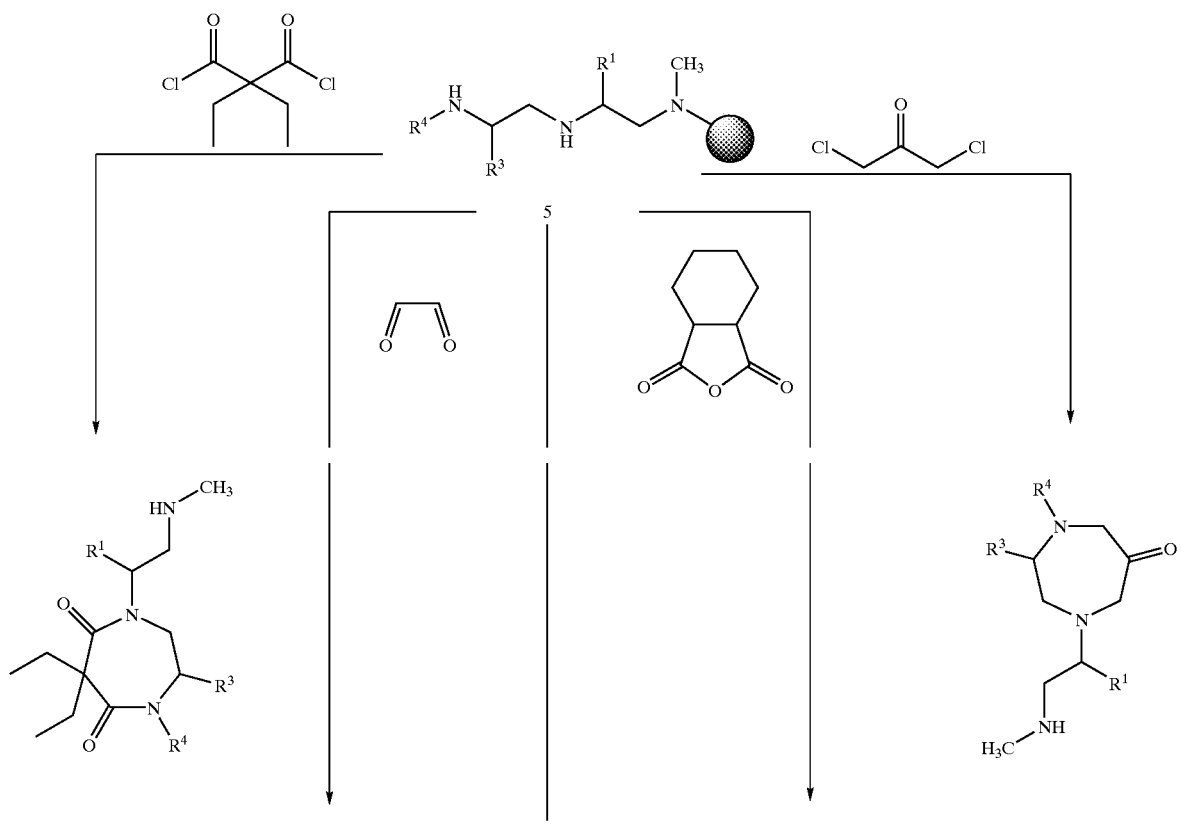

61 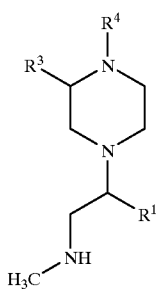 62 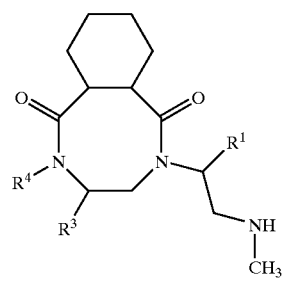
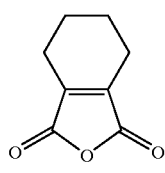
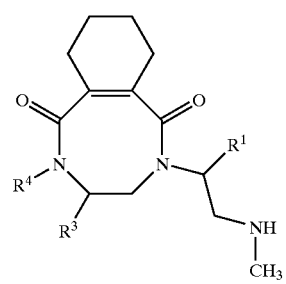
Scheme 7
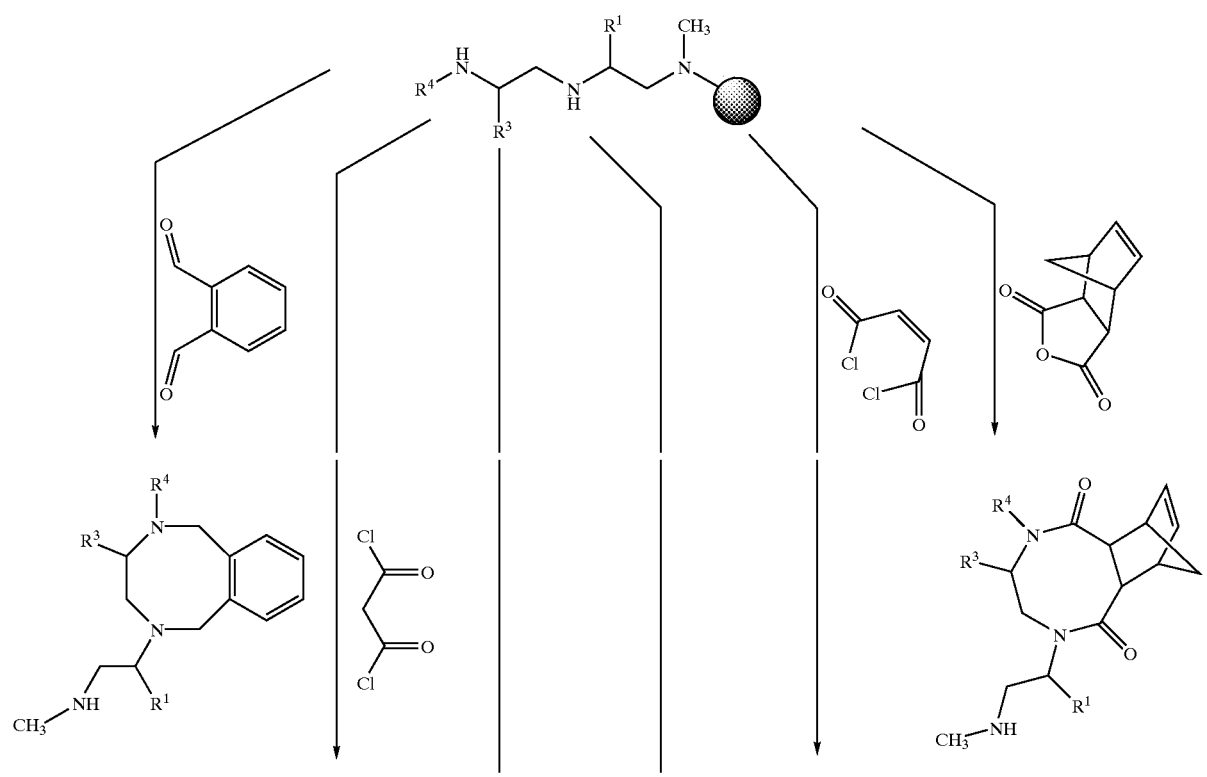

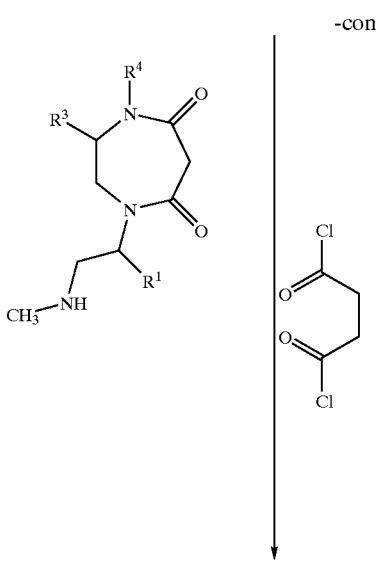
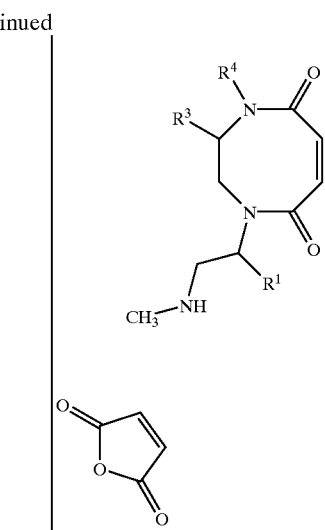

EXAMPLE 6

Orphanin Binding Screen Using the N-Benzyl-1,4, 5-trisubstituted-2,3-diketopiperazine Library A (para-iodo-Phe[1],para-iodo-Phe[4]-) Orphanin FQ analogue was synthesized on the COMPASS multiple peptide synthesizer (Spyder, San Diego, Calif.). Tritiation of the iodo-compound was performed at the National Tritium Labeling Facility (Berkeley, Calif.). The ditritio-compound was obtained through hydrogen exchange in the presence of a catalyst. The diiodopeptide (5 mg), dissolved in 1 mL of N,N-dimethylformamide (DMF), was exposed to tritium gas in the presence of 3 mg of palladium oxide. The reaction was allowed to proceed for two hours, after which the gas flow was discontinued and 2 mLs of methanol were added to the reaction mixture to exchange unreacted tritium. The resulting mixture was passed through Teflon filters (PTFE), which were rinsed with 50% aqueous DMF. The eluent was lyophilized to dryness overnight (about 18 hours). The tritiated peptide was purified by RP-HPLC. The radiolabeled peptide was found to have a specific activity of 33 Ci/mmole.

Frozen rat brains (Harlan, Indianapolis, Ind.) were defrosted in Tris buffer [50 mM Tris, 2 mM EDTA, 100 M phenylmethylsulphonylfluoride (PMSF), pH 7.4]. Individual brains, minus cerebella, were homogenized in 40 mLs of buffer in a glass Dounce homogenizer. Homogenates were spun for 10 minutes at 38,000 g (Beckmann H2-JC, Fullerton, Calif.). Pellets were resuspended in fresh buffer. The suspension was incubated at 37° C. for 30 minutes, and centrifuged for 10 minutes. Pellets were resuspended in 100 volumes of buffer. Samples were removed for protein concentration determinations using the method described by Bradford, *Anal. Biochem.*, 72:248 (1976) and bovine serum albumin as the standard. Bovine serum albumin (2 mg/mL) was added to the final suspension.

For association studies, each assay tube contained a final concentration of 1.8 nM [$^3$H$_2$]-Orphanin FQ, 1 mL of membrane suspension in a total volume of 1.1 mLs. The non-radiolabeled peptide (5 μM) was used to determine nonspecific binding. Assays were incubated at 25 C for time periods ranging from 5–30 minutes. The assay was performed twice. The reaction was terminated by filtration through GF-B filters using a Brandell Harvester (Gaithersberg, Mass.) The filters had been previously soaked in 0.1% polyethyleneimine for one hour to reduce nonspecific binding. Filters were washed with 12 mL/sample Tris buffer at 4° C. Bound radioactivity was counted on a Beckmann Liquid Scintillation Counter (Fullerton, Calif.) and expressed in counts per minute. Saturation curves were obtained by incubating (2 hours) [$^3$H$_2$]-Orphanin FQ at 10 different concentrations from 0.7–27 nM in a final volume of 0.65 mL.

Nonspecific binding was determined in the presence of 5 μM Orphanin FQ. Saturation studies were carried out using four replicates, and the assay was repeated three times. The reaction was terminated by filtration through GF-B filters, previously soaked in 0.1% polyethyleneimine, using a Tomtec 96 harvester (Orange, Conn.). Filters were washed with 6 mL/sample Tris buffer at 4° C. Bound radioactivity was counted on a Pharmacia Biotech Beta-plate Liquid Scintillation Counter (Piscataway, N.J.) and expressed in counts per minute. Competition assays were performed as described for saturation studies. Standards for competition curves were obtained using cold competitor (Orphanin FQ) at seven different concentrations ranging from 0.009–9,000 nM. $IC_{50}$ values were determined using six concentrations of each peptide analog.

Competition studies were carried out in the presence of 3 nM [$^3H_2$]-Orphanin FQ. Competition studies were carried out using two replicates, and the assay was repeated four times. Dissociation constants (Kd), the maximum binding capacities (Bmax), and $IC_{50}$ values were calculated using EBDA and LIGAND [Munson et al., *Anal. Biochem.*, 107:220(1980)] or Graphpad/Prizm (ISI, San Diego, Calif.).

Results of these binding studies for the N-benzyl-1,4,5-trisubstituted-2,3-diketopiperazine library are provided in Table 10, below, with the data being shown in terms of the mean binding result (mean), the non-specific binding result that is subtracted from the mean (less NSB) and the value of 1/(percent bound) for each library pool of compounds. An "X" in the Table indicates that the particular R group is comprised of a mixture of the several amino acid side chains or carboxylic acid chains used in preparation of the library.

TABLE 10

N-Benzyl-1,4,5-trisubstituted-2,3-diketopiperazine Library
Orphanin Binding Inhibition Assay

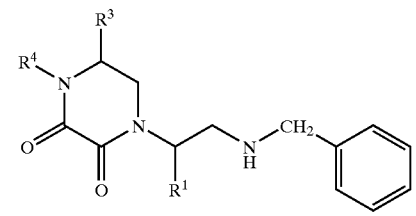

| Pool No. | $R^1$ | $R^3$ | $R^4$ | Mean | Minus NSB | 1% Bound |
|---|---|---|---|---|---|---|
| 1 | Fmoc-Ala | X | X | 2821.1 | 2212.10 | 0.010 |
| 2 | Fmoc-Phe | X | X | 2251 | 1642.00 | 0.014 |
| 3 | Fmoc-Gly | X | X | 2282.65 | 1673.65 | 0.014 |
| 4 | Fmoc-Ile | X | X | 2760.6 | 2151.60 | 0.011 |
| 5 | Fmoc-Lys(Boc) | X | X | 2079.55 | 1470.55 | 0.015 |
| 6 | Fmoc-Leu | X | X | 2450.9 | 1841.90 | 0.012 |
| 7 | Fmoc-Met(O) | X | X | 2738.05 | 2129.05 | 0.011 |
| 8 | Fmoc-Ser(tBut) | X | X | 2717.85 | 2108.85 | 0.011 |
| 9 | Fmoc-Thr(tBut) | X | X | 3005.05 | 2396.05 | 0.009 |
| 10 | Fmoc-Val | X | X | 2896.05 | 2287.05 | 0.010 |
| 11 | Fmoc-Tyr(tBut) | X | X | 2873.9 | 2264.90 | 0.010 |
| 12 | Fmoc-ala | X | X | 2641.25 | 2032.25 | 0.011 |
| 13 | Fmoc-phe | X | X | 1702.05 | 1093.05 | 0.021 |
| 14 | Fmoc-ile | X | X | 2817.15 | 2208.15 | 0.010 |
| 15 | Fmoc-lys(Boc) | X | X | 1527.9 | 918.90 | 0.025 |
| 16 | Fmoc-leu | X | X | 2460.35 | 1851.35 | 0.012 |
| 17 | Fmoc-ser(tBut) | X | X | 3003.65 | 2394.65 | 0.009 |
| 18 | Fmoc-thr(tBut) | X | X | 3047 | 2438.00 | 0.009 |
| 19 | Fmoc-val | X | X | 2363.25 | 1754.25 | 0.013 |
| 20 | Fmoc-tyr(tBut) | X | X | 2495.95 | 1886.95 | 0.012 |
| 21 | Fmoc-Nle | X | X | 2757.6 | 2148.60 | 0.011 |
| 22 | Fmoc-nle | X | X | 2615.25 | 2006.25 | 0.011 |
| 23 | Fmoc-Nva | X | X | 3077.7 | 2468.70 | 0.009 |
| 24 | Fmoc-nva | X | X | 2565.9 | 1956.90 | 0.012 |
| 25 | Fmoc-NapAla | X | X | 3269.8 | 2660.80 | 0.009 |
| 26 | Fmoc-napala | X | X | 2474.05 | 1865.05 | 0.012 |
| 27 | Fmoc-Phg | X | X | 2763.05 | 2154.05 | 0.011 |
| 28 | Fmoc-ChAla | X | X | 2722.1 | 2113.10 | 0.011 |
| 29 | Fmoc-chala | X | X | 2309.85 | 1700.85 | 0.013 |
| 30 | X | Fmoc-Ala | X | 1493.25 | 884.25 | 0.026 |
| 31 | X | Fmoc-Phe | X | 2522.15 | 1913.15 | 0.012 |
| 32 | X | Fmoc-Gly | X | 2556.75 | 1947.75 | 0.012 |
| 33 | X | Fmoc-Ile | X | 1806.1 | 1197.10 | 0.019 |
| 34 | X | Fmoc-Leu | X | 2223.3 | 1614.30 | 0.014 |
| 35 | X | Fmoc-Met(O) | X | 2216.8 | 1607.80 | 0.014 |
| 36 | X | Fmoc-Ser(tBut) | X | 1869.75 | 1260.75 | 0.018 |
| 37 | X | Fmoc-Thr(tBut) | X | 2391.1 | 1782.10 | 0.013 |
| 38 | X | Fmoc-Val | X | 1412.55 | 803.55 | 0.028 |
| 39 | X | Fmoc-Tyr(tBut) | X | 2255.4 | 1646.40 | 0.014 |
| 40 | X | Fmoc-ala | X | 2289 | 1680.00 | 0.013 |
| 41 | X | Fmoc-phe | X | 2743.5 | 2134.50 | 0.011 |
| 42 | X | Fmoc-ile | X | 2235.5 | 1626.50 | 0.014 |

TABLE 10-continued

N-Benzyl-1,4,5-trisubstituted-
2,3-diketopiperazine Library
Orphanin Binding Inhibition Assay

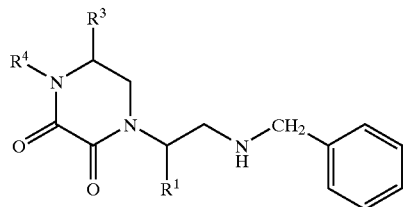

| Pool No. | R¹ | R³ | R⁴ | Mean | Minus NSB | 1% Bound |
|---|---|---|---|---|---|---|
| 43 | X | Fmoc-leu | X | 2652.75 | 2043.75 | 0.011 |
| 44 | X | Fmoc-ser(tBut) | X | 2738 | 2129.00 | 0.011 |
| 45 | X | Fmoc-thr(tBut) | X | 2866.4 | 2257.40 | 0.010 |
| 46 | X | Fmoc-val | X | 2646.55 | 2037.55 | 0.011 |
| 47 | X | Fmoc-tyr(tBut) | X | 2883.2 | 2274.20 | 0.010 |
| 48 | X | Fmoc-Nle | X | 2280.45 | 1671.45 | 0.014 |
| 49 | X | Fmoc-nle | X | 2402.65 | 1793.65 | 0.013 |
| 50 | X | Fmoc-Nva | X | 2142.8 | 1533.80 | 0.015 |
| 51 | X | Fmoc-nva | X | 2595.6 | 1986.60 | 0.011 |
| 52 | X | Fmoc-NapAla | X | 2770.2 | 2161.20 | 0.010 |
| 53 | X | Fmoc-napala | X | 2669.55 | 2060.55 | 0.011 |
| 54 | X | Fmoc-Phg | X | 2508.75 | 1899.75 | 0.012 |
| 55 | X | Fmoc-ChAla | X | 2448.75 | 1839.75 | 0.012 |
| 56 | X | Fmoc-chala | X | 2500.3 | 1891.30 | 0.012 |
| 57 | X | X | 1-Phenyl-1-cyclopropane carboxylic Acid | 2705.3 | 2096.30 | 0.011 |
| 58 | X | X | m-Tolylacetic Acid | 2473.85 | 1864.85 | 0.012 |
| 59 | X | X | 3-Fluorophenyl-acetic Acid | 2380.2 | 1771.20 | 0.013 |
| 60 | X | X | (α,α,α-Trifluoro-m-tolyl)acetic Acid | 2410.85 | 1801.85 | 0.013 |
| 61 | X | X | p-Tolylacetic Acid | 3147 | 2538.00 | 0.009 |
| 62 | X | X | 3-Methoxy-phenylacetic Acid | 1550.15 | 941.15 | 0.024 |
| 63 | X | X | 4-Methoxy-phenylacetic Acid | 1899.05 | 1290.05 | 0.018 |
| 64 | X | X | 4-Ethoxyphenyl-acetic Acid | 1908.75 | 1299.75 | 0.017 |
| 65 | X | X | 4-Isobutyl-α-methylphenylacetic Acid | 2712.35 | 2103.35 | 0.011 |
| 66 | X | X | 3,4-Dichloro-phenylacetic Acid | 2205.25 | 1596.25 | 0.014 |
| 67 | X | X | 3,5-Bis(Trifluoro-methyl)phenyl acetic Acid | 2814.9 | 2205.90 | 0.010 |
| 68 | X | X | Phenylacetic Acid | 2289.7 | 1680.70 | 0.013 |
| 69 | X | X | Hydrocinnamic Acid | 2539.3 | 1930.30 | 0.012 |
| 70 | X | X | 4-Phenylbutyric Acid | 2653.25 | 2044.25 | 0.011 |
| 71 | X | X | Butyric Acid | 2479.05 | 1870.05 | 0.012 |
| 72 | X | X | Heptanoic Acid | 2214.45 | 1605.45 | 0.014 |
| 73 | X | X | Isobutyric Acid | 2232.9 | 1623.90 | 0.014 |
| 74 | X | X | Isovaleric Acid | 2526.6 | 1917.60 | 0.012 |
| 75 | X | X | 4-Methylvaleric Acid | 2434.75 | 1825.75 | 0.012 |
| 76 | X | X | Trimethylacetic Acid | 2445.7 | 1836.70 | 0.012 |
| 77 | X | X | tert-Butylacetic Acid | 2671.55 | 2062.55 | 0.011 |
| 78 | X | X | Cyclohexane-carboxylic Acid | 2467.35 | 1858.35 | 0.012 |

TABLE 10-continued

N-Benzyl-1,4,5-trisubstituted-
2,3-diketopiperazine Library
Orphanin Binding Inhibition Assay

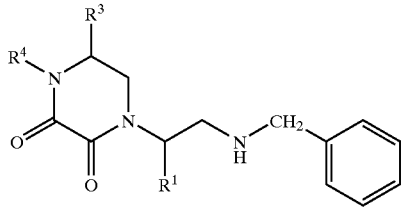

| Pool No. | R¹ | R³ | R⁴ | Mean | Minus NSB | 1% Bound |
|---|---|---|---|---|---|---|
| 79 | X | X | Cyclohexyl-acetic Acid | 2580.25 | 1971.25 | 0.011 |
| 80 | X | X | Cyclohexane-butyric Acid | 2583.55 | 1974.55 | 0.011 |
| 81 | X | X | Cycloheptane-carboxylic Acid | 2644.3 | 2035.30 | 0.011 |
| 82 | X | X | Acetic Acid | 2830.85 | 2221.85 | 0.010 |
| 83 | X | X | Cyclobutane-carboxylic Acid | 2625.5 | 2016.50 | 0.011 |
| 84 | X | X | Cyclopentane-carboxylic Acid | 2784.4 | 2175.40 | 0.010 |
| 85 | X | X | Cyclohexane-propionic Acid | 2836.75 | 2227.75 | 0.010 |
| 86 | X | X | 4-Methyl-1-cyclohexane-carboxylic Acid | 2735.2 | 2126.20 | 0.011 |
| 87 | X | X | 4-tert-Butyl-cyclohexane-carboxylic Acid | 3084.25 | 2475.25 | 0.009 |
| 88 | X | X | 1-Adamantane-acetic Acid | 2539.75 | 1930.75 | 0.012 |
| 89 | X | X | 3,3-Diphenyl-propionic Acid | 2445.7 | 1836.70 | 0.012 |
| 90 | X | X | Dicyclohexyl-acetic Acid | 2537.6 | 1928.60 | 0.012 |
| 91 | X | X | Indole-3-acetic Acid | 2796.4 | 2187.40 | 0.010 |
| 92 | X | X | 1-Naphthyl-acetic Acid | 2269.9 | 1660.90 | 0.014 |
| 93 | X | X | 3-(3,4,5)-Tri-methoxyphenyl-propionic Acid | 2390.7 | 1781.70 | 0.013 |
| 94 | X | X | 2-Norbomane-acetic Acid | 2083.8 | 1474.80 | 0.015 |
| 95 | X | X | Cyclopentyl-acetic Acid | 2666 | 2057.00 | 0.011 |
| 96 | X | X | 2-Ethylbutyric Acid | 2495.65 | 1886.65 | 0.012 |

The results of a binding study such as that above are often graphed using the 1/(percent bound) data provided above. However, merely scanning the data indicates that pools 13 and 15 provided the best binding for R¹, pools 30 and 38 provided best binding for R³ and pool 62 provided best binding for R⁴.

EXAMPLE 7

Binding Inhibition of the Rat Brain Mu Receptor by Members of a N-Benzyl-1,4,5-trisubstituted-2,3-diketopiperazine Library The previously prepared N-benzyl-1,4,5-trisubstituted-2,3-diketopiperazine library was screened for its ability to inhibit the binding of [$^3$H] [D-Ala$^2$,MePhe$^4$,Gly$^5$-ol] enkephalin (DAMGO) that is known to bind specifically to the mu opiate receptor present in rat brain homogenates following literature procedures. [Dooley et al., *Science*, 266:2019(1994); U.S. Pat. No. 5,763,193.]

Preparation of rat brain membranes and the receptor binding assay were carried out as described in Dooley et al., *Life Sci.*, 5:1509(1993). Each tube in the screening assay contained 0.08 mg of compound mixture per milliliter, 0.5 mL of membrane suspension (0.1 mg of protein), 7 nM $^3$H-labeled DAMGO [specific activity 36 Ci/mmol, obtained from the National Institute on Drug Abuse (NIDA) repository through Chiron Mimotopes PeptideSystems (San Diego, Calif.) and 50 mL of peptide mixture in 50 mM Tris-HCl buffer (pH 7.4). The final volume was 0.65 mL. The results of these screenings are shown below in Table 11, below. The results are reported in a manner similar to that discussed above, with the final results being reported as percent inhibition of DAMGO binding.

TABLE 11

N-Benzyl-1,4,5-trisubstituted-
2,3-diketopiperazine Library
Binding Inhibition of [³H] DAMGO

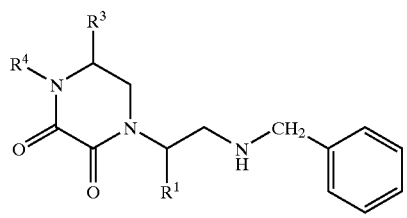

| Pool No. | R¹ | R³ | R⁴ | Mean | Minus NSB | % Inhibition |
|---|---|---|---|---|---|---|
| 1 | Fmoc-Ala | X | X | 795 | 568.0 | 26.1 |
| 2 | Fmoc-Phe | X | X | 305.6 | 78.6 | 89.8 |
| 3 | Fmoc-Gly | X | X | 701.0 | 474.0 | 38.4 |
| 4 | Fmoc-Ile | X | X | 693.4 | 466.4 | 39.4 |
| 5 | Fmoc-Lys(Boc) | X | X | 660.1 | 433.1 | 43.7 |
| 6 | Fmoc-Leu | X | X | 713.9 | 486.9 | 36.7 |
| 7 | Fmoc-Met(O) | X | X | 751.1 | 524.1 | 31.9 |
| 8 | Fmoc-Ser(tBut) | X | X | 953.0 | 726.0 | 5.6 |
| 9 | Fmoc-Thr(tBut) | X | X | 498.6 | 271.6 | 64.7 |
| 10 | Fmoc-Val | X | X | 753.9 | 526.9 | 31.5 |
| 11 | Fmoc-Tyr(tBut) | X | X | 681.8 | 454.8 | 40.9 |
| 12 | Fmoc-ala | X | X | 803.2 | 576.2 | 25.1 |
| 13 | Fmoc-phe | X | X | 469.9 | 242.9 | 68.4 |
| 14 | Fmoc-ile | X | X | 594.0 | 367.0 | 52.3 |
| 15 | Fmoc-lys(Boc) | X | X | 393.4 | 166.4 | 78.4 |
| 16 | Fmoc-leu | X | X | 585.3 | 358.3 | 53.4 |
| 17 | Fmoc-ser(tBut) | X | X | 964.4 | 737.4 | 4.1 |
| 18 | Fmoc-thr(tBut) | X | X | 859.7 | 632.7 | 17.7 |
| 19 | Fmoc-val | X | X | 375.3 | 148.3 | 80.7 |
| 20 | Fmoc-tyr(tBut) | X | X | 313.6 | 86.6 | 88.8 |
| 21 | Fmoc-Nle | X | X | 707 | 480.0 | 37.5 |
| 22 | Fmoc-nle | X | X | 601.4 | 374.4 | 51.3 |
| 23 | Fmoc-Nva | X | X | 733.1 | 506.1 | 34.2 |
| 24 | Fmoc-nva | X | X | 419.1 | 192.1 | 75.0 |
| 25 | Fmoc-NapAla | X | X | 459.8 | 232.8 | 69.7 |
| 26 | Fmoc-napala | X | X | 324.7 | 97.7 | 87.3 |
| 27 | Fmoc-Phg | X | X | 725.5 | 498.5 | 35.2 |
| 28 | Fmoc-ChAla | X | X | 445.3 | 218.3 | 71.6 |
| 29 | Fmoc-chala | X | X | 761.5 | 534.5 | 30.5 |
| 30 | X | Fmoc-Ala | X | 572.8 | 345.8 | 55.0 |
| 31 | X | Fmoc-Phe | X | 328.5 | 101.5 | 86.8 |
| 32 | X | Fmoc-Gly | X | 466.7 | 239.7 | 68.8 |
| 33 | X | Emoc-Ile | X | 611.9 | 384.9 | 50.0 |
| 34 | X | Fmoc-Leu | X | 637.9 | 410.9 | 46.6 |
| 35 | X | Fmoc-Met(O) | X | 490 | 263.0 | 65.8 |
| 36 | X | Fmoc-Ser(tBut) | X | 847.9 | 620.9 | 19.3 |
| 37 | X | Fmoc-Thr(tBut) | X | 934.4 | 707.4 | 8.0 |
| 38 | X | Fmoc-Val | X | 751.1 | 524.1 | 31.9 |
| 39 | X | Fmoc-Tyr(tBut) | X | 541.9 | 314.9 | 59.1 |
| 40 | X | Fmoc-ala | X | 581.4 | 354.4 | 53.9 |
| 41 | X | Fmoc-phe | X | 522.6 | 295.6 | 61.6 |
| 42 | X | Fmoc-ile | X | 238.1 | 11.1 | 98.6 |
| 43 | X | Fmoc-leu | X | 512.5 | 285.5 | 62.9 |
| 44 | X | Fmoc-ser(tBut) | X | 611.2 | 384.2 | 50.1 |
| 45 | X | Fmoc-thr(tBut) | X | 697.8 | 470.8 | 38.8 |
| 46 | X | Fmoc-val | X | 251.2 | 24.2 | 96.9 |
| 47 | X | Fmoc-tyr(tBut) | X | 565.35 | 338.4 | 56.0 |
| 48 | X | Fmoc-Nle | X | 414.8 | 187.8 | 75.6 |
| 49 | X | Fmoc-nle | X | 506.4 | 279.4 | 63.7 |
| 50 | X | Fmoc-Nva | X | 506.4 | 279.4 | 63.7 |
| 51 | X | Fmoc-nva | X | 467.6 | 240.6 | 68.7 |
| 52 | X | Fmoc-NapAla | X | 853.7 | 626.7 | 18.5 |
| 53 | X | Fmoc-napala | X | 883.1 | 656.1 | 14.7 |
| 54 | X | Fmoc-Phg | X | 342.2 | 115.2 | 85.0 |
| 55 | X | Fmoc-ChAla | X | 878.6 | 651.6 | 15.3 |
| 56 | X | Fmoc-chala | X | 612.9 | 385.9 | 49.8 |
| 57 | X | X | 1-Phenyl-1-cyclo-propanecarboxylic Acid | 351.7 | 124.7 | 83.8 |

TABLE 11-continued

N-Benzyl-1,4,5-trisubstituted-
2,3-diketopiperazine Library
Binding Inhibition of [$^3$H] DAMGO

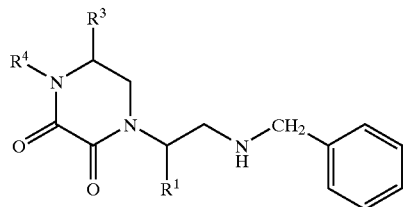

| Pool No. | R$^1$ | R$^3$ | R$^4$ | Mean | Minus NSB | % Inhibition |
|---|---|---|---|---|---|---|
| 58 | X | X | m-Tolylacetic Acid | 537.2 | 310.2 | 59.7 |
| 59 | X | X | 3-Fluorophenyl acetic Acid | 506.4 | 279.4 | 63.7 |
| 60 | X | X | (α,α,α-Trifluoro-m-tolyl)acetic Acid | 545.3 | 318.3 | 58.6 |
| 61 | X | X | p-Tolylacetic Acid | 502.4 | 275.4 | 64.2 |
| 62 | X | X | 3-Methoxyphenyl-acetic Acid | 447.4 | 220.4 | 71.4 |
| 63 | X | X | 4-Methoxyphenyl-acetic Acid | 410.9 | 183.9 | 76.1 |
| 64 | X | X | 4-Ethoxyphenyl-acetic Acid | 735.3 | 508.3 | 33.9 |
| 65 | X | X | 4-Isobutyl-α-methyl-phenylacetic Acid | 850.6 | 623.6 | 18.9 |
| 66 | X | X | 3,4-Dichloro-phenylacetic Acid | 536.6 | 309.6 | 59.7 |
| 67 | X | X | 3,5-Bis-(trifluoromethyl)-phenylacetic Acid | 868.3 | 641.3 | 16.6 |
| 68 | X | X | Phenylacetic Acid | 557.1 | 330.1 | 57.1 |
| 69 | X | X | Hydrocinnamic Acid | 615.6 | 388.6 | 49.5 |
| 70 | X | X | 4-Phenylbutyric Acid | 750.7 | 523.7 | 31.9 |
| 71 | X | X | Butyric Acid | 509.4 | 282.4 | 63.3 |
| 72 | X | X | Heptanoic Acid | 731.4 | 504.4 | 34.4 |
| 73 | X | X | Isobutyric Acid | 314.9 | 87.9 | 88.6 |
| 74 | X | X | Isovaleric Acid | 468.1 | 241.1 | 68.7 |
| 75 | X | X | 4-Methylvaleric Acid | 579.3 | 352.3 | 54.2 |
| 76 | X | X | Trimethylacetic Acid | 335.4 | 108.4 | 85.9 |
| 77 | X | X | tert-Butylacetic Acid | 607.8 | 380.8 | 50.5 |
| 78 | X | X | Cyclohexane-carboxylic Acid | 468.2 | 241.2 | 68.6 |
| 79 | X | X | Cyclohexyl-acetic Acid | 712.5 | 485.5 | 36.9 |
| 80 | X | X | Cyclohexane-butyric Acid | 817.7 | 590.7 | 23.2 |
| 81 | X | X | Cycloheptane-carboxylic Acid | 606.1 | 379.1 | 50.7 |
| 82 | X | X | Acetic Acid | 667 | 440.0 | 42.8 |
| 83 | X | X | Cyclobutane-carboxylic Acid | 405.8 | 178.8 | 76.8 |
| 84 | X | X | Cyclopentane-carboxylic Acid | 421.9 | 194.9 | 74.7 |
| 85 | X | X | Cyclohexane-propionic Acid | 798.6 | 571.6 | 25.7 |
| 86 | X | X | 4-Methyl-1-cyclohexane-carboxylic Acid | 770.2 | 543.2 | 29.4 |
| 87 | X | X | 4-tert-Butyl-cyclohexane-carboxylic Acid | 809.7 | 582.7 | 24.2 |
| 88 | X | X | 1-Adamantane-acetic Acid | 996.8 | 769.8 | −0.10 |
| 89 | X | X | 3-3-Diphenyl-propionic Acid | 745.3 | 518.3 | 32.6 |

TABLE 11-continued

N-Benzyl-1,4,5-trisubstituted-
2,3-diketopiperazine Library
Binding Inhibition of [$^3$H] DAMGO

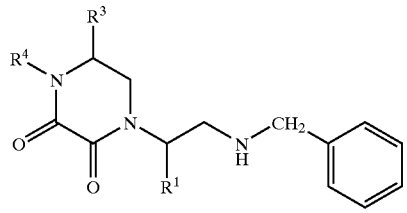

| Pool No. | R$^1$ | R$^3$ | R$^4$ | Mean | Minus NSB | % Inhibition |
|---|---|---|---|---|---|---|
| 90 | X | X | Dicyclohexyl-acetic Acid | 489.4 | 262.4 | 65.9 |
| 91 | X | X | Indole-3-acetic Acid | 730.0 | 503.0 | 34.6 |
| 92 | X | X | 1-Naphthylacetic Acid | 472.2 | 245.2 | 68.1 |
| 93 | X | X | 3-(3,4,5)-Tri-methoxyphenyl propionic Acid | 356 | 129.0 | 83.2 |
| 94 | X | X | 2-Norbomane-acetic Acid | 673.2 | 446.2 | 42.0 |
| 95 | X | X | Cyclopentyl acetic Acid | 682.6 | 455.6 | 40.8 |
| 96 | X | X | 2-Ethylbutyric Acid | 400.2 | 173.2 | 77.5 |

The results of a binding study such as that above are often graphed using the percent inhibition data provided above. However, merely scanning the data indicates that pools 2, 20 and 26 provided the best binding inhibition for R$^1$, pools 31, 42 and 46 provided best binding inhibition for R$^3$, and pools 57, 73, 76 and 93 provided best binding inhibition for R$^4$.

EXAMPLE 8

Screening of a N-Benzyl-1,4,5-trisubstituted-2,3-diketopiperazine Library Binding in hORL-CHO Cells The human ORL$_1$ receptor is the human equivalent of the murine Orphanin receptor that naturally binds to a pituitary peptide dynorphin A, as discussed in Example 6. Mollereau and co-workers cloned the gene for the human receptor [FEBS Letters, 341:33(1994)] and stably expressed that gene in CHO cells (Nature, 377:532(1995)]. One of the authors of the latter paper graciously provided a sample of those transgenic cells [referred to as recombinant CHO (hORL$_1$) cells] for use by the present inventors.

Binding inhibition studies similar to those of Example 6 were carried out using 500,00 cells/mL in place of the membrane preparation using the N-benzyl-1,4,5-trisubstituted-2,3-diketopiperazine library. The results of those studies are shown in Table 12, below, for each library pool.

TABLE 12

N-Benzyl-1,4,5-trisubstituted-
2,3-diketopiperazine Library
Binding in hORL-CHO Cells

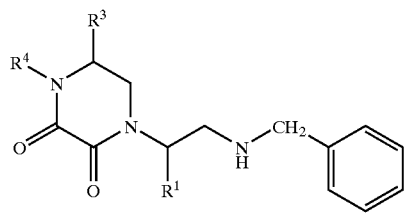

| Pool No. | R$^1$ | R$^3$ | R$^4$ | Mean | Minus NSB | 1% Bound |
|---|---|---|---|---|---|---|
| 1 | Fmoc-Ala | X | X | 384 | 251.00 | 0.020 |
| 2 | Fmoc-Phe | X | X | 346 | 213.00 | 0.024 |
| 3 | Fmoc-Gly | X | X | 338.5 | 205.50 | 0.025 |

TABLE 12-continued

N-Benzyl-1,4,5-trisubstituted-
2,3-diketopiperazine Library
Binding in hORL-CHO Cells

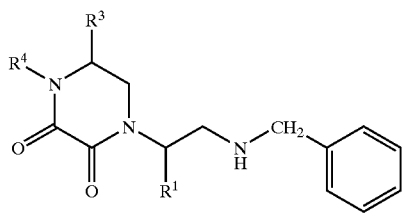

| Pool No. | R¹ | R³ | R⁴ | Mean | Minus NSB | 1% Bound |
|---|---|---|---|---|---|---|
| 4 | Fmoc-Ile | X | X | 382.5 | 249.50 | 0.020 |
| 5 | Fmoc-Lys(Boc) | X | X | 233.35 | 100.35 | 0.050 |
| 6 | Fmoc-Leu | X | X | 391.55 | 258.55 | 0.019 |
| 7 | Fmoc-Met(O) | X | X | 351.05 | 218.05 | 0.023 |
| 8 | Fmoc-Ser(tBut) | X | X | 431.2 | 298.20 | 0.017 |
| 9 | Fmoc-Thr(tBut) | X | X | 491.7 | 358.70 | 0.014 |
| 10 | Fmoc-Val | X | X | 448.55 | 315.55 | 0.016 |
| 11 | Fmoc-Tyr(tBut) | X | X | 438.45 | 305.45 | 0.017 |
| 12 | Fmoc-ala | X | X | 366.1 | 233.10 | 0.022 |
| 13 | Fmoc-phe | X | X | 324.6 | 191.60 | 0.026 |
| 14 | Fmoc-ile | X | X | 399.75 | 266.75 | 0.019 |
| 15 | Fmoc-lys(Boc) | X | X | 188.35 | 55.35 | 0.091 |
| 16 | Fmoc-leu | X | X | 357.2 | 224.20 | 0.022 |
| 17 | Fmoc-ser(tBut) | X | X | 413.55 | 280.55 | 0.018 |
| 18 | Fmoc-thr(tBut) | X | X | 518.55 | 385.55 | 0.013 |
| 19 | Fmoc-val | X | X | 388.9 | 255.90 | 0.020 |
| 20 | Fmoc-tyr(tBut) | X | X | 424.25 | 291.25 | 0.017 |
| 21 | Fmoc-Nle | X | X | 341.2 | 208.20 | 0.024 |
| 22 | Fmoc-nle | X | X | 379.25 | 246.25 | 0.020 |
| 23 | Fmoc-Nva | X | X | 432.85 | 299.85 | 0.017 |
| 24 | Fmoc-nva | X | X | 380.9 | 247.90 | 0.020 |
| 25 | Fmoc-NapAla | X | X | 385.35 | 252.35 | 0.020 |
| 26 | Fmoc-napala | X | X | 355.3 | 222.30 | 0.023 |
| 27 | Fmoc-Phg | X | X | 476.05 | 343.05 | 0.015 |
| 28 | Fmoc-ChAla | X | X | 459.6 | 326.60 | 0.015 |
| 29 | Fmoc-chala | X | X | 426.65 | 293.65 | 0.017 |
| 30 | X | Fmoc-Ala | X | 245.7 | 112.70 | 0.045 |
| 31 | X | Fmoc-Phe | X | 402.85 | 269.85 | 0.019 |
| 32 | X | Fmoc-Gly | X | 308.65 | 175.65 | 0.029 |
| 33 | X | Fmoc-Ile | X | 316.5 | 183.50 | 0.027 |
| 34 | X | Fmoc-Leu | X | 373.2 | 240.20 | 0.021 |
| 35 | X | Fmoc-Met(O) | X | 372 | 239.00 | 0.021 |
| 36 | X | Fmoc-Ser(tBut) | X | 357.5 | 224.50 | 0.022 |
| 37 | X | Fmoc-Thr(tBut) | X | 340.05 | 207.05 | 0.024 |
| 38 | X | Fmoc-Val | X | 267.65 | 134.65 | 0.037 |
| 39 | X | Fmoc-Tyr(tBut) | X | 402.15 | 269.15 | 0.019 |
| 40 | X | Fmoc-ala | X | 299.1 | 166.10 | 0.030 |
| 41 | X | Fmoc-phe | X | 407.75 | 274.75 | 0.018 |
| 42 | X | Fmoc-ile | X | 328.85 | 195.85 | 0.026 |
| 43 | X | Fmoc-leu | X | 419.65 | 286.65 | 0.018 |
| 44 | X | Fmoc-ser(tBut) | X | 314.85 | 181.85 | 0.028 |
| 45 | X | Fmoc-thr(tBut) | X | 401.25 | 268.25 | 0.019 |
| 46 | X | Fmoc-val | X | 359.15 | 226.15 | 0.022 |
| 47 | X | Fmoc-tyr(tBut) | X | 522.25 | 389.25 | 0.013 |
| 48 | X | Fmoc-Nle | X | 300.3 | 167.30 | 0.030 |
| 49 | X | Fmoc-nle | X | 282.9 | 149.90 | 0.034 |
| 50 | X | Fmoc-Nva | X | 300.95 | 167.95 | 0.030 |

TABLE 12-continued

N-Benzyl-1,4,5-trisubstituted-
2,3-diketopiperazine Library
Binding in hORL-CHO Cells

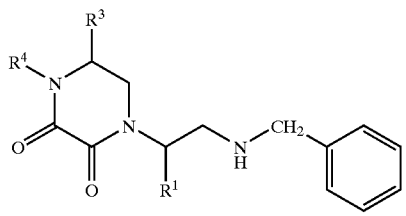

| Pool No. | $R^1$ | $R^3$ | $R^4$ | Mean | Minus NSB | 1% Bound |
|---|---|---|---|---|---|---|
| 51 | X | Fmoc-nva | X | 438.65 | 305.65 | 0.016 |
| 52 | X | Fmoc-NapAla | X | 331.05 | 198.05 | 0.025 |
| 53 | X | Fmoc-napala | X | 340.05 | 207.05 | 0.024 |
| 54 | X | Fmoc-Phg | X | 256.9 | 123.90 | 0.041 |
| 55 | X | Fmoc-ChAla | X | 417.65 | 284.65 | 0.018 |
| 56 | X | Fmoc-chala | X | 341.55 | 208.55 | 0.024 |
| 57 | X | X | 1-Phenyl-1-cyclopropane-carboxylic Acid | 299.95 | 166.95 | 0.030 |
| 58 | X | X | m-Tolylacetic Acid | 343.7 | 210.70 | 0.024 |
| 59 | X | X | 3-Fluorophenylacetic Acid | 346.5 | 213.50 | 0.024 |
| 60 | X | X | (α,α,α-Trifluoro-m-tolyl)acetic acid | 290.45 | 157.45 | 0.032 |
| 61 | X | X | p-Tolylacetic Acid | 266.35 | 133.35 | 0.038 |
| 62 | X | X | 3-Methoxyphenylacetic Acid | 385.3 | 252.30 | 0.020 |
| 63 | X | X | 4-Methoxyphenylacetic Acid | 266.9 | 133.90 | 0.038 |
| 64 | X | X | 4-Ethoxyphenylacetic Acid | 289.35 | 156.35 | 0.032 |
| 65 | X | X | 4-Isobutyl-α-methylphenyl-acetic Acid | 351.45 | 218.45 | 0.023 |
| 66 | X | X | 3,4-Dichloro-phenylacetic Acid | 238.4 | 105.40 | 0.048 |
| 67 | X | X | 3,5-Bis-(Trifluoro-methyl)phenyl-acetic Acid | 306.4 | 173.40 | 0.029 |
| 68 | X | X | Phenylacetic Acid | 385.15 | 252.15 | 0.020 |
| 69 | X | X | Hydrocinnamic Acid | 367.45 | 234.45 | 0.021 |
| 70 | X | X | 4-Phenylbutyric Acid | 366.4 | 233.40 | 0.022 |
| 71 | X | X | Butyric Acid | 369.1 | 236.10 | 0.021 |
| 72 | X | X | Heptanoic Acid | 293.6 | 160.60 | 0.031 |
| 73 | X | X | Isobutyric Acid | 284.25 | 151.25 | 0.033 |
| 74 | X | X | Isovaleric Acid | 369.95 | 236.95 | 0.021 |
| 75 | X | X | 4-Methylvaleric Acid | 341.05 | 208.05 | 0.024 |
| 76 | X | X | Trimethylacetic Acid | 395.45 | 262.45 | 0.019 |
| 77 | X | X | tert-Butylacetic Acid | 394.35 | 261.35 | 0.019 |
| 78 | X | X | Cyclohexanecarboxylic Acid | 352.35 | 219.35 | 0.023 |
| 79 | X | X | Cyclohexyl-acetic Acid | 337.05 | 204.05 | 0.025 |

TABLE 12-continued

N-Benzyl-1,4,5-trisubstituted-
2,3-diketopiperazine Library
Binding in hORL-CHO Cells

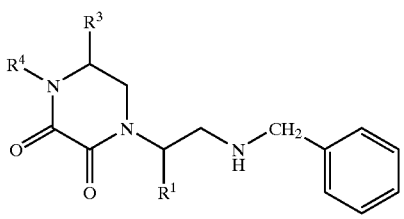

| Pool No. | $R^1$ | $R^3$ | $R^4$ | Mean | Minus NSB | 1% Bound |
|---|---|---|---|---|---|---|
| 80 | X | X | Cyclohexane-butyric Acid | 325.15 | 192.15 | 0.026 |
| 81 | X | X | Cycloheptanecarboxylic Acid | 248.4 | 115.40 | 0.044 |
| 82 | X | X | Acetic Acid | 353.9 | 220.90 | 0.023 |
| 83 | X | X | Cyclobutanecarboxylic Acid | 399.7 | 266.70 | 0.019 |
| 84 | X | X | Cyclopentanecarboxylic Acid | 406.9 | 273.90 | 0.018 |
| 85 | X | X | Cyclohexanepropionic Acid | 412.35 | 279.35 | 0.018 |
| 86 | X | X | 4-Methyl-1-cyclo-hexanecarboxylic Acid | 391.3 | 258.30 | 0.020 |
| 87 | X | X | 4-tert-Butyl-cyclohexane-carboxylic Acid | 338.2 | 205.20 | 0.025 |
| 88 | X | X | 1-Adamantaneacetic Acid | 235.75 | 102.75 | 0.049 |
| 89 | X | X | 3-3-Diphenylpropionic Acid | 291.45 | 158.45 | 0.032 |
| 90 | X | X | Dicyclohexyl-acetic Acid | 271.9 | 138.90 | 0.036 |
| 91 | X | X | Indole-3-acetic Acid | 431.6 | 298.60 | 0.017 |
| 92 | X | X | 1-Naphthylacetic Acid | 325.55 | 192.55 | 0.026 |
| 93 | X | X | 3-(3,4,5)-tri-methoxy-phenylpropionic Acid | 410.1 | 277.10 | 0.018 |
| 94 | X | X | 2-Norbornane-acetic Acid | 322.95 | 189.95 | 0.027 |
| 95 | X | X | Cyclopentyl-acetic Acid | 314.45 | 181.45 | 0.028 |
| 96 | X | X | 2-Ethyl butyric Acid | 310.5 | 177.50 | 0.028 |

The results of a binding study such as that above are often graphed using the 1/(percent bound) data provided above. Again, scanning the data indicates that pools 5 and 15 provided the best binding for $R^1$, pools 30 and 54 provided best binding for $R^3$ and pools 66 and 88 provided best binding for $R^4$. Interestingly, pools 15 and 30 also provided the greatest inhibition in the orphanin binding assay of Example 6.

EXAMPLE 9

Preparation of Bis-diketodiazabicyclic Compounds and Bis-diazacyclic Compounds

Bis-diketodiazabicyclic and bis-diazacyclic compounds and libraries are also contemplated here. Exemplary compounds have two carbonyl-containing rings or two ring nitrogen-containing rings linked to each other via a side chain of one of the R grooups of one of the rings such as a lysine or ornithine side chain. Scheme 8, below, illustrates an exemplary synthetic scheme that utilizes a lysine side chain.

An exemplary compound that was synthesized follows the Scheme and detained synthetic procedure.

Scheme 8

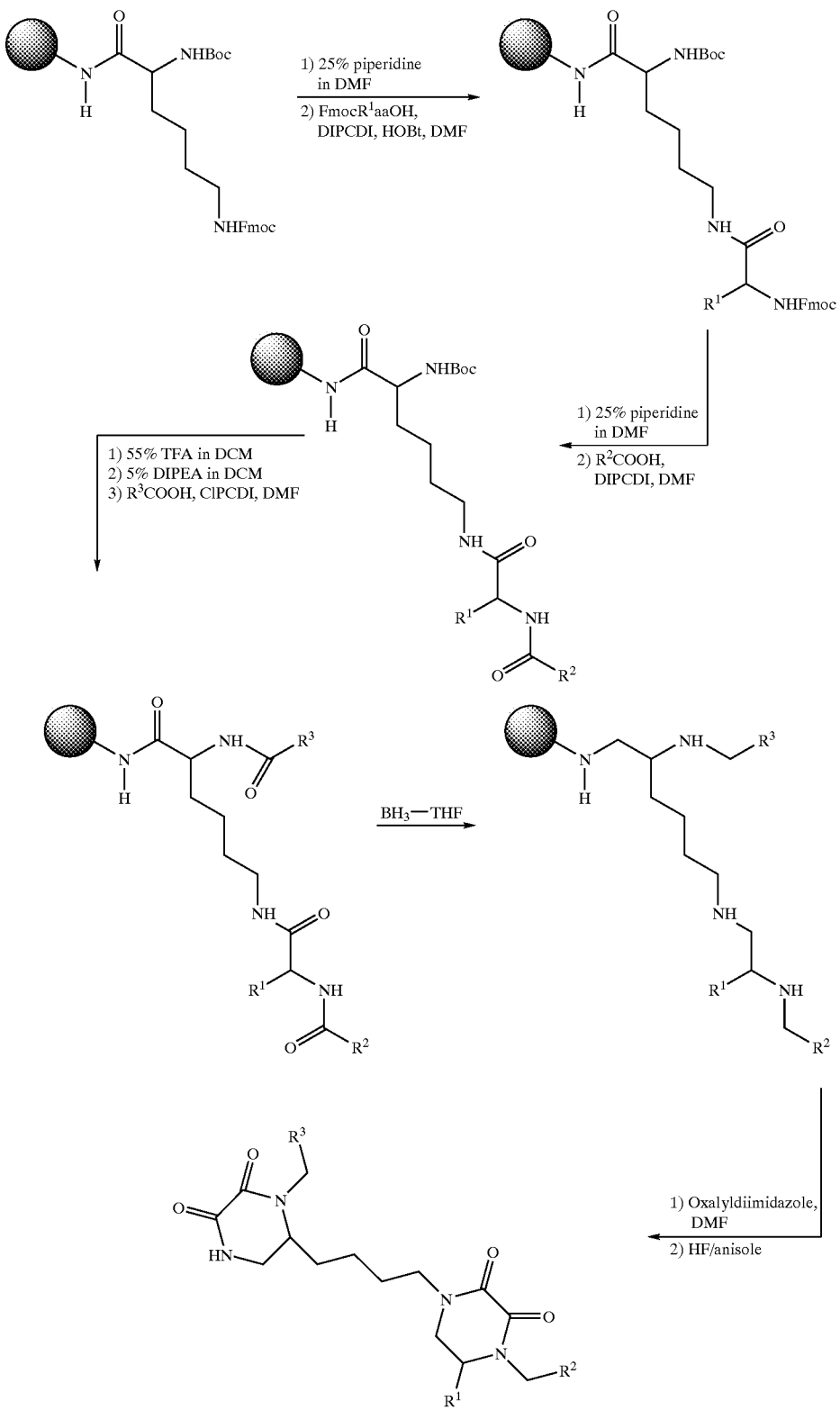

Typical procedure for the Boc-Lys(Fmoc) coupling.

p-Methylbenzydrylamine (MBHA; 100 mg) resin (0.1 meq/g, 100–200 mesh) was contained within a sealed polypropylene mesh resin packet. Following neutralization with 5% diisopropylethylamine (DIEA) in dichloromethane (DCM)(3×5 ml), the resin was washed with DCM (3×5 ml). A 0.5M solution of Boc-Lys(Fmoc) in DMF (6×, 0.6 meq total; 1.2 ml), 1.2 ml 0.5M 1-hydroxybenzotriazole (HOBt, 6×, 0.6 meq) in DMF, and 1.2 ml 0.5M diisopropylcarbodiimide (DIPCDI, 6×, 0.6 meq) in DMF was combined in a 10 ml polypropylene bottle. The resin packet was then added to the solution and permitted to react by shaking on a reciprocating shaker for 120 minutes. Following decanting of the reaction solution, the resin was washed with DMF (3×5 ml).

Typical Procedure for the Second Fmoc-amino Acid Coupling.

The Fmoc side chain protecting group was then removed by treatment with 5 ml of 25% piperidine in DMF, followed by washes with DMF (3×5 ml). A 0.5M solution of Fmoc-Phe in DMF (6×, 0.6 meq total; 1.2 ml), 1.2 ml 0.5M 1-hydroxybenzotriazole (HOBt, 6×, 0.6 meq) in DMF, and 1.2 ml 0.5M diisopropylcarbodiimide (DIPCDI, 6×, 0.6 meq) in DMF was combined in a 10 ml polypropylene bottle. The resin packet was then added to the solution and permitted to react by shaking on a reciprocating shaker for 120 minutes. Following the reaction, the solution was decanted and the resin washed with DMF (3×5 ml). Typical procedure for the first carboxylic acid coupling.

Following deprotection of the Fmoc protecting group with 5 ml 25% piperidine in DMF for 30 minutes, the resin was washed twice with 5 ml DMF. A 0.5M solution of phenyl acetic acid in DMF (10X, 1.0 meq total; 2.0 ml), 2.0 ml 0.5M 1-hydroxybenzotriazole (HOBt, 10×, 1.0 meq) in DMF, and 2.0 ml 0.5M diisopropylcarbodiimide (DIPCDI, 10×, 1.0 meq) in DMF was combined in a 10 ml polypropylene bottle. The resin packet was then added to the solution and permitted to react by shaking on reciprocation shaker for 120 minutes. Following the reaction, the solution was decanted and the resin washed with DMF (3×5 ml).

Typical Procedure for a Second Carboxylic Acid Coupling.

Following deprotection of the Boc protecting group with 5 ml 55% TFA/DCM for 30 minutes, the resin was washed twice with 5 ml DCM, 3 times with 5 ml isopropanol, and twice with 5 ml DCM. The resin packet was neutralized with 5% diisopropylethylamine (DIRA) in dichloromethane (DCM)(3×5 ml) and then washed with DCM (3×5 ml). A 0.5M solution of phenyl acetic acid in DMF (10×, 1.0 meq total; 2.0 ml), 2.0 ml 0.5M 1-hydroxybenzotriazole (HOBt, 10×, 1.0 meq) in DMF, and 2.0 ml 0.5M diisopropylcarbodiimide (DIPCDI, 10×, 1.0 meq) in DMF was combined in a 10 ml polypropylene bottle. The resin packet was then added to the solution and allowed to react by shaking on reciprocation shaker for 120 minutes. Following the reaction, the solution was decanted and the resin washed with DMF (3×5 ml).

The resins were reduced, the diketopiperizines were formed, and the resins were cleaved as described in Examples 1 and 2.

Using the above procedure and that of Scheme 8, a compound corresponding in structure to the formula below was prepared in which phenylacetic acid was used as $R^2COOH$ and $R^3COOH$ and FmocPhe was used as Fmoc-R1aa-OH

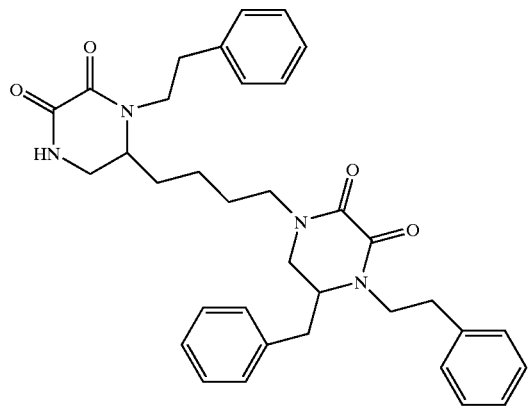

The foregoing description and the examples are intended as illustrative and are not to be taken as limiting. Still other variations within the spirit and scope of this invention are possible and will readily present themselves to those skilled in the art.

What is claimed is:

1. A compound having a structure corresponding to that shown in Formula II, below, or a pharmaceutically acceptable salt thereof:

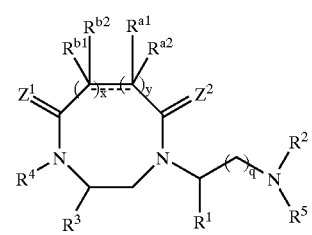

II wherein:

q is an integer that is one through seven;

each of $=Z^1$ and $=Z^2$ is $=O$;

x and y are one, and the sum of x+y is two;

the dotted line between the carbon atom of $R^{a1}$ and $R^{a2}$ and the carbon atom of $R^{b1}$ and $R^{b2}$ indicates the presence or absence of one additional bond between those depicted carbon atom, so that when present, the additional bond is shown as a solid line, following usual conventions of organic chemistry, and $R^{a2}$ and $R^{b2}$ are absent;

$R^{a2}$ and $R^{b2}$ are independently selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group, and each of $R^{a1}$ and $R^{b1}$ is independently a divalent carbon, nitrogen, oxygen or sulfur that together form a saturated or unsaturated mono- or bicyclic ring that contains 5- to 8-members in each ring and zero to three heteroatoms in each ring that are independently oxygen, nitrogen or sulfur, and wherein $R^{a2}$ and $R^{b2}$ are absent when a double bond is present between the depicted carbon atoms;

$R^1$ is selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^2$ is selected from the group consisting of a $C_1$–$C_{10}$ alkyl, $C_2$–$C_{10}$ alkenyl, benzyl, substituted benzyl, naphthyl, and a substituted naphthyl group;

$R^3$ is selected from the group consisting of a hydrido, $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^4$ is selected from the group consisting of a hydrido, $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenyl-alkenyl group; and $R^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

2. The compound according to claim 1 that corresponds in structure to a formula below

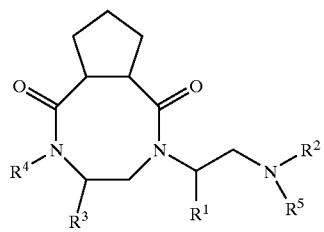
F1

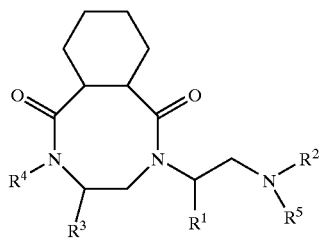
G1

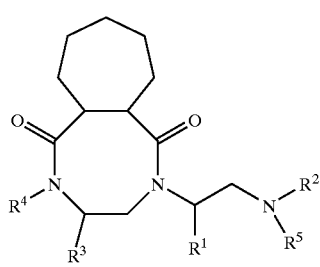
H1

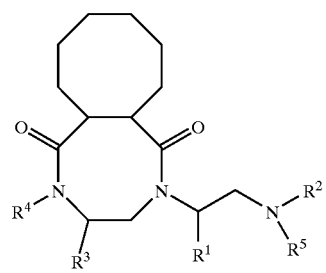
I1

-continued

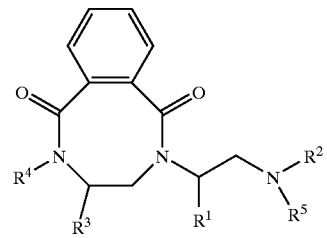
J1

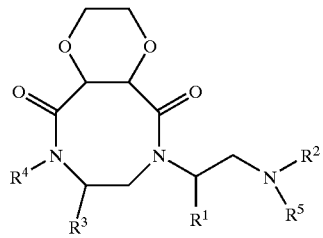
K1

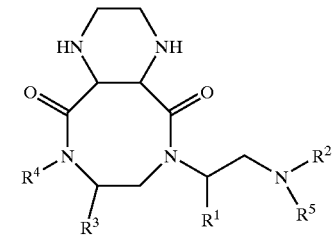
L1

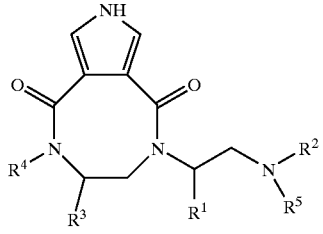
M1

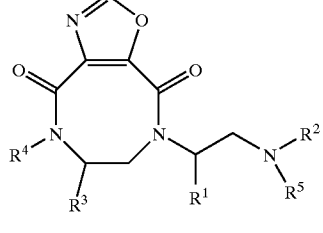
N1

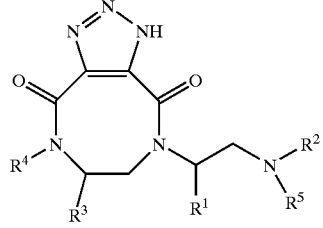
O1

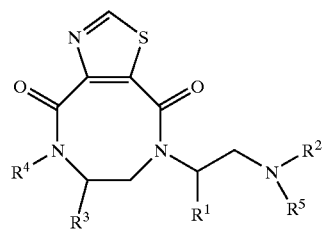
P1

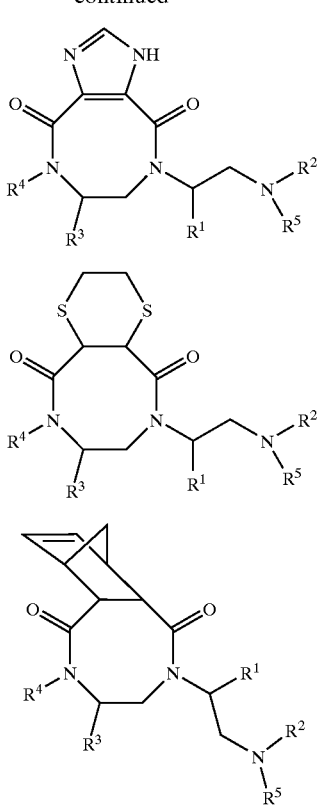

3. A compound having a structure corresponding to that shown in Formula III, below, or a pharmaceutically acceptable salt thereof:

III wherein:
=Z is =O;
$R^{a2}$ and $R^{b2}$ are hydrido or are absent;
q is an integer that is one through seven;
x and y are one, and the sum of x+y is two;
the dotted line between the carbon atom of $R^{a1}$ and $R^{a2}$ and the carbon atom of $R^{b1}$ and $R^{b2}$ indicates the presence or absence of one additional bond between those depicted carbon atoms, so that when present, the additional bond is shown as a solid line, following usual conventions of organic chemistry, and $R^{a2}$ and $R^{b2}$ are absent;
each of $R^{a1}$ and $R^{b1}$ is independently a divalent carbon, nitrogen, oxygen or sulfur that together form a saturated or unsaturated mono- or bicyclic ring that contains 5- to 8-members in each ring and zero to three heteroatoms in each ring that are independently oxygen, nitrogen or sulfur, and wherein $R^{a2}$ and $R^{b2}$ are absent when a double bond is present between the depicted carbon atoms;
$R^1$ is selected from the group consisting of a hydrido, $C_1$–$C_{10}$ alkyl, $C_1$–$C_{10}$ substituted alkyl, $C_1$–$C_{16}$ phenylalkyl, $C_7$–$C_{16}$ substituted phenyalkyl, phenyl, substituted phenyl, $C_3$–$C_7$ cycloalkyl, and a $C_3$–$C_7$ substituted cycloalkyl group;

$R^2$ is selected from the group consisting of a $C_1$–$C_{10}$ alkyl, $C_2$–$C_{10}$ alkenyl, benzyl, substituted benzyl, naphthyl, and a substituted naphthyl group;

$R^3$ is selected from the group consisting of a hydrido, $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^4$ is selected from the group consisting of a hydrido, $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenyl-alkenyl group; and $R^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

4. The compound according to claim 3 wherein $R^2$ is methyl, ethyl, allyl, benzyl or 2-naphthylmethyl.

5. The compound according to claim 3 wherein q is one.

6. The compound according to claim 1 wherein $R^2$ is methyl, ethyl, allyl, benzyl or 2-naphthylmethyl.

7. The compound according to claim 1 wherein a $C_1$–$C_{10}$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, of any of $R^1$, $R^2$, $R^3$, or $R^4$ is a $C_1$–$C_7$ alkyl, $C_2$–$C_7$ alkenyl, $C_2$–$C_7$ alkynyl, $C_1$–$C_7$ substituted alkyl, $C_2$–$C_7$ substituted alkenyl, or $C_2$–$C_7$ substituted alkynyl.

8. The compound according to claim 3 wherein q is one or two.

9. The compound according to claim 3 wherein a $C_1$–$C_{10}$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, of any of $R^1$, $R^2$, $R^3$, or $R^4$ is a $C_1$–$C_7$ alkyl, $C_2$–$C_7$ alkenyl, $C_2$–$C_7$ alkynyl, $C_1$–$C_7$ substituted alkyl, $C_2$–$C_7$ substituted alkenyl, or $C_2$–$C_7$ substituted alkynyl.

10. A compound having a structure corresponding to that shown below, or a pharmaceutically acceptable salt thereof:

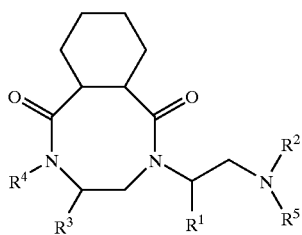

$R^1$ is selected from the group consisting of a hydrido, $C_1$–$C_{10}$ alkyl, $C_1$–$C_{10}$ substituted alkyl, $C_1$–$C_{10}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^2$ is selected from the group consisting of a $C_1$–$C_{10}$ alkyl, $C_2$–$C_{10}$ alkenyl, benzyl, substituted benzyl, naphthyl, and a substituted naphthyl group;

$R^3$ is selected from the group consisting of a hydrido, $C_1$–$C_{10}$ alkyl, $C_1$–$C_{10}$ substituted alkyl, $C_1$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^4$ is selected from the group consisting of a hydrido, $C_1$–$C_{10}$ alkyl, $C_2$–$C_{10}$ alkenyl, $C_1$–$C_{10}$ substituted alkyl, $C_3$–$C_7$ substituted cycloalkyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenyl-alkenyl group; and $R^5$ is selected from the group consisting of a hydrido, $C_1$–$C_{10}$ acyl, aroyl, $C_1$–$C_{10}$ alkylaminocarbonyl, $C_1$–$C_{10}$ alkylthiocarbonyl, arylaminocarbonyl, and an arylthiocarbonyl group.

11. The compound according to claim 10 wherein $R^2$ is methyl, ethyl, allyl, benzyl or 2-naphthylmethyl.

12. The compound according to claim 10 wherein a $C_1$–$C_{10}$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, of any of $R^1$, $R^2$, $R^3$, or $R^4$ is a $C_1$–$C_7$ alkyl, $C_2$–$C_7$ alkeyl, $C_2$–$C_7$ alkynyl, $C_1$–$C_7$ substituted alkyl, $C_2$–$C_7$ substituted alkenyl, or $C_2$–$C_7$ substituted alkynyl.

* * * * *